(12) United States Patent
Rao et al.

(10) Patent No.: US 9,951,353 B2
(45) Date of Patent: Apr. 24, 2018

(54) ENGINEERING NEURAL STEM CELLS USING HOMOLOGOUS RECOMBINATION

(71) Applicant: THE UNITED STATES OF AMERICA, AS REPRESENTED BY THE SECRETARY, DEPARTMENT OF HEALTH & HUMAN SERVICES, Washington, DC (US)

(72) Inventors: Mahendra S. Rao, Timonium, MD (US); Nasir Malik, Bethesda, MD (US); Raymond Funahashi, West Chester, PA (US); Jizhong Zou, Bethesda, MD (US)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 0 days.

(21) Appl. No.: 15/035,958

(22) PCT Filed: Nov. 14, 2014

(86) PCT No.: PCT/US2014/065769
§ 371 (c)(1),
(2) Date: May 11, 2016

(87) PCT Pub. No.: WO2015/073867
PCT Pub. Date: May 21, 2015

(65) Prior Publication Data
US 2016/0264999 A1 Sep. 15, 2016

Related U.S. Application Data

(60) Provisional application No. 61/904,999, filed on Nov. 15, 2013, provisional application No. 61/905,002, filed on Nov. 15, 2013.

(51) Int. Cl.
| | |
|---|---|
| C12N 5/00 | (2006.01) |
| C12N 15/90 | (2006.01) |
| C12N 5/0797 | (2010.01) |
| A61K 35/30 | (2015.01) |
| A61K 48/00 | (2006.01) |

(52) U.S. Cl.
CPC ............ *C12N 15/907* (2013.01); *A61K 35/30* (2013.01); *C12N 5/0623* (2013.01); *A61K 48/00* (2013.01); *C12N 2501/60* (2013.01); *C12N 2510/00* (2013.01)

(58) Field of Classification Search
USPC .................................. 435/325, 455
See application file for complete search history.

(56) References Cited

U.S. PATENT DOCUMENTS

| | | | | |
|---|---|---|---|---|
| 2005/0064474 A1* | 3/2005 | Urnov | ............. | C07K 14/43595 435/6.18 |
| 2005/0208489 A1* | 9/2005 | Carroll | ............... | A01K 67/0339 435/6.16 |

FOREIGN PATENT DOCUMENTS

| | | | |
|---|---|---|---|
| WO | WO 2011/011767 | * | 1/2011 |
| WO | WO 2011/097036 | * | 8/2011 |
| WO | WO 2011/100058 | * | 8/2011 |
| WO | WO 2011/104382 | * | 9/2011 |
| WO | 2011/146121 | | 11/2011 |
| WO | WO 2011/146121 | * | 11/2011 |
| WO | 2012/021632 | | 2/2012 |
| WO | WO 2012/015938 | * | 2/2012 |
| WO | 2013/082519 | | 6/2013 |

OTHER PUBLICATIONS

Cui (Clin Exp Metastasis, 2009, vol. 26, p. 849-934).*
Lombardo (Molecular Therapy, May 2009, vol. 17, No. Suppl. 1, p. S168).*
Papapetrou (Blood, 2010, vol. 116, Abstract 564).*
Benabdallah (Cytotherapy, 2010, 12, 394-399).*
DeKelver (Genome Res., 2010, 1133-1142).*
Hockemeyer (Nature Biotechnol., Jul. 7, 2011, vol. 29, p. 731-734).*
Wang (Circ. Res. Dec. 7, 2012, vol. 111, No. 12, p. 1494-1503).*
Anguela (Blood, Nov. 15, 2013, vol. 122, No. 21, p. 720).*
Pfeifer (Annu. Rev. Genomics. Hum. Genet. 2001, vol. 2, p. 177-211.*
Johnson-Saliba (Curr. Drug. Targets, 2001, vol. 2, p. 371-399).*
Shoji (Current Pharmaceutical Design, 2004, vol. 10, p. 785-796).*
Edelstein (Journal Gene Med., 2004, vol. 6, p. 597-602).*
Bibikova (Mol. Cellular Biol., 2001, vol. 21, No. 1, p. 289-297).*
High (Nature, 2005, vol. 435, p. 577 and 579).*
Porteus (Nature Biotechnology, Aug. 2005, vol. 23, No. 8, p. 967-973).*
Ramirez (Unexpected failure rates for modular assembly of engineered zinc fingers. Nature Methods, 2008, 5(5): 374-375).*
Lin (Human Molecular Genetics, 2012, vol. 21, No. 11, p. 2610-2617).*
Cerbini (PLoS One, Jan. 14, 2015, p. 1-18).*
Morikawa (Biochem. & Biophysical Res. Comm., 2001, vol. 289, p. 1282-1286).*
OM entry for citrate lyase beta like gene, 2017.*

(Continued)

*Primary Examiner* — Michael C Wilson
(74) *Attorney, Agent, or Firm* — Licata & Tyrrell P.C.

(57) ABSTRACT

Described herein are recombinant polynucleotide-binding polypeptides, recombinant fusion proteins made with the described polynucleotide-binding polypeptides, methods of using the described recombinant polynucleotide-binding polypeptides and recombinant fusion proteins to modify genomic DNA of cells and, in some embodiments, create recombinant cells. Methods are also provided herein for genetically modifying a neuronal stem cell. Methods are also provided for treating a neurological disorder in a subject that include the administration of genetically modified neuronal stem cells produced by the methods disclosed herein.

1 Claim, 18 Drawing Sheets

(56) References Cited

OTHER PUBLICATIONS

Stritmatter (Human Mol. Genetics, 2014, vol. 23, No. 9, p. 2313-2323).*

Office Action in Canadian Patent Application No. 2,930,590 dated Feb. 23, 2017.

Ding et al. "A TALEN Genome Editing System for Generating Human Stem Cell-Based Disease Models" Cell Stem Cell 2013 12:238-251.

Luo et al. "Stable Enhanced Green Fluoresecent Protein Expression After Differentiation and Transplantation of Reporter human Induced Pluripotent Stem Cells Generated by AAVS1 Transcription Activator-Like Effector Nucleases" Stem Cells Translational Medicine 2014 3: 821-835.

Choi-Lundberg et al. "Dopaminergic neurons protected from degeneration by GDNF gene therapy" Science 1997 275:838-841.

Deacon et al. "Histological evidence of fetal pig neural cell survival after transplantation into a patient with Parkinson's disease" 1997 Nature Med. 3:350-353.

Hockemeyer et al. "Genetic engineering of human pluripotent cells using TALE nucleases" Nature biotechnology 2011 29: 731-734.

Irion, S. et al. "Identification and targeting of the ROSA26 locus in human embryonic stem cells" Nature biotechnology 2007 25:1477-1482.

Kordower et al. "Neuropathological evidence of graft survival and striatal reinnervation after the transplantation of fetal mesencephalic tissue in a patient with Parkinson's disease" N. Engl. J. Med. 1995 332:1118-1124.

Mali, P. et al. "RNA-guided genome editing of mammalian cells" Science 2013 339:823-826.

Olanow et al. "Fetal nigral transplantation as a therapy for Parkinson's disease" Trends Neurosci. 1996 19:102-109.

Takayama et al. "Basic fibroblast growth factor increases dopaminergic graft survival and function in a rat model of Parkinson's disease" Nature Med. 1995 1:53-58.

Wang, H. et al. "One-step generation of mice carrying mutations in multiple genes by CRISPR/Cas-mediated genome engineering" Cell 2013 153:910-918.

Wenning et al. "Short- and long-term survival and function of unilateral intrastriatal dopaminergic grafts in Parkinson's disease" Ann. Neurol. 1997 42:95-107.

Yang, H. et al. "One-step generation of mice carrying reporter and conditional alleles by CRISPR/Cas-mediated genome engineering" Cell 2013 154:1370-1379.

Zou, J. et al. "Oxidase-deficient neutrophils from X-linked chronic granulomatous disease iPS cells: functional correction by zinc finger nuclease-mediated safe harbor targeting" Blood 2011 117:5561-5572.

Zou, J. et al. "Gene targeting of a disease-related gene in human induced pluripotent stem and embryonic stem cells" Cell Stem Cell 2009 5:97-110.

International Search Report and Written Opinion in PCT/US2014/065769 dated Mar. 26, 2015.

International Preliminary Report on Patentability in PCT/US2014/065769 dated May 17, 2016.

* cited by examiner

FIG. 2C NCRM1NSC-AS1 -iCLHN Kayotype

FIG. 2D NCRM1NSC-AS1 -iCLHN neuron & astrocyte differentiation

AAVS1 5'-Probe clone9 (46, XY)

Clone 9 (Single-Allele Targeted)

clone 10

FIG. 6A

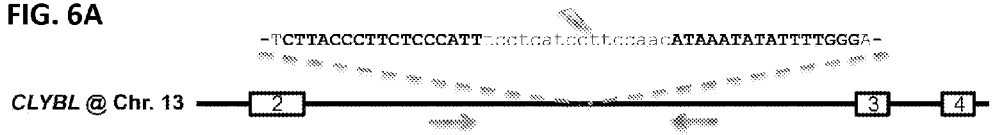

FIG. 6B

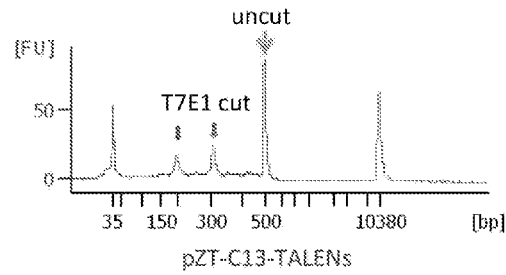

NHEJ efficiency: ~25%

FIG. 6C

```
CTTACCCTTCTCCCATTTCCTCATCCTTCCAACATAAATATATTTTGGGATTATATCAACAT  (36)
CTTACCCTTCTCCCATTTCC----------AACATAAATATATTTTGGGATTATATCAACAT  (1)
CTTACCCTTCTCCCATTTCCTC-----------ATAAATATATTTTGGGATTATATCAACAT  (1)
CTTACCCTTCTCCCATTTCCTCA--------ACATAAATATATTTTGGGATTATATCAACAT  (1)
CTTACCCTTCTCCCATTTCCTCATCCTT----------ATATTTTGGGATTATATCAACAT  (1)
CTTACCCTTCTCCCATTTCC-----------------------------------ACAT  (1)
CTTACCCTTCTCCCATT-------------------------------------CAACAT  (1)
CTTACCCTTCTCCCATTTCCTCATCCT----------ATATATTTGGGATTATATCAACAT  (1)
CTTACCCTTCTCCCATTTCCTC-----------ATAAATATATTTGGGATTATATCAACAT  (1)
CTTACCCTTCTCCCATT-------------------------------------CAACAT  (1)
CTTACCCTTCTCCCATTTCCTC-----------ATAAATATATTTGGGATTATATCAACAT  (1)
CTTACCCTTCCCCCATTTCCTCATCCTTCCAACATAAATATATTTTGGGATTATATCAACAT  (1)
CTTACCCTTCTCCCATTT----A----TCCAACATAAATATATTTGGGATTATATCAACAT  (1)
```

NHEJ efficiency=12/48=25%

AAVS1 5'-Probe

Clone 11 (46, XY)

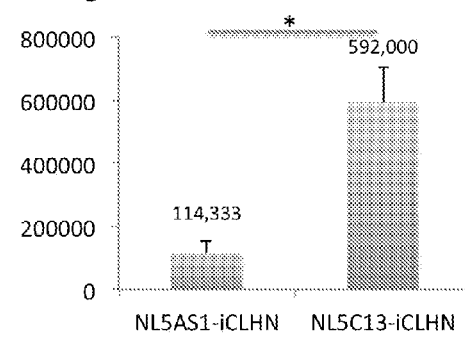
FIG. 8A
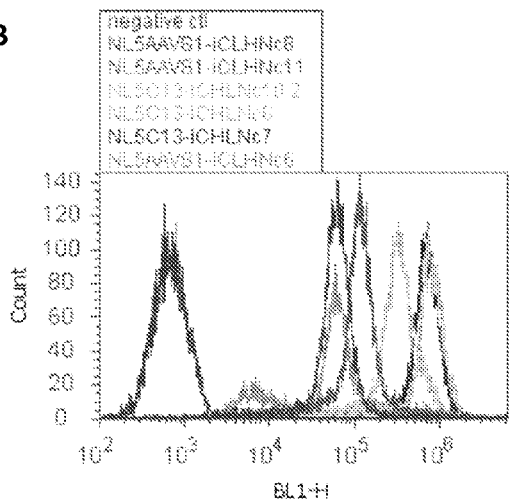
FIG. 8B
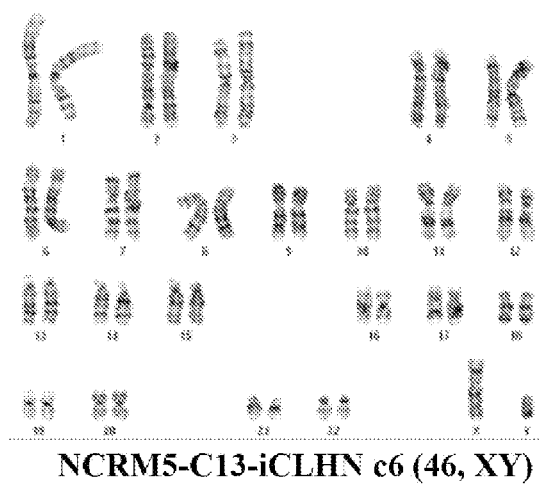
FIG. 8C
NCRM5-C13-iCLHN c6 (46, XY)
FIG. 8D
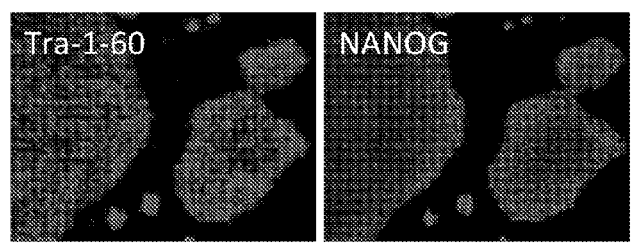

FIG. 8E
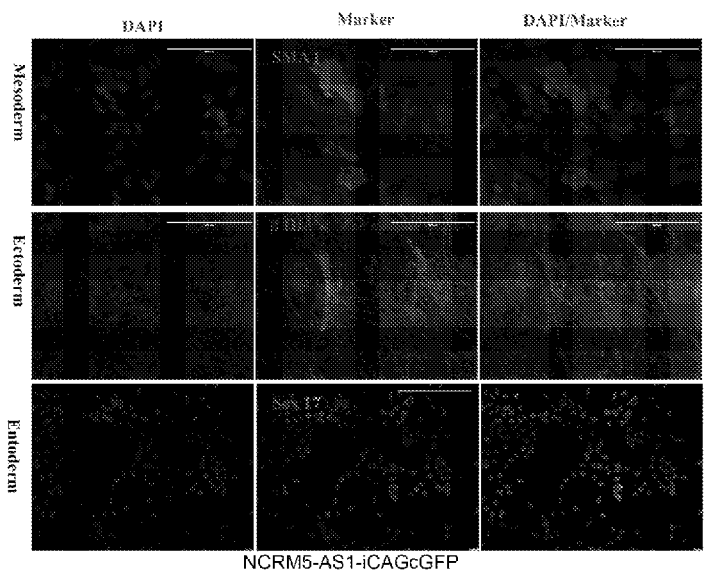
FIG. 8F
FIG. 9
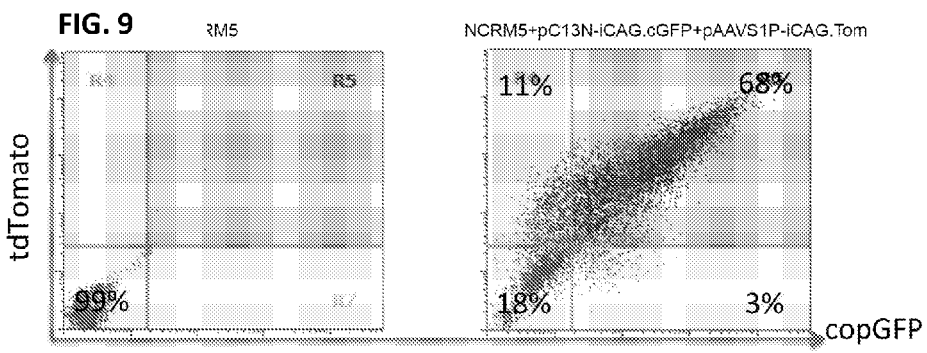

AAVS1 probe/SphI

CLYBL probe/BamHI

NCRM5-AS1Tom-C13GFP c1 (46,XY)

Fig. 15
Left and Right AAVS1 TALEN vectors
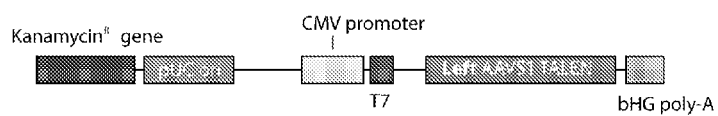
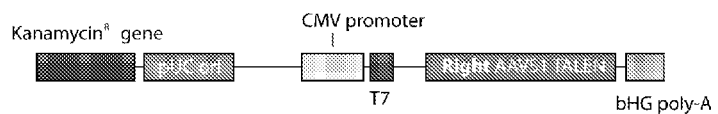
AAVS1 Donor vector

SEQUENCE LISTING

<160> NUMBER OF SEQ ID NOS: 21

<210> SEQ ID NO 1

<211> LENGTH: 17
<212> TYPE: DNA
<213> ORGANISM: HUMAN

<400> SEQUENCE: 1
cttacccttc tcccatt                                                    17

<210> SEQ ID NO 2
<211> LENGTH: 1692
<212> TYPE: DNA
<213> ORGANISM: HUMAN

<400> SEQUENCE: 2
ctgaccccgg accaagtggt ggctatcgcc agccacgatg gcggcaagca agcgctcgaa     60
acggtgcagc ggctgttgcc ggtgctgtgc caggaccatg gcctgacccc ggaccaagtg    120
gtggctatcg ccagcaacgg tggcggcaag caagcgctcg aaacggtgca gcggctgttg    180
ccggtgctgt gccaggacca tggcctgacc ccggaccaag tggtggctat cgccagcaac    240
ggtggcggca agcaagcgct cgaaacggtg cagcggctgt tgccggtgct gtgccaggac    300
catggcctga ccccggacca agtggtggct atcgccagca acattggcgg caagcaagcg    360
ctcgaaacgg tgcagcggct gttgccggtg ctgtgccagg accatggcct gactccggac    420
caagtggtgg ctatcgccag ccacgatggc ggcaagcaag cgctcgaaac ggtgcagcgg    480
ctgttgccgg tgctgtgcca ggaccatggc ctgactccgg accaagtggt ggctatcgcc    540
agccacgatg gcggcaagca agcgctcgaa acggtgcagc ggctgttgcc ggtgctgtgc    600
caggaccatg gcctgactcc ggaccaagtg gtggctatcg ccagccacga tggcggcaag    660
caagcgctcg aaacggtgca gcggctgttg ccggtgctgt gccaggacca tggcctgacc    720
ccggaccaag tggtggctat cgccagcaac ggtggcggca agcaagcgct cgaaacggtg    780
cagcggctgt tgccggtgct gtgccaggac catggcctga ccccggacca agtggtggct    840
atcgccagca acgtggcgg caagcaagcg ctcgaaacgg tgcagcggct gttgccggtg    900
ctgtgccagg accatggcct gactccggac caagtggtgg ctatcgccag ccacgatggc    960
ggcaagcaag cgctcgaaac ggtgcagcgg ctgttgccgg tgctgtgcca ggaccatggc   1020
ctgaccccgg accaagtggt ggctatcgcc agcaacggtg gcggcaagca agcgctcgaa   1080
acggtgcagc ggctgttgcc ggtgctgtgc caggaccatg gcctgactcc ggaccaagtg   1140
gtggctatcg ccagccacga tggcggcaag caagcgctcg aaacggtgca gcggctgttg   1200
ccggtgctgt gccaggacca tggcctgact ccggaccaag tggtggctat cgccagccac   1260
gatggcggca agcaagcgct cgaaacggtg cagcggctgt tgccggtgct gtgccaggac   1320
catggcctga ctccggacca agtggtggct atcgccagcc acgatggcgg caagcaagcg   1380
ctcgaaacgg tgcagcggct gttgccggtg ctgtgccagg accatggcct gaccccggac   1440
caagtggtgg ctatcgccag caacattggc ggcaagcaag cgctcgaaac ggtgcagcgg   1500
ctgttgccgg tgctgtgcca ggaccatggc ctgaccccgg accaagtggt ggctatcgcc   1560
agcaacggtg gcggcaagca agcgctcgaa acggtgcagc ggctgttgcc ggtgctgtgc   1620
caggaccatg gcctgacccc ggaccaagtg gtggctatcg ccagcaacgg tggcggcaag   1680
caagcgctcg aa                                                      1692

<210> SEQ ID NO 3
<211> LENGTH: 16
<212> TYPE: DNA
<213> ORGANISM: HUMAN

<400> SEQUENCE: 3
cccaaaatat atttat    16

<210> SEQ ID NO 4
<211> LENGTH: 1590
<212> TYPE: DNA
<213> ORGANISM: HUMAN

<400> SEQUENCE: 4
ctgaccccgg accaagtggt ggctatcgcc agccacgatg gcggcaagca agcgctcgaa    60
acggtgcagc ggctgttgcc ggtgctgtgc caggaccatg gcctgactcc ggaccaagtg   120
gtggctatcg ccagccacga tggcggcaag caagcgctcg aaacggtgca gcggctgttg   180
ccggtgctgt gccaggacca tggcctgact ccggaccaag tggtggctat cgccagccac   240
gatggcggca agcaagcgct cgaaacggtg cagcggctgt gccggtgct gtgccaggac   300
catggcctga ccccggacca agtggtggct atcgccagca acattggcgg caagcaagcg   360
ctcgaaacgg tgcagcggct gttgccggtg ctgtgccagg accatggcct gaccccggac   420
caagtggtgg ctatcgccag caacattggc ggcaagcaag cgctcgaaac ggtgcagcgg   480
ctgttgccgg tgctgtgcca ggaccatggc ctgaccccgg accaagtggt ggctatcgcc   540
agcaacattg gcggcaagca agcgctcgaa acggtgcagc ggctgttgcc ggtgctgtgc   600
caggaccatg gcctgacccc ggaccaagtg gtggctatcg ccagcaacat tggcggcaag   660
caagcgctcg aaacggtgca gcggctgttg ccggtgctgt gccaggacca tggcctgacc   720
ccggaccaag tggtggctat cgccagcaac ggtggcggca agcaagcgct cgaaacggtg   780
cagcggctgt tgccggtgct gtgccaggac catggcctga ccccggacca agtggtggct   840
atcgccagca acattggcgg caagcaagcg ctcgaaacgg tgcagcggct gttgccggtg   900
ctgtgccagg accatggcct gaccccggac caagtggtgg ctatcgccag caacggtggc   960
ggcaagcaag cgctcgaaac ggtgcagcgg ctgttgccgg tgctgtgcca ggaccatggc  1020
ctgaccccgg accaagtggt ggctatcgcc agcaacattg gcggcaagca agcgctcgaa  1080
acggtgcagc ggctgttgcc ggtgctgtgc caggaccatg gcctgacccc ggaccaagtg  1140
gtggctatcg ccagcaacgg tggcggcaag caagcgctcg aaacggtgca gcggctgttg  1200
ccggtgctgt gccaggacca tggcctgacc ccggaccaag tggtggctat cgccagcaac  1260
ggtggcggca agcaagcgct cgaaacggtg cagcggctgt tgccggtgct gtgccaggac  1320
catggcctga ccccggacca agtggtggct atcgccagca acgtggcgg caagcaagcg  1380
ctcgaaacgg tgcagcggct gttgccggtg ctgtgccagg accatggcct gaccccggac  1440
caagtggtgg ctatcgccag caacattggc ggcaagcaag cgctcgaaac ggtgcagcgg  1500
ctgttgccgg tgctgtgcca ggaccatggc ctgaccccgg accaagtggt ggctatcgcc  1560
agcaacggtg gcggcaagca agcgctcgaa                                   1590

<210> SEQ ID NO 5
<211> LENGTH: 2889
<212> TYPE: DNA
<213> ORGANISM: HUMAN

<400> SEQUENCE: 5
gtggacttga ggacactcgg ttattcgcaa cagcaacagg agaaaatcaa gcctaaggtc    60
aggagcaccg tcgcgcaaca ccacgaggcg cttgtggggc atggcttcac tcatgcgcat   120

```
attgtcgcgc tttcacagca ccctgcggcg cttgggacgg tggctgtcaa ataccaagat    180
atgattgcgg ccctgcccga agccacgcac gaggcaattg taggggtcgg taaacagtgg    240
tcgggagcgc gagcacttga ggccttgctg actgtggcgg gtgagcttag ggggcctccg    300
ctccagctcg acaccgggca gctgctgaag atcgcgaaga gaggggggagt aacagcggta    360
gaggcagtgc acgcctggcg caatgcgctc accggggccc ccctgaacct gaccccggac    420
caagtggtgg ctatcgccag ccacgatggc ggcaagcaag cgctcgaaac ggtgcagcgg    480
ctgttgccgg tgctgtgcca ggaccatggc ctgaccccgg accaagtggt ggctatcgcc    540
agcaacggtg gcggcaagca agcgctcgaa acggtgcagc ggctgttgcc ggtgctgtgc    600
caggaccatg gcctgacccc ggaccaagtg gtggctatcg ccagcaacgg tggcggcaag    660
caagcgctcg aaacggtgca gcggctgttg ccggtgctgt gccaggacca tggcctgacc    720
ccggaccaag tggtggctat cgccagcaac attggcggca agcaagcgct cgaaacggtg    780
cagcggctgt tgccggtgct gtgccaggac catggcctga ctccggacca agtggtggct    840
atcgccagcc acgatggcgg caagcaagcg ctcgaaacgg tgcagcggct gttgccggtg    900
ctgtgccagg accatggcct gactccggac caagtggtgg ctatcgccag ccacgatggc    960
ggcaagcaag cgctcgaaac ggtgcagcgg ctgttgccgg tgctgtgcca ggaccatggc   1020
ctgactccgg accaagtggt ggctatcgcc agccacgatg gcggcaagca agcgctcgaa   1080
acggtgcagc ggctgttgcc ggtgctgtgc caggaccatg gcctgacccc ggaccaagtg   1140
gtggctatcg ccagcaacgg tggcggcaag caagcgctcg aaacggtgca gcggctgttg   1200
ccggtgctgt gccaggacca tggcctgacc ccggaccaag tggtggctat cgccagcaac   1260
ggtggcggca agcaagcgct cgaaacggtg cagcggctgt tgccggtgct gtgccaggac   1320
catggcctga ctccggacca gtggtggct atcgccagcc acgatggcgg caagcaagcg   1380
ctcgaaacgg tgcagcggct gttgccggtg ctgtgccagg accatggcct gaccccggac   1440
caagtggtgg ctatcgccag caacggtggc ggcaagcaag cgctcgaaac ggtgcagcgg   1500
ctgttgccgg tgctgtgcca ggaccatggc ctgactccgg accaagtggt ggctatcgcc   1560
agccacgatg gcggcaagca agcgctcgaa acggtgcagc ggctgttgcc ggtgctgtgc   1620
caggaccatg gcctgactcc ggaccaagtg gtggctatcg ccagccacga tggcggcaag   1680
caagcgctcg aaacggtgca gcggctgttg ccggtgctgt gccaggacca tggcctgact   1740
ccggaccaag tggtggctat cgccagccac gatggcggca agcaagcgct cgaaacggtg   1800
cagcggctgt tgccggtgct gtgccaggac catggcctga ccccggacca agtggtggct   1860
atcgccagca acattggcgg caagcaagcg ctcgaaacgg tgcagcggct gttgccggtg   1920
ctgtgccagg accatggcct gaccccggac caagtggtgg ctatcgccag caacggtggc   1980
ggcaagcaag cgctcgaaac ggtgcagcgg ctgttgccgg tgctgtgcca ggaccatggc   2040
ctgaccccgg accaagtggt ggctatcgcc agcaacggtg gcggcaagca agcgctcgaa   2100
agcattgtgg cccagctgag ccggcctgat ccggcgttgg ccgcgttgac caacgaccat   2160
ctggtggcgt tggcatgtct tggtggacgt cccgcgctcg atgcagtcaa aaagggtctg   2220
cctcatgctc ccgcattgat caaaagaacc aaccggcgga ttcccgagag aacttcccat   2280
cgagtcgcgg gatcccaact agtcaaaagt gaactggagg agaagaaatc tgaacttcgt   2340
cataaattga aatatgtgcc tcatgaatat attgaattaa ttgaaattgc cagaaattcc   2400
actcaggata gaattcttga aatgaaggta atggaatttt ttatgaaagt ttatggatat   2460
agaggtaaac atttgggtgg atcaaggaaa ccggacggag caatttatac tgtcggatct   2520
```

| | |
|---|---|
| cctattgatt acggtgtgat cgtggatact aaagcttata gcggaggtta taatctgcca | 2580 |
| attggccaag cagatgaaat gcaacgatat gtcgaagaaa atcaaacacg aaacaaacat | 2640 |
| atcaacccta atgaatggtg gaaagtctat ccatcttctg taacggaatt taagttttta | 2700 |
| tttgtgagtg gtcactttaa aggaaactac aaagctcagc ttacacgatt aaatcatatc | 2760 |
| actaattgta atggagctgt tcttagtgta gagagctttt taattggtgg agaaatgatt | 2820 |
| aaagccggca cattaaccttt agaggaagtc agacggaaat ttaataacgg cgagataaac | 2880 |
| tttagatct | 2889 |

<210> SEQ ID NO 6
<211> LENGTH: 2787
<212> TYPE: DNA
<213> ORGANISM: HUMAN

<400> SEQUENCE: 6

| | |
|---|---|
| gtggacttga ggacactcgg ttattcgcaa cagcaacagg agaaaatcaa gcctaaggtc | 60 |
| aggagcaccg tcgcgcaaca ccacgaggcg cttgtggggc atggcttcac tcatgcgcat | 120 |
| attgtcgcgc tttcacagca ccctgcgcg cttgggacgg tggctgtcaa ataccaagat | 180 |
| atgattgcgg ccctgcccga agccacgcac gaggcaattg taggggtcgg taaacagtgg | 240 |
| tcgggagcgc gagcacttga ggccttgctg actgtggcgg gtgagcttag ggggcctccg | 300 |
| ctccagctcg acaccgggca gctgctgaag atcgcgaaga gaggggggagt aacagcggta | 360 |
| gaggcagtgc acgcctggcg caatgcgctc accggggccc ccctgaacct gaccccggac | 420 |
| caagtggtgg ctatcgccag ccacgatggc ggcaagcaag cgctcgaaac ggtgcagcgg | 480 |
| ctgttgccgg tgctgtgcca ggaccatggc ctgactccgg accaagtggt ggctatcgcc | 540 |
| agccacgatg gcggcaagca agcgctcgaa acggtgcagc ggctgttgcc ggtgctgtgc | 600 |
| caggaccatg gcctgactcc ggaccaagtg gtggctatcg ccagccacga tggcggcaag | 660 |
| caagcgctcg aaacggtgca gcggctgttg ccggtgctgt gccaggacca tggcctgacc | 720 |
| ccggaccaag tggtggctat cgccagcaac attggcggca agcaagcgct cgaaacggtg | 780 |
| cagcggctgt tgccggtgct gtgccaggac catggcctga ccccggacca agtggtggct | 840 |
| atcgccagca acattggcgg caagcaagcg ctcgaaacgg tgcagcggct gttgccggtg | 900 |
| ctgtgccagg accatggcct gaccccggac caagtggtgg ctatcgccag caacattggc | 960 |
| ggcaagcaag cgctcgaaac ggtgcagcgg ctgttgccgg tgctgtgcca ggaccatggc | 1020 |
| ctgaccccgg accaagtggt ggctatcgcc agcaacattg gcggcaagca agcgctcgaa | 1080 |
| acggtgcagc ggctgttgcc ggtgctgtgc caggaccatg gcctgacccc ggaccaagtg | 1140 |
| gtggctatcg ccagcaacgg tggcggcaag caagcgctcg aaacggtgca gcggctgttg | 1200 |
| ccggtgctgt gccaggacca tggcctgacc ccggaccaag tggtggctat cgccagcaac | 1260 |
| attggcggca agcaagcgct cgaaacggtg cagcggctgt tgccggtgct gtgccaggac | 1320 |
| catggcctga ccccggacca agtggtggct atcgccagca acgtggcgg caagcaagcg | 1380 |
| ctcgaaacgg tgcagcggct gttgccggtg ctgtgccagg accatggcct gaccccggac | 1440 |
| caagtggtgg ctatcgccag caacattggc ggcaagcaag cgctcgaaac ggtgcagcgg | 1500 |
| ctgttgccgg tgctgtgcca ggaccatggc ctgaccccgg accaagtggt ggctatcgcc | 1560 |
| agcaacggtg gcggcaagca agcgctcgaa acggtgcagc ggctgttgcc ggtgctgtgc | 1620 |
| caggaccatg gcctgacccc ggaccaagtg gtggctatcg ccagcaacgg tggcggcaag | 1680 |

```
caagcgctcg aaacggtgca gcggctgttg ccggtgctgt gccaggacca tggcctgacc    1740
ccggaccaag tggtggctat cgccagcaac ggtggcggca agcaagcgct cgaaacggtg    1800
cagcggctgt tgccggtgct gtgccaggac catggcctga ccccggacca agtggtggct    1860
atcgccagca acattggcgg caagcaagcg ctcgaaacgg tgcagcggct gttgccggtg    1920
ctgtgccagg accatggcct gaccccggac caagtggtgg ctatcgccag caacggtggc    1980
ggcaagcaag cgctcgaaag cattgtggcc cagctgagcc ggcctgatcc ggcgttggcc    2040
gcgttgacca acgaccatct ggtggcgttg gcatgtcttg gtggacgtcc cgcgctcgat    2100
gcagtcaaaa agggtctgcc tcatgctccc gcattgatca aagaaccaa ccggcggatt     2160 cccgagagaa cttcccatcg agtcgcggga tcccaactag tcaaaagtga actggaggag    2220
aagaaatctg aacttcgtca taaattgaaa tatgtgcctc atgaatatat tgaattaatt    2280
gaaattgcca gaaattccac tcaggataga attcttgaaa tgaaggtaat ggaatttttt    2340
atgaaagttt atggatatag aggtaaacat ttgggtggat caaggaaacc ggacggagca    2400
atttatactg tcggatctcc tattgattac ggtgtgatcg tggatactaa agcttatagc    2460
ggaggttata atctgccaat tggccaagca gatgaaatgc aacgatatgt cgaagaaaat    2520
caaacacgaa acaaacatat caaccctaat gaatggtgga agtctatcc atcttctgta     2580 acggaattta gttttttatt tgtgagtggt cactttaaag gaaactacaa agctcagctt    2640
acacgattaa atcatatcac taattgtaat ggagctgttc ttagtgtaga agagcttta     2700 attggtggag aaatgattaa agccggcaca ttaaccttag aggaagtcag acggaaattt    2760
aataacggcg agataaactt tagatct                                      2787
```

<210> SEQ ID NO 7
<211> LENGTH: 564
<212> TYPE: PRT
<213> ORGANISM: HUMAN

<400> SEQUENCE: 7

```
Leu Thr Pro Asp Gln Val Val Ala Ile Ala Ser His Asp Gly Gly Lys
1               5                   10                  15

Gln Ala Leu Glu Thr Val Gln Arg Leu Pro Val Leu Cys Gln Asp
            20                  25                  30

His Gly Leu Thr Pro Asp Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Asp His Gly Leu Thr Pro Asp Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Asp His Gly Leu Thr Pro Asp Gln Val Val Ala Ile Ala
            100                 105                 110

Ser Asn Ile Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175
```

```
Val Ala Ile Ala Ser His Asp Gly Gly Lys Gln Ala Leu Glu Thr Val
                180                 185                 190
Gln Arg Leu Leu Pro Val Leu Cys Gln Asp His Gly Leu Thr Pro Asp
            195                 200                 205
Gln Val Val Ala Ile Ala Ser His Asp Gly Gly Lys Gln Ala Leu Glu
        210                 215                 220
Thr Val Gln Arg Leu Leu Pro Val Leu Cys Gln Asp His Gly Leu Thr
225                 230                 235                 240
Pro Asp Gln Val Val Ala Ile Ala Ser Asn Gly Gly Lys Gln Ala
                245                 250                 255
Leu Glu Thr Val Gln Arg Leu Leu Pro Val Leu Cys Gln Asp His Gly
            260                 265                 270
Leu Thr Pro Asp Gln Val Val Ala Ile Ala Ser Asn Gly Gly Gly Lys
        275                 280                 285
Gln Ala Leu Glu Thr Val Gln Arg Leu Leu Pro Val Leu Cys Gln Asp
    290                 295                 300
His Gly Leu Thr Pro Asp Gln Val Val Ala Ile Ala Ser His Asp Gly
305                 310                 315                 320
Gly Lys Gln Ala Leu Glu Thr Val Gln Arg Leu Leu Pro Val Leu Cys
                325                 330                 335
Gln Asp His Gly Leu Thr Pro Asp Gln Val Val Ala Ile Ala Ser Asn
            340                 345                 350
Gly Gly Gly Lys Gln Ala Leu Glu Thr Val Gln Arg Leu Leu Pro Val
        355                 360                 365
Leu Cys Gln Asp His Gly Leu Thr Pro Asp Gln Val Val Ala Ile Ala
370                 375                 380
Ser His Asp Gly Gly Lys Gln Ala Leu Glu Thr Val Gln Arg Leu Leu
385                 390                 395                 400
Pro Val Leu Cys Gln Asp His Gly Leu Thr Pro Asp Gln Val Val Ala
                405                 410                 415
Ile Ala Ser His Asp Gly Gly Lys Gln Ala Leu Glu Thr Val Gln Arg
            420                 425                 430
Leu Leu Pro Val Leu Cys Gln Asp His Gly Leu Thr Pro Asp Gln Val
        435                 440                 445
Val Ala Ile Ala Ser His Asp Gly Gly Lys Gln Ala Leu Glu Thr Val
450                 455                 460
Gln Arg Leu Leu Pro Val Leu Cys Gln Asp His Gly Leu Thr Pro Asp
465                 470                 475                 480
Gln Val Val Ala Ile Ala Ser Asn Ile Gly Gly Lys Gln Ala Leu Glu
                485                 490                 495
Thr Val Gln Arg Leu Leu Pro Val Leu Cys Gln Asp His Gly Leu Thr
            500                 505                 510
Pro Asp Gln Val Val Ala Ile Ala Ser Asn Gly Gly Lys Gln Ala
        515                 520                 525
Leu Glu Thr Val Gln Arg Leu Leu Pro Val Leu Cys Gln Asp His Gly
530                 535                 540
Leu Thr Pro Asp Gln Val Val Ala Ile Ala Ser Asn Gly Gly Gly Lys
545                 550                 555                 560
Gln Ala Leu Glu

<210> SEQ ID NO 8
<211> LENGTH: 963
<212> TYPE: PRT
<213> ORGANISM: HUMAN
```

<400> SEQUENCE: 8

```
Val Asp Leu Arg Thr Leu Gly Tyr Ser Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn Leu Thr Pro Asp Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser Asn Gly Gly Lys Gln Ala Leu Glu
210                 215                 220

Thr Val Gln Arg Leu Leu Pro Val Leu Cys Gln Asp His Gly Leu Thr
225                 230                 235                 240

Pro Asp Gln Val Val Ala Ile Ala Ser Asn Ile Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser His Asp Gly Gly Lys
        275                 280                 285

Gln Ala Leu Glu Thr Val Gln Arg Leu Leu Pro Val Leu Cys Gln Asp
    290                 295                 300

His Gly Leu Thr Pro Asp Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Asp His Gly Leu Thr Pro Asp Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Asp His Gly Leu Thr Pro Asp Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
```

```
                405                 410                 415
Ile Ala Ser Asn Gly Gly Gly Lys Gln Ala Leu Glu Thr Val Gln Arg
            420                 425                 430

Leu Leu Pro Val Leu Cys Gln Asp His Gly Leu Thr Pro Asp Gln Val
            435                 440                 445

Val Ala Ile Ala Ser His Asp Gly Gly Lys Gln Ala Leu Glu Thr Val
            450                 455                 460

Gln Arg Leu Leu Pro Val Leu Cys Gln Asp His Gly Leu Thr Pro Asp
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Asp His Gly Leu Thr
            500                 505                 510

Pro Asp Gln Val Val Ala Ile Ala Ser His Asp Gly Gly Lys Gln Ala
            515                 520                 525

Leu Glu Thr Val Gln Arg Leu Leu Pro Val Leu Cys Gln Asp His Gly
            530                 535                 540

Leu Thr Pro Asp Gln Val Val Ala Ile Ala Ser His Asp Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Asp Gln Val Val Ala Ile Ala Ser His Asp Gly
            580                 585                 590

Gly Lys Gln Ala Leu Glu Thr Val Gln Arg Leu Leu Pro Val Leu Cys
            595                 600                 605

Gln Asp His Gly Leu Thr Pro Asp Gln Val Val Ala Ile Ala Ser Asn
            610                 615                 620

Ile Gly Gly Lys Gln Ala Leu Glu Thr Val Gln Arg Leu Leu Pro Val
625                 630                 635                 640

Leu Cys Gln Asp His Gly Leu Thr Pro Asp Gln Val Val Ala Ile Ala
                645                 650                 655

Ser Asn Gly Gly Gly Lys Gln Ala Leu Glu Thr Val Gln Arg Leu Leu
            660                 665                 670

Pro Val Leu Cys Gln Asp His Gly Leu Thr Pro Asp Gln Val Val Ala
            675                 680                 685

Ile Ala Ser Asn Gly Gly Gly Lys Gln Ala Leu Glu Ser Ile Val Ala
            690                 695                 700

Gln Leu Ser Arg Pro Asp Pro Ala Leu Ala Ala Leu Thr Asn Asp His
705                 710                 715                 720

Leu Val Ala Leu Ala Cys Leu Gly Gly Arg Pro Ala Leu Asp Ala Val
                725                 730                 735

Lys Lys Gly Leu Pro His Ala Pro Ala Leu Ile Lys Arg Thr Asn Arg
            740                 745                 750

Arg Ile Pro Glu Arg Thr Ser His Arg Val Ala Gly Ser Gln Leu Val
            755                 760                 765

Lys Ser Glu Leu Glu Glu Lys Lys Ser Glu Leu Arg His Lys Leu Lys
            770                 775                 780

Tyr Val Pro His Glu Tyr Ile Glu Leu Ile Glu Ile Ala Arg Asn Ser
785                 790                 795                 800

Thr Gln Asp Arg Ile Leu Glu Met Lys Val Met Glu Phe Phe Met Lys
                805                 810                 815

Val Tyr Gly Tyr Arg Gly Lys His Leu Gly Gly Ser Arg Lys Pro Asp
            820                 825                 830
```

```
Gly Ala Ile Tyr Thr Val Gly Ser Pro Ile Asp Tyr Gly Val Ile Val
            835                 840                 845

Asp Thr Lys Ala Tyr Ser Gly Gly Tyr Asn Leu Pro Ile Gly Gln Ala
        850                 855                 860

Asp Glu Met Gln Arg Tyr Val Glu Glu Asn Gln Thr Arg Asn Lys His
865                 870                 875                 880

Ile Asn Pro Asn Glu Trp Trp Lys Val Tyr Pro Ser Ser Val Thr Glu
                885                 890                 895

Phe Lys Phe Leu Phe Val Ser Gly His Phe Lys Gly Asn Tyr Lys Ala
            900                 905                 910

Gln Leu Thr Arg Leu Asn His Ile Thr Asn Cys Asn Gly Ala Val Leu
        915                 920                 925

Ser Val Glu Glu Leu Leu Ile Gly Gly Glu Met Ile Lys Ala Gly Thr
    930                 935                 940

Leu Thr Leu Glu Glu Val Arg Arg Lys Phe Asn Asn Gly Glu Ile Asn
945                 950                 955                 960

Phe Arg Ser
```

<210> SEQ ID NO 9
<211> LENGTH: 3006
<212> TYPE: DNA
<213> ORGANISM: HUMAN

<400> SEQUENCE: 9

```
atggactaca aagaccatga cggtgattat aaagatcatg acatcgatta caaggatgac     60
gatgacaaga tggcccccaa gaagaagagg aaggtgggca tccacggggt acctatggtg    120
gacttgagga cactcggtta ttcgcaacag caacaggaga aaatcaagcc taaggtcagg    180
agcaccgtcg cgcaacacca cgaggcgctt gtggggcatg gcttcactca tgcgcatatt    240
gtcgcgcttt cacagcaccc tgcggcgctt gggacggtgg ctgtcaaata ccaagatatg    300
attgcggccc tgcccgaagc cacgcacgag gcaattgtag gggtcggtaa acagtggtcg    360
ggagcgcgag cacttgaggc cttgctgact gtggcgggtg agcttagggg gcctccgctc    420
cagctcgaca ccgggcagct gctgaagatc gcgaagagag ggggagtaac agcggtagag    480
gcagtgcacg cctggcgcaa tgcgctcacc ggggcccccc tgaacctgac cccggaccaa    540
gtggtggcta tcgccagcca cgatggcggc aagcaagcgc tcgaaacggt gcagcggctg    600
ttgccggtgc tgtgccagga ccatggcctg accccggacc aagtggtggc tatcgccagc    660
aacggtggcg gcaagcaagc gctcgaaacg gtgcagcggc tgttgccggt gctgtgccag    720
gaccatggcc tgaccccgga ccaagtggtg gctatcgcca gcaacggtgg cggcaagcaa    780
gcgctcgaaa cggtgcagcg gctgttgccg gtgctgtgcc aggaccatgg cctgaccccg    840
gaccaagtgg tggctatcgc cagcaacatt ggcggcaagc aagcgctcga aacggtgcag    900
cggctgttgc cggtgctgtg ccaggaccat ggcctgactc cggaccaagt ggtggctatc    960
gccagccacg atggcggcaa gcaagcgctc gaaacggtgc agcggctgtt gccggtgctg   1020
tgccaggacc atggcctgac tccggaccaa gtggtggcta tcgccagcca cgatggcggc   1080
aagcaagcgc tcgaaacggt gcagcggctg ttgccggtgc tgtgccagga ccatggcctg   1140
actccggacc aagtggtggc tatcgccagc cacgatggcg gcaagcaagc gctcgaaacg   1200
gtgcagcggc tgttgccggt gctgtgccag gaccatggcc tgaccccgga ccaagtggtg   1260
gctatcgcca gcaacggtgg cggcaagcaa gcgctcgaaa cggtgcagcg gctgttgccg   1320
```

```
gtgctgtgcc aggaccatgg cctgaccccg gaccaagtgg tggctatcgc cagcaacggt    1380
ggcggcaagc aagcgctcga aacggtgcag cggctgttgc cggtgctgtg ccaggaccat    1440
ggcctgactc cggaccaagt ggtggctatc gccagccacg atggcggcaa gcaagcgctc    1500
gaaacggtgc agcggctgtt gccggtgctg tgccaggacc atggcctgac cccggaccaa    1560
gtggtggcta tcgccagcaa cggtggcggc aagcaagcgc tcgaaacggt gcagcggctg    1620
ttgccggtgc tgtgccagga ccatggcctg actccggacc aagtggtggc tatcgccagc    1680
cacgatggcg gcaagcaagc gctcgaaacg gtgcagcggc tgttgccggt gctgtgccag    1740
gaccatggcc tgactccgga ccaagtggtg ctatcgcca gccacgatgg cggcaagcaa    1800
gcgctcgaaa cggtgcagcg gctgttgccg gtgctgtgcc aggaccatgg cctgactccg    1860
gaccaagtgg tggctatcgc cagccacgat ggcggcaagc aagcgctcga aacggtgcag    1920
cggctgttgc cggtgctgtg ccaggaccat ggcctgaccc ggaccaagt ggtggctatc    1980
gccagcaaca ttggcggcaa gcaagcgctc gaaacggtgc agcggctgtt gccggtgctg    2040
tgccaggacc atggcctgac cccggaccaa gtggtggcta tcgccagcaa cggtggcggc    2100
aagcaagcgc tcgaaacggt gcagcggctg ttgccggtgc tgtgccagga ccatggcctg    2160
accccggacc aagtggtggc tatcgccagc aacggtggcg gcaagcaagc gctcgaaagc    2220
attgtggccc agctgagccg gcctgatccg gcgttggccg cgttgaccaa cgaccatctg    2280
gtggcgttgg catgtcttgg tggacgtccc gcgctcgatg cagtcaaaaa gggtctgcct    2340
catgctcccg cattgatcaa agaaccaac cggcggattc ccgagagaac ttcccatcga    2400
gtcgcgggat cccaactagt caaaagtgaa ctggaggaga gaaatctga acttcgtcat    2460
aaattgaaat atgtgcctca tgaatatatt gaattaattg aaattgccag aaattccact    2520
caggataaga ttcttgaaat gaaggtaatg gaatttttta tgaaagttta tggatataga    2580
ggtaaacatt tgggtggatc aaggaaaccg gacggagcaa tttatactgt cggatctcct    2640
attgattacg gtgtgatcgt ggatactaaa gcttatagcg gaggttataa tctgccaatt    2700
ggccaagcag atgaaatgca acgatatgtc gaagaaatc aaacacgaaa caaacatatc    2760
aaccctaatg aatggtggaa agtctatcca tcttctgtaa cggaatttaa gtttttattt    2820
gtgagtggtc actttaaagg aaactacaaa gctcagctta cacgattaaa tcatatcact    2880
aattgtaatg gagctgttct tagtgtagaa gagcttttaa ttggtggaga atgattaaa    2940
gccggcacat taaccttaga ggaagtcaga cggaaattta ataacggcga gataaacttt    3000
agatct                                                                3006

<210> SEQ ID NO 10
<211> LENGTH: 530
<212> TYPE: PRT
<213> ORGANISM: HUMAN

<400> SEQUENCE: 10

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Asp Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Asp His Gly Leu Thr Pro Asp Gln Val Val Ala Ile Ala Ser His
```

```
             65                  70                  75                  80
Asp Gly Gly Lys Gln Ala Leu Glu Thr Val Gln Arg Leu Leu Pro Val
                 85                  90                  95
Leu Cys Gln Asp His Gly Leu Thr Pro Asp Gln Val Val Ala Ile Ala
                100                 105                 110
Ser Asn Ile Gly Gly Lys Gln Ala Leu Glu Thr Val Gln Arg Leu Leu
                115                 120                 125
Pro Val Leu Cys Gln Asp His Gly Leu Thr Pro Asp Gln Val Val Ala
130                 135                 140
Ile Ala Ser Asn Ile Gly Gly Lys Gln Ala Leu Glu Thr Val Gln Arg
145                 150                 155                 160
Leu Leu Pro Val Leu Cys Gln Asp His Gly Leu Thr Pro Asp Gln Val
                165                 170                 175
Val Ala Ile Ala Ser Asn Ile Gly Gly Lys Gln Ala Leu Glu Thr Val
                180                 185                 190
Gln Arg Leu Leu Pro Val Leu Cys Gln Asp His Gly Leu Thr Pro Asp
            195                 200                 205
Gln Val Val Ala Ile Ala Ser Asn Ile Gly Gly Lys Gln Ala Leu Glu
            210                 215                 220
Thr Val Gln Arg Leu Leu Pro Val Leu Cys Gln Asp His Gly Leu Thr
225                 230                 235                 240
Pro Asp Gln Val Val Ala Ile Ala Ser Asn Gly Gly Lys Gln Ala
                245                 250                 255
Leu Glu Thr Val Gln Arg Leu Leu Pro Val Leu Cys Gln Asp His Gly
            260                 265                 270
Leu Thr Pro Asp Gln Val Val Ala Ile Ala Ser Asn Ile Gly Gly Lys
            275                 280                 285
Gln Ala Leu Glu Thr Val Gln Arg Leu Leu Pro Val Leu Cys Gln Asp
            290                 295                 300
His Gly Leu Thr Pro Asp Gln Val Val Ala Ile Ala Ser Asn Gly Gly
305                 310                 315                 320
Gly Lys Gln Ala Leu Glu Thr Val Gln Arg Leu Leu Pro Val Leu Cys
                325                 330                 335
Gln Asp His Gly Leu Thr Pro Asp Gln Val Val Ala Ile Ala Ser Asn
            340                 345                 350
Ile Gly Gly Lys Gln Ala Leu Glu Thr Val Gln Arg Leu Leu Pro Val
            355                 360                 365
Leu Cys Gln Asp His Gly Leu Thr Pro Asp Gln Val Val Ala Ile Ala
            370                 375                 380
Ser Asn Gly Gly Lys Gln Ala Leu Glu Thr Val Gln Arg Leu Leu
385                 390                 395                 400
Pro Val Leu Cys Gln Asp His Gly Leu Thr Pro Asp Gln Val Val Ala
                405                 410                 415
Ile Ala Ser Asn Gly Gly Lys Gln Ala Leu Glu Thr Val Gln Arg
            420                 425                 430
Leu Leu Pro Val Leu Cys Gln Asp His Gly Leu Thr Pro Asp Gln Val
            435                 440                 445
Val Ala Ile Ala Ser Asn Gly Gly Gly Lys Gln Ala Leu Glu Thr Val
            450                 455                 460
Gln Arg Leu Leu Pro Val Leu Cys Gln Asp His Gly Leu Thr Pro Asp
465                 470                 475                 480
Gln Val Val Ala Ile Ala Ser Asn Ile Gly Gly Lys Gln Ala Leu Glu
            485                 490                 495
```

```
Thr Val Gln Arg Leu Leu Pro Val Leu Cys Gln Asp His Gly Leu Thr
            500                 505                 510

Pro Asp Gln Val Val Ala Ile Ala Ser Asn Gly Gly Lys Gln Ala
        515                 520                 525

Leu Glu
    530

<210> SEQ ID NO 11
<211> LENGTH: 929
<212> TYPE: PRT
<213> ORGANISM: HUMAN

<400> SEQUENCE: 11

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn Leu Thr Pro Asp Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Asp His Gly Leu Thr Pro Asp Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Asp His Gly Leu Thr Pro Asp
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Asp His Gly Leu Thr
225                 230                 235                 240

Pro Asp Gln Val Val Ala Ile Ala Ser Asn Ile Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Ile Gly Gly Lys
        275                 280                 285

Gln Ala Leu Glu Thr Val Gln Arg Leu Leu Pro Val Leu Cys Gln Asp
    290                 295                 300

His Gly Leu Thr Pro Asp Gln Val Val Ala Ile Ala Ser Asn Ile Gly
305                 310                 315                 320

Gly Lys Gln Ala Leu Glu Thr Val Gln Arg Leu Leu Pro Val Leu Cys
```

-continued

```
                325                 330                 335
Gln Asp His Gly Leu Thr Pro Asp Gln Val Ala Ile Ala Ser Asn
            340                 345                 350
Ile Gly Gly Lys Gln Ala Leu Glu Thr Val Gln Arg Leu Leu Pro Val
            355                 360                 365
Leu Cys Gln Asp His Gly Leu Thr Pro Asp Gln Val Ala Ile Ala
        370                 375                 380
Ser Asn Gly Gly Lys Gln Ala Leu Glu Thr Val Gln Arg Leu Leu
385                 390                 395                 400
Pro Val Leu Cys Gln Asp His Gly Leu Thr Pro Asp Gln Val Ala
                405                 410                 415
Ile Ala Ser Asn Ile Gly Gly Lys Gln Ala Leu Glu Thr Val Gln Arg
                420                 425                 430
Leu Leu Pro Val Leu Cys Gln Asp His Gly Leu Thr Pro Asp Gln Val
            435                 440                 445
Val Ala Ile Ala Ser Asn Gly Gly Gly Lys Gln Ala Leu Glu Thr Val
    450                 455                 460
Gln Arg Leu Leu Pro Val Leu Cys Gln Asp His Gly Leu Thr Pro Asp
465                 470                 475                 480
Gln Val Val Ala Ile Ala Ser Asn Ile Gly Gly Lys Gln Ala Leu Glu
                485                 490                 495
Thr Val Gln Arg Leu Leu Pro Val Leu Cys Gln Asp His Gly Leu Thr
            500                 505                 510
Pro Asp Gln Val Val Ala Ile Ala Ser Asn Gly Gly Gly Lys Gln Ala
            515                 520                 525
Leu Glu Thr Val Gln Arg Leu Leu Pro Val Leu Cys Gln Asp His Gly
        530                 535                 540
Leu Thr Pro Asp Gln Val Val Ala Ile Ala Ser Asn Gly Gly Gly Lys
545                 550                 555                 560
Gln Ala Leu Glu Thr Val Gln Arg Leu Leu Pro Val Leu Cys Gln Asp
                565                 570                 575
His Gly Leu Thr Pro Asp Gln Val Val Ala Ile Ala Ser Asn Gly Gly
            580                 585                 590
Gly Lys Gln Ala Leu Glu Thr Val Gln Arg Leu Leu Pro Val Leu Cys
        595                 600                 605
Gln Asp His Gly Leu Thr Pro Asp Gln Val Val Ala Ile Ala Ser Asn
        610                 615                 620
Ile Gly Gly Lys Gln Ala Leu Glu Thr Val Gln Arg Leu Leu Pro Val
625                 630                 635                 640
Leu Cys Gln Asp His Gly Leu Thr Pro Asp Gln Val Val Ala Ile Ala
                645                 650                 655
Ser Asn Gly Gly Gly Lys Gln Ala Leu Glu Ser Ile Val Ala Gln Leu
            660                 665                 670
Ser Arg Pro Asp Pro Ala Leu Ala Ala Leu Thr Asn Asp His Leu Val
        675                 680                 685
Ala Leu Ala Cys Leu Gly Gly Arg Pro Ala Leu Asp Ala Val Lys Lys
        690                 695                 700
Gly Leu Pro His Ala Pro Ala Leu Ile Lys Arg Thr Asn Arg Arg Ile
705                 710                 715                 720
Pro Glu Arg Thr Ser His Arg Val Ala Gly Ser Gln Leu Val Lys Ser
                725                 730                 735
Glu Leu Glu Glu Lys Lys Ser Glu Leu Arg His Lys Leu Lys Tyr Val
            740                 745                 750
```

Pro His Glu Tyr Ile Glu Leu Ile Glu Ile Ala Arg Asn Ser Thr Gln
            755                 760                 765

Asp Arg Ile Leu Glu Met Lys Val Met Glu Phe Phe Met Lys Val Tyr
        770                 775                 780

Gly Tyr Arg Gly Lys His Leu Gly Gly Ser Arg Lys Pro Asp Gly Ala
785                 790                 795                 800

Ile Tyr Thr Val Gly Ser Pro Ile Asp Tyr Gly Val Ile Val Asp Thr
            805                 810                 815

Lys Ala Tyr Ser Gly Gly Tyr Asn Leu Pro Ile Gly Gln Ala Asp Glu
        820                 825                 830

Met Gln Arg Tyr Val Glu Glu Asn Gln Thr Arg Asn Lys His Ile Asn
            835                 840                 845

Pro Asn Glu Trp Trp Lys Val Tyr Pro Ser Ser Val Thr Glu Phe Lys
        850                 855                 860

Phe Leu Phe Val Ser Gly His Phe Lys Gly Asn Tyr Lys Ala Gln Leu
865                 870                 875                 880

Thr Arg Leu Asn His Ile Thr Asn Cys Asn Gly Ala Val Leu Ser Val
            885                 890                 895

Glu Glu Leu Leu Ile Gly Gly Glu Met Ile Lys Ala Gly Thr Leu Thr
        900                 905                 910

Leu Glu Glu Val Arg Arg Lys Phe Asn Asn Gly Glu Ile Asn Phe Arg
            915                 920                 925

Ser

<210> SEQ ID NO 12
<211> LENGTH: 2904
<212> TYPE: DNA
<213> ORGANISM: HUMAN

<400> SEQUENCE: 12
atggactaca aagaccatga cggtgattat aaagatcatg acatcgatta caaggatgac    60
gatgacaaga tggcccccaa gaagaagagg aaggtgggca tccacggggt acctatggtg   120
gacttgagga cactcggtta ttcgcaacag caacaggaga aaatcaagcc taaggtcagg   180
agcaccgtcg cgcaacacca cgaggcgctt gtggggcatg gcttcactca tgcgcatatt   240
gtcgcgcttt cacagcaccc tgcggcgctt ggacggtgg ctgtcaaata ccaagatatg   300
attgcggccc tgcccgaagc cacgcacgag gcaattgtag gggtcggtaa acagtggtcg   360
ggagcgcgag cacttgaggc cttgctgact gtggcgggtg agcttagggg gcctccgctc   420
cagctcgaca ccgggcagct gctgaagatc gcgaagagag ggggagtaac agcggtagag   480
gcagtgcacg cctggcgcaa tgcgctcacc ggggcccccc tgaacctgac cccgaccaa   540 gtggtggcta tcgccagcca cgatggcggc aagcaagcgc tcgaaacggt gcagcggctg   600
ttgccggtgc tgtgccagga ccatggcctg actccggacc aagtggtggc tatcgccagc   660
cacgatggcg gcaagcaagc gctcgaaacg gtgcagcggc tgttgccggt gctgtgccag   720
gaccatggcc tgactccgga ccaagtggtg gctatcgcca gccacgatgg cggcaagcaa   780
gcgctcgaaa cggtgcagcg gctgttgccg gtgctgtgcc aggaccatgg cctgaccccg   840
gaccaagtgg tggctatcgc cagcaacatt ggcggcaagc aagcgctcga acggtgcag   900 cggctgttgc cggtgctgtg ccaggaccat ggcctgaccc cggaccaagt ggtggctatc   960
gccagcaaca ttggcggcaa gcaagcgctc gaaacggtgc agcggctgtt gccggtgctg  1020
tgccaggacc atggcctgac cccggaccaa gtggtggcta tcgccagcaa cattggcggc  1080

```
aagcaagcgc tcgaaacggt gcagcggctg ttgccggtgc tgtgccagga ccatggcctg    1140
accccggacc aagtggtggc tatcgccagc aacattggcg gcaagcaagc gctcgaaacg    1200
gtgcagcggc tgttgccggt gctgtgccag gaccatggcc tgaccccgga ccaagtggtg    1260
gctatcgcca gcaacggtgg cggcaagcaa gcgctcgaaa cggtgcagcg gctgttgccg    1320
gtgctgtgcc aggaccatgg cctgaccccg gaccaagtgg tggctatcgc cagcaacatt    1380
ggcggcaagc aagcgctcga aacggtgcag cggctgttgc cggtgctgtg ccaggaccat    1440
ggcctgaccc cggaccaagt ggtggctatc gccagcaacg gtggcggcaa gcaagcgctc    1500
gaaacggtgc agcggctgtt gccggtgctg tgccaggacc atggcctgac cccggaccaa    1560
gtggtggcta tcgccagcaa cattggcggc aagcaagcgc tcgaaacggt gcagcggctg    1620
ttgccggtgc tgtgccagga ccatggcctg accccggacc aagtggtggc tatcgccagc    1680
aacggtggcg gcaagcaagc gctcgaaacg gtgcagcggc tgttgccggt gctgtgccag    1740
gaccatggcc tgaccccgga ccaagtggtg gctatcgcca gcaacggtgg cggcaagcaa    1800
gcgctcgaaa cggtgcagcg gctgttgccg gtgctgtgcc aggaccatgg cctgaccccg    1860
gaccaagtgg tggctatcgc cagcaacggt ggcggcaagc aagcgctcga aacggtgcag    1920
cggctgttgc cggtgctgtg ccaggaccat ggcctgaccc cggaccaagt ggtggctatc    1980
gccagcaaca ttggcggcaa gcaagcgctc gaaacggtgc agcggctgtt gccggtgctg    2040
tgccaggacc atggcctgac cccggaccaa gtggtggcta tcgccagcaa cggtggcggc    2100
aagcaagcgc tcgaaagcat tgtggcccag ctgagccggc ctgatccggc gttggccgcg    2160
ttgaccaacg accatctggt ggcgttggca tgtcttggtg acgtcccgc gctcgatgca    2220 gtcaaaaagg gtctgcctca tgctcccgca ttgatcaaaa gaaccaaccg gcggattccc    2280
gagagaactt cccatcgagt cgcgggatcc caactagtca aaagtgaact ggaggagaag    2340
aaatctgaac ttcgtcataa attgaaatat gtgcctcatg aatatattga attaattgaa    2400
attgccagaa attccactca ggatagaatt cttgaaatga aggtaatgga atttttttatg    2460 aaagtttatg gatatagagg taaacatttg ggtggatcaa ggaaaccgga cggagcaatt    2520
tatactgtcg gatctcctat tgattacggt gtgatcgtgg atactaaagc ttatagcgga    2580
ggttataatc tgccaattgg ccaagcagat gaaatgcaac gatatgtcga agaaaatcaa    2640
acacgaaaca aacatatcaa ccctaatgaa tggtggaaag tctatccatc ttctgtaacg    2700
gaatttaagt ttttatttgt gagtggtcac tttaaaggaa actacaaagc tcagcttaca    2760
cgattaaatc atatcactaa ttgtaatgga gctgttctta gtgtagaaga cttttaatt    2820 ggtggagaaa tgattaaagc cggcacatta accttagagg aagtcagacg gaaatttaat    2880
aacggcgaga taaactttag atct                                          2904
```

<210> SEQ ID NO 13
<211> LENGTH: 199
<212> TYPE: PRT
<213> ORGANISM: HUMAN

<400> SEQUENCE: 13

```
Ser Gln Leu Val Lys Ser Glu Leu Glu Glu Lys Ser Glu Leu Arg
1               5                   10                  15

His Lys Leu Lys Tyr Val Pro His Glu Tyr Ile Glu Leu Ile Glu Ile
            20                  25                  30

Ala Arg Asn Ser Thr Gln Asp Arg Ile Leu Glu Met Lys Val Met Glu
        35                  40                  45
```

-continued

```
Phe Phe Met Lys Val Tyr Gly Tyr Arg Gly Lys His Leu Gly Gly Ser
 50                  55                  60
Arg Lys Pro Asp Gly Ala Ile Tyr Thr Val Gly Ser Pro Ile Asp Tyr
 65                  70                  75                  80
Gly Val Ile Val Asp Thr Lys Ala Tyr Ser Gly Gly Tyr Asn Leu Pro
                 85                  90                  95
Ile Gly Gln Ala Asp Glu Met Gln Arg Tyr Val Glu Glu Asn Gln Thr
            100                 105                 110
Arg Asn Lys His Ile Asn Pro Asn Glu Trp Trp Lys Val Tyr Pro Ser
        115                 120                 125
Ser Val Thr Glu Phe Lys Phe Leu Phe Val Ser Gly His Phe Lys Gly
    130                 135                 140
Asn Tyr Lys Ala Gln Leu Thr Arg Leu Asn His Ile Thr Asn Cys Asn
145                 150                 155                 160
Gly Ala Val Leu Ser Val Glu Glu Leu Leu Ile Gly Gly Glu Met Ile
                165                 170                 175
Lys Ala Gly Thr Leu Thr Leu Glu Glu Val Arg Arg Lys Phe Asn Asn
            180                 185                 190
Gly Glu Ile Asn Phe Arg Ser
        195
```

<210> SEQ ID NO 14
<211> LENGTH: 597
<212> TYPE: DNA
<213> ORGANISM: HUMAN

<400> SEQUENCE: 14

```
tcccaactag tcaaaagtga actggaggag aagaaatctg aacttcgtca taaattgaaa    60
tatgtgcctc atgaatatat tgaattaatt gaaattgcca gaaattccac tcaggataga   120
attcttgaaa tgaaggtaat ggattttttt atgaaagttt atggatatag aggtaaacat   180
ttgggtggat caaggaaacc ggacggagca atttatactg tcggatctcc tattgattac   240
ggtgtgatcg tggatactaa agcttatagc ggaggttata atctgccaat tggccaagca   300
gatgaaatgc aacgatatgt cgaagaaaat caaacacgaa acaaacatat caaccctaat   360
gaatggtgga agtctatcc atcttctgta acggaattta gttttttatt tgtgagtggt   420
cactttaaag gaaactacaa agctcagctt acacgattaa atcatatcac taattgtaat   480
ggagctgttc ttagtgtaga agagcttta attggtggag aaatgattaa agccggcaca   540
ttaaccttag aggaagtcag acggaaattt aataacggcg agataaactt tagatct      597
```

<210> SEQ ID NO 15
<211> LENGTH: 21
<212> TYPE: DNA
<213> ORGANISM: HUMAN

<400> SEQUENCE: 15

```
cccaagaaga agaggaaggt g                                              21
```

<210> SEQ ID NO 16
<211> LENGTH: 7
<212> TYPE: PRT
<213> ORGANISM: HUMAN

<400> SEQUENCE: 16

```
Pro Lys Lys Lys Arg Lys Val
1               5
```

```
<210> SEQ ID NO 17
<211> LENGTH: 69
<212> TYPE: DNA
<213> ORGANISM: HUMAN

<400> SEQUENCE: 17
atggactaca aagaccatga cggtgattat aaagatcatg acatcgatta caaggatgac      60
gatgacaag                                                             69

<210> SEQ ID NO 18
<211> LENGTH: 23
<212> TYPE: PRT
<213> ORGANISM: HUMAN

<400> SEQUENCE: 18

Met Asp Tyr Lys Asp His Asp Gly Asp Tyr Lys Asp His Asp Ile Asp
1               5                   10                  15

Tyr Lys Asp Asp Asp Asp Lys
            20

<210> SEQ ID NO 19
<211> LENGTH: 49
<212> TYPE: DNA
<213> ORGANISM: HUMAN

<400> SEQUENCE: 19
cttacccttc tcccatttcc tcatccttcc aacataaata tattttggg                 49

<210> SEQ ID NO 20
<211> LENGTH: 20
<212> TYPE: DNA
<213> ORGANISM: HUMAN

<400> SEQUENCE: 20
ctgccgtctc tctcctgagt                                                 20

<210> SEQ ID NO 21
<211> LENGTH: 20
<212> TYPE: DNA
<213> ORGANISM: HUMAN

<400> SEQUENCE: 21
gtgggcttgt actcggtcat                                                 20
```

ENGINEERING NEURAL STEM CELLS USING HOMOLOGOUS RECOMBINATION

CROSS REFERENCE TO RELATED APPLICATION(S)

This patent application is the U.S. National Stage of PCT/US2014/065769, filed Nov. 14, 2014, which claims the benefit of priority from U.S. Provisional Application No. 61/904,999, filed Nov. 15, 2013, and U.S. Provisional Application No. 61/905,002, filed Nov. 15, 2013, which are both each incorporated by reference in their entireties herein.

FIELD OF THE DISCLOSURE

This application relates to the field of engineered human stem cells. Further, this related to the field of neuronal stem cells, specifically to methods for modifying the genome of neuronal stem cells.

BACKGROUND

Safe-harbor loci, which allow for robust expression of a transgene integrated into the genome of a cell, provide a defined insertion cite for large exogenous DNA such as mini-gene and reporter cassettes. For example, PPP1R12C/AAVS1 and hRosa26 safe harbors have been used in genome engineering of human pluripotent stem cells by conventional or nuclease-enhanced gene targeting (Trion, S. et al., Nature biotechnology 25, 1477-1482 (2007) and Zou, J. et al., Blood 117, 5561-5572 (2011)). While Zinc Finger Nuclease (ZFN), transcription activator-like effector nuclease (TALEN), and CRISPR (clustered regularly interspaced short palindromic repeat) RNA-guided Cas nuclease (CRISPR/Cas) have been used to show efficient gene editing in pluripotent stem cells (Hockemeyer, D. et al., Nature biotechnology 29, 731-734 (2011); Mali, P. et al., Science 339, 823-826 (2013); Zou, J. et al., Cell Stem Cell 5, 97-110 (2009)), one-step modification of multiple loci in stem cells was only recently demonstrated in mouse embryonic stem cells (ESCs) and embryos by non-homologous end-joining (NHEJ) or homology-directed repair (HDR) (Wang, H. et al., Cell 153, 910-918 (2013) and Yang, H. et al., Cell 154, 1370-1379 (2013)). To date, multiplexed knock-in or transfer of large DNA fragment has not been reported in human pluripotent or multi-potent stem cells, although such engineered human stem cells are highly valuable for multi-lineage labeling, drug-screening, and gene therapy.

Neural stem cells (NSCs) are multipotent, self-renewing cells found in the central nervous system (CNS), capable of differentiating into neurons and glia. NSCs can be obtained from several sources; allogeneic sources include fetal tissue, cadaveric samples, while autologous sources can come from brain biopsies or differentiated induced pluripotent cells (iPSCs). Due to the obtainability of NSCs from fetal tissue, adult brain biopsies, cadavers, and iPSCs, genomic engineering of NSCs will greatly enhance their versatility in therapeutic application.

Neurons in the central and peripheral nervous systems degenerate as part of the normal function of human development and aging. Pathological neuron degeneration, however, is a serious condition seen in several neurological disorders. Neuronal degeneration can be specific or diffuse, and can lead to sensory, motor and cognitive impairments. Neurodegenerative disorders encompass a range of seriously debilitating conditions including Parkinson's disease, amyotrophic lateral sclerosis (ALS, "Lou Gehrig's disease"), multiple sclerosis, Huntington's disease, Alzheimer's disease, Pantothenate kinase associated neurodegeneration (PKAN, formerly Hallervorden-Spatz syndrome), multiple system atrophy, diabetic retinopathy, multi-infarct dementia, macular degeneration, and the like. These conditions are characterized by a gradual but relentless worsening of the patient's condition over time. These disorders affect a large population of humans, especially older adults. Nevertheless, there are limited treatment options for these disorders.

Several strategies are being pursued to develop therapies for neurodegenerative disorders, including Parkinson's disease. For Parkinson's disease, the techniques range from the use of dopaminotrophic factors (Takayama et al., Nature Med. 1:53-58, 1995) and viral vectors (Choi-Lundberg et al., Science 275:838-841, 1997) to the transplantation of primary xenogeneic tissue (Deacon et al., Nature Med. 3:350-353, 1997). Transplantation of dopaminergic neurons is a clinically promising experimental treatment in late stage Parkinson's disease. More than 200 patients have been transplanted worldwide (Olanow et al., Trends Neurosci. 19:102-109, 1996), and clinical improvement has been confirmed (Olanow et al., supra, and Wenning et al., Ann. Neurol. 42:95-107, 1997) and was correlated to good graft survival and innervation of the host striatum (Kordower et al., N. Engl. J. Med. 332:1118-1124, 1995). However, fetal nigral transplantation therapy generally requires human fetal tissue from at least 3-5 embryos to obtain a clinically reliable improvement in the patient. A different source of these neurons is clearly needed.

SUMMARY OF THE DISCLOSURE

Described herein are recombinant polynucleotide-binding polypeptides, recombinant fusion proteins made with the described polynucleotide-binding polypeptides, methods of using the described recombinant polynucleotide-binding polypeptides and recombinant fusion proteins to modify genomic DNA of cells and, in some embodiments, create recombinant cells.

The recombinant polynucleotide-binding polypeptides described herein can occur in a variety of forms. In some embodiments the recombinant polynucleotide-binding polypeptide is a recombinant DNA-binding polypeptide that specifically binds to a genomic target sequence of a subject. In one embodiment the targeted genomic sequence bound by the recombinant DNA-binding polypeptide falls within the sequence of SEQ ID NO: 19, or its corresponding antisense sequence. In some embodiments the described recombinant DNA-binding polypeptide is a zinc-finger domain or a transcription activator-like effector (TALE) domain, or a polypeptide fragment thereof. Furthermore, the described recombinant DNA-binding polypeptide may also be combined with a polypeptide having nuclease activity, such as a zinc-finger domain or a transcription activator-like effector (TALE) domain fused to a nuclease protein, or a fragment thereof. In some embodiments the polypeptide having nuclease activity that is fused with the recombinant DNA-binding polypeptide is the fokI nuclease, or a derivative or fragment thereof. In the case of a recombinant DNA-binding polypeptide produced from a TALE domain, fusion with a polypeptide having nuclease activity forms a transcription activator-like effector nuclease (TALEN). Some of the TALEN embodiments described herein are designed to specifically target a genomic sequence that falls within the sequence of SEQ ID NO: 19, or its corresponding antisense sequence, such as, for example, the sequence of SEQ ID NO: 1 or 3.

Provided herein are donor polynucleotides that may be inserted into the genome of a cell. In some embodiments the donor polynucleotides are a double-stranded polynucleotide with sense and/or antisense strand polynucleotide overhangs that are at least partially complementary to corresponding polynucleotide overhangs of cleaved genomic DNA to facilitate insertion of the donor polynucleotide with the cleaved genomic DNA. In some embodiments the donor polynucleotide may express a polypeptide once inserted into the genome. In some embodiments the polypeptide can be a protein that can function to induce cell differentiation or maturation to proceed in a particular manner, such as toward a specific lineage. In some embodiments the expression of a polypeptide by the donor polynucleotide may be controlled by an inducible promoter. In other embodiments, the expression of a polypeptide by the donor polynucleotide may be controlled by a repressible promoter. In still other embodiments the donor polynucleotide may encode more than one polypeptide, for example, the donor polynucleotide may include an expression cassette having a plurality of genes. In certain embodiments in which the donor polynucleotide encodes more than one polypeptide, the donor polynucleotide may have inducible promoters to regulate the expression of certain genes and repressible promoters to regulate the expression of other genes. Particular loci of interest for inserting a polynucleotide into the genome of a cell are safe harbor loci, as described herein.

Also described herein are vectors that may encode the recombinant DNA-binding polypeptides, zinc-finger or TALE domains, nuclease proteins or polypeptides, fusion proteins produced from the fusion of DNA-binding polypeptides and nuclease proteins or polypeptides, and TALENs. In some embodiments the expression of the polypeptides encoded by the vectors is controlled by an inducible promoter. In other embodiments the expression of the polypeptides encoded by the vectors is controlled by a repressible promoter. Recombinant cells modified by the described vectors, for example transfected cells or cells having an expression product of the vectors, are also described herein.

Kits incorporating the recombinant polynucleotides described herein are also described. These kits may further include one or more of a transfection reagent, a nucleofection reagent, a selection agent, or instructions for using the kit.

Described herein are methods of using the described polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs. One application for use with some of the compositions described herein is a method of modifying the genomic DNA of a cell by introducing into the cell a first TALEN with a DNA-binding domain specific for a DNA sequence upstream of a genomic sequence of interest and a second TALEN with a DNA-binding domain specific for a DNA sequence downstream from the genomic sequence of interest, whereby the TALEN cleaves the genomic DNA and excises the genomic sequence of interest, thereby modifying the genomic DNA of the cell.

Also described are methods for inserting a polynucleotide into the genome of a cell by introducing into the cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

An induced pluripotent stem cell may also be produced from a somatic cell using the methods and compositions described herein. One such method involves introducing into a somatic cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Additional methods provided herein can be used to induce an iPS cell to differentiate to a lineage-specific cell by introducing into an iPS cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, having sense and/or antisense strand polynucleotide overhangs that are complementary to corresponding polynucleotide overhangs of genomic DNA at the genomic insertion site cleaved by the introduced TALENs, wherein said complementary overhangs facilitate insertion of the donor polynucleotide into the genome of the cell, whereupon expression of the integrated polynucleotide causes the iPS cell to differentiate into a specific cell lineage.

Methods of treating a disease condition in a subject are also described herein. In one embodiment the method is carried out by expressing in a cell present in the subject a donor polynucleotide encoding one or more products capable of improving the disease condition. For example, the method may be carried out by introducing into the cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide encoding one or more products sufficient to improve the disease condition, having sense and/or antisense strand polynucleotide overhangs that are complementary to corresponding polynucleotide overhangs of genomic DNA at the genomic insertion site cleaved by the introduced TALENs, wherein complementary overhangs facilitate insertion of the donor polynucleotide into the genome of the cell, wherein the donor polynucleotide is inserted into the genomic insertion site and the disease condition improves following expression of the inserted donor polynucleotide.

Also described herein are methods of assessing the physiological effect of one or more polypeptides of interest on a cell. In one embodiment the method involves introducing into the cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide encoding one or more products of interest, having sense and/or antisense strand polynucleotide overhangs that are complementary to corresponding polynucleotide overhangs of cleaved genomic DNA at the genomic insertion site, wherein the complementary overhangs facilitate insertion of the donor polynucleotide into genomic DNA cleaved by the introduced TALENs, whereby the donor polynucleotide is inserted into the genomic insertion site and one or more parameters of physiology is assessed following expression of the inserted donor polynucleotide.

The polynucleotides, polypeptides, constructs, vectors, and related methods of use are more fully discussed herein.

In some embodiments, methods are provided for modifying the genome of a NSC. Methods are also provided for differentiating a NSC. Methods are also provided for treating a subject that include administering an effective amount of NSCs produced by the methods disclosed herein or cells differentiated from an NSC produced by the methods disclosed herein.

In one embodiment, a method is provided for introducing a polynucleotide of interest into a safe harbor locus in a genome of a NSC. The method includes introducing into the NSC (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, thereby introducing the polynucleotide into the genome of the NSC.

In an additional embodiment, a method is provided for inducing a NSC to differentiate to a neuronal or glial cell. The method includes introducing into the neuronal stem cell (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the NSC, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, thereby introducing the donor polynucleotide into the genome of the NSC. The donor polynucleotide encodes one or more factor sufficient to differentiate the NSC into the neuronal or glial cell.

In another embodiment, a method is provided for treating a neurodegenerative disorder, stroke or a nerve injury in a subject. The method includes selecting a subject with a neurodegenerative disorder or a spinal cord injury and generating a NSC producing a polypeptide of interest. The neuronal stem cell is obtained by introducing into the neuronal stem cell (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and optionally (c) a single or double-stranded donor polynucleotide comprising sense and/or antisense strand polynucleotide overhangs that are complementary to corresponding polynucleotide overhangs of cleaved the genomic DNA when cleaved at the genomic insertion site, wherein the complementary overhangs facilitate homologous recombination of the donor polynucleotide with the cleaved genomic DNA, thereby introducing the donor polynucleotide into the genome of the NSC. A therapeutically effective amount of the NSC, or one or more cells differentiated from the NSC, can be administered to the subject, thereby treating the neurodegenerative disease, stroke or the spinal cord injury in the subject.

In a further embodiment, a method is provided for modifying the genomic DNA of a NSC. The method includes introducing into the cell (a) an upstream transcription activator-like effector nuclease (TALEN) comprising an upstream DNA-binding domain linked to a DNA cleavage domain, wherein the upstream DNA binding domain specifically binds to a site upstream of a genomic sequence of interest, and (b) a downstream transcription activator-like effector nuclease (TALEN) comprising a downstream DNA-binding domain linked to a DNA cleavage domain. The downstream DNA binding domain specifically binds to a site downstream of a genomic sequence of interest, and the transcription activator-like effector nucleases cleave the genomic DNA and excise the genomic sequence of interest, thereby modifying the genomic DNA of the NSC.

In another embodiment, a method is provided for treating a disorder, such as a disease resulting from dominant mutations. The method includes selecting a subject with a neurodegenerative disorder or a spinal cord injury and generating a NSC producing a polypeptide of interest. The neuronal stem cell is obtained by introducing into the cell (a) an upstream transcription activator-like effector nuclease (TALEN) comprising an upstream DNA-binding domain linked to a DNA cleavage domain, wherein the upstream DNA binding domain specifically binds to a site upstream of a genomic sequence of interest, and (b) a downstream transcription activator-like effector nuclease (TALEN) comprising a downstream DNA-binding domain linked to a DNA cleavage domain. The downstream DNA binding domain specifically binds to a site downstream of a genomic sequence of interest, and the transcription activator-like effector nucleases cleave the genomic DNA and excise the genomic sequence of interest, thereby modifying the genomic DNA of the NSC.

The foregoing and other features and advantages of the invention will become more apparent from the following detailed description of a several embodiments which proceeds with reference to the accompanying figures.

BRIEF DESCRIPTION OF THE FIGURES

FIGS. 2A-2H. Single and mulitplexed safe harbor reporter knock-in in human neural stem cells. (A) Southern analysis of Nanoluc-HaloTag (iCLHN) or tdTomato (iCAGTom) targeted NCRM1NSC or H9NSC at AAVS1 or CLYBL locus. iPSCs with single TI of iCLHN at AAVS1 allele were used as control. AAVS1 or CLYBL probes were used to detect integrations at each safe harbor as shown in FIG. 1. Compared to the control, NCRM1NSC-AS1-iCLHN shows total loss of wild-type band (WT) indicating all the cells in the polyclonal NSCs have biallelic TI at AAVS1 locus. Asterisk indicates additional RI. NCRM1NSCs or H9NSCs targeted by iCAGTom at AAVS1 (AS1), and H9NSCs targeted by iCAGTom at CLYBL (C13) mostly have 1 TI allele and 1 WT allele, with a small fraction containing additional 1-2 RI. (B) Bright field (BF), fluorescence (Oregon green stained HaloTag) and luminescence (pseudocolored Nanoluc) imaging of NCRM1NSC-AS1-iCLHN showed ~100% targeted NSCs express Nanoluc-HaloTag. (C) Normal karyotype of safe harbor targeted NCRM1NSC-AS1-iCLHN. (D) NCRM1NSC-AS1-iCLHN differentiation into Tuj1+ neurons and GFAP+ astrocyte. (E) Clones of dual safe harbor targeted NSCs, NCRM1NSC-AS1Tom-C13GFP, were confirmed by Southern. Asterisk indicates additional RI. (F-G) Fluorescent images of undifferentiated (F) and differentiated (G) NCRM1NSC-AS1Tom-C13GFP clone. MAP2+ committed neurons show persistent tdTomato and copGFP expression. Nuclei are stained by DAPI. Scale bar=400 μm. (H) Dendrogram of non-targeted and safe harbor targeted iPSCs and NSCs based on microarray analysis. The X-axis represents $1-R^2$ (correlation co-efficiency).

FIGS. 6A-6C. CLYBL TALEN target sequence and efficiency. CLYBL TALEN target sequence and efficiency. (A) Sequence of CLYBL TALEN target site at intron 2 of CLYBL. Bold fonts indicate TALEN binding sequence. (B) Capillary electrophoresis plot from T7E1 assay indicates CLYBL TALENs have ~25% NHEJ efficiency. (C) CLYBL TALEN activity estimated by direct NHEJ mutation sequencing confirmed 25% (12 alleles out of 48) efficiency. Bold fonts show the location of TALEN binding sequences SEQ ID NO: 1 (upstream sequence) and the complement of SEQ ID NO: 3 (downstream sequence).

FIGS. 8A-8F. Characterizations of CLYBL targeted iPSCs. (A) Comparison of HaloTag expression between AAVS1 (AS1) and CLYBL (C13) targeted NCRM5 (NL5) clones using Oregon green (OG) ligand. Y-axis=MFI. Error bar=S.E.M. (B) Histogram of HaloTag/OG expression from AAVS1 or CLYBL targeted clones. The latter clones (Wang et al., *Cell* 153, 910-918 (2013); Yang et al., *Cell* 154, 1370-1379 (2013); Bedell et al., *Nature* 491, 114-118 (2012).) have stronger expression than AAVS1 clones (Wang et al., supra; Cermak et al., *Nucleic Acids Res* 39, e82 (2011); Thyagarajan et al., *Stem cells* 26, 119-126 (2008)). NCRM5-C13-iCLHN clone 6 shows normal karyotype (C), pluripotent markers (D), and in vitro differentiation into three germ layers (E). (F) Comparison of iCAGcopGFP expression between CLYBL targeting and AAVS1 targeting, showing the former one is much stronger.

FIG. 9. Co-nucleofection efficiency of two-color targeting donors.

FIG. 15. Construct map for left and right AAVS1 TALENs and AAVS1 donor vector. The features present in the TALEN and donor expression vectors are schematically depicted including promoters and selection cassettes.

SEQUENCE LISTING

Figure 1A:
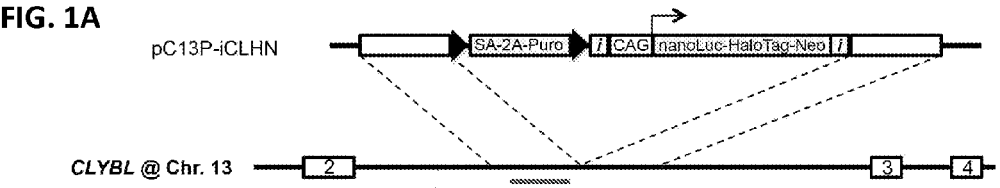
FIGS. 1A-1G. Single and mulitplexed safe harbor reporter knock-in in human iPSCs. (A) Scheme of gene targeting at CLYBL safe harbor on Chr. 13. The donor shown here has a splicing acceptor (SA)-2A linked puromycin for selection. An insulator (i) flanked CAG-derived Nanoluc-HaloTag fusion protein (iCLHN) is targeted into intron 2 of CLYBL. Black triangles indicate loxP sites. Red bar shows probe used to identify integrations (TI and RI). (B) Southern blot of CLYBL targeted human iPSC clones. Wild-type NCRM5 was used as control "C" to identify wild-type (WT) allele. Green numbers indicated biallelic targeted only (2TI) clones. (C) Oregon green stained human iPSC clones with Nanoluc-HalotTag integrated in AAVS1 (NCRM5-AS1-iCLHN) or CLYBL (NCRM5-C13-iCLHN) safe harbor biallelically without RI. Scale bar=400 μm. (D) Nanoluc activity comparison of biallelically targeted NCRM5-AS1-iCLHN and NCRM5-C13-iCLHN clones. Y-axis is relative luciferase unit (RLU). X-axis is cell number. Data shown are average of 3 repeated measurements of 3 NCRM5-AS1-iCLHN clones, 3 NCRM5-C13-iCLHN clones and 1 parental NCRM5 clone. Error bar=S.E.M. (F) Scheme of multiplexed safe harbor gene addition of CAG-tdTomato in AAVS1 and CAG-copGFP in CLYBL. Black, white and grey triangles indicate loxP, lox2272 and lox511, respectively. Red bars show probes used to identify TI and RI (F) Southern blot of dual safe harbor targeted iPSC clones. Top and bottom panels are results from AAVS1 and CLYBL probes, respectively. Green numbers indicated clones with all four alleles targeted. (G) Phase and fluorescent image of dual safe harbor targeted iPSC clone #1. Red=tdTomato (third panel from left), Green=copGFP (second panel from left). Merged image (right panel) is from both fluorescent channels plus phase-contrast image.

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [92044-03_Sequence.txt, Nov. 13, 2014, 49.1 KB], which is incorporated by reference herein.

| SEQ ID NO: | Sequence name | Sequence |
|---|---|---|
| 1 | Upstream CLYBL target | CTTACCCTTCTCCCATT |
| 2 | Upstream CLYBL TALE binding domain | CTGACCCCGGACCAAGTGGTGG<br>CTATCGCCAGCCACGATGGCGG<br>CAAGCAAGCGCTCGAAACGGTG<br>CAGCGGCTGTTGCCGGTGCTGT<br>GCCAGGACCATGGCCTGACCCC<br>GGACCAAGTGGTGGCTATCGCC<br>AGCAACGGTGGCGGCAAGCAAG<br>CGCTCGAAACGGTGCAGCGGCT<br>GTTGCCGGTGCTGTGCCAGGAC<br>CATGGCCTGACCCCGGACCAAG<br>TGGTGGCTATCGCCAGCAACGG<br>TGGCGGCAAGCAAGCGCTCGAA<br>ACGGTGCAGCGGCTGTTGCCGG<br>TGCTGTGCCAGGACCATGGCCT<br>GACCCCGGACCAAGTGGTGGCT<br>ATCGCCAGCAACATTGGCGGCA<br>AGCAAGCGCTCGAAACGGTGCA<br>GCGGCTGTTGCCGGTGCTGTGC<br>CAGGACCATGGCCTGACTCCGG<br>ACCAAGTGGTGGCTATCGCCAG<br>CCACGATGGCGGCAAGCAAGCG<br>CTCGAAACGGTGCAGCGGCTGT<br>TGCCGGTGCTGTGCCAGGACCA<br>TGGCCTGACTCCGGACCAAGTG<br>GTGGCTATCGCCAGCCACGATG<br>GCGGCAAGCAAGCGCTCGAAAC<br>GGTGCAGCGGCTGTTGCCGGTG<br>CTGTGCCAGGACCATGGCCTGA<br>CTCCGGACCAAGTGGTGGCTAT<br>CGCCAGCCACGATGGCGGCAAG<br>CAAGCGCTCGAAACGGTGCAGC<br>GGCTGTTGCCGGTGCTGTGCCA<br>GGACCATGGCCTGACCCCGGAC<br>CAAGTGGTGGCTATCGCCAGCA<br>ACGGTGGCGGCAAGCAAGCGCT<br>CGAAACGGTGCAGCGGCTGTTG<br>CCGGTGCTGTGCCAGGACCATG<br>GCCTGACCCCGGACCAAGTGGT<br>GGCTATCGCCAGCAACGGTGGC<br>GGCAAGCAAGCGCTCGAAACGG<br>TGCAGCGGCTGTTGCCGGTGCT<br>GTGCCAGGACCATGGCCTGACT<br>CCGGACCAAGTGGTGGCTATCG<br>CCAGCCACGATGGCGGCAAGCA<br>AGCGCTCGAAACGGTGCAGCGG<br>CTGTTGCCGGTGCTGTGCCAGG<br>ACCATGGCCTGACCCCGGACCA<br>AGTGGTGGCTATCGCCAGCAAC<br>GGTGGCGGCAAGCAAGCGCTCG<br>AAACGGTGCAGCGGCTGTTGCC<br>GGTGCTGTGCCAGGACCATGGC<br>CTGACTCCGGACCAAGTGGTGG<br>CTATCGCCAGCCACGATGGCGG<br>CAAGCAAGCGCTCGAAACGGTG<br>CAGCGGCTGTTGCCGGTGCTGT<br>GCCAGGACCATGGCCTGACTCC<br>GGACCAAGTGGTGGCTATCGCC<br>AGCCACGATGGCGGCAAGCAAG<br>CGCTCGAAACGGTGCAGCGGCT<br>GTTGCCGGTGCTGTGCCAGGAC<br>CATGGCCTGACTCCGGACCAAG<br>TGGTGGCTATCGCCAGCCACGA<br>TGGCGGCAAGCAAGCGCTCGAA<br>ACGGTGCAGCGGCTGTTGCCGG<br>TGCTGTGCCAGGACCATGGCCT<br>GACCCCGGACCAAGTGGTGGCT<br>ATCGCCAGCAACATTGGCGGCA<br>AGCAAGCGCTCGAAACGGTGCA<br>GCGGCTGTTGCCGGTGCTGTGC<br>CAGGACCATGGCCTGACCCCGG<br>ACCAAGTGGTGGCTATCGCCAG<br>CAACGGTGGCGGCAAGCAAGCG<br>CTCGAAACGGTGCAGCGGCTGT<br>TGCCGGTGCTGTGCCAGGACCA |

| SEQ ID NO: | Sequence name | Sequence |
|---|---|---|
| | | TGGCCTGACCCCGGACCAAGTG |
| | | GTGGCTATCGCCAGCAACGGTG |
| | | GCGGCAAGCAAGCGCTCGAA |
| 3 | Downstream CLYBL target | CCCAAAATATATTTAT (Note that this is shown in a 5' to 3' (sense) orientation.) |
| 4 | Downstream CLYBL TALE binding domain | CTGACCCCGGACCAAGTGGTGG CTATCGCCAGCCACGATGGCGG CAAGCAAGCGCTCGAAACGGTG CAGCGGCTGTTGCCGGTGCTGT GCCAGGACCATGGCCTGACTCC GGACCAAGTGGTGGCTATCGCC AGCCACGATGGCGGCAAGCAAG CGCTCGAAACGGTGCAGCGGCT GTTGCCGGTGCTGTGCCAGGAC CATGGCCTGACTCCGGACCAAG TGGTGGCTATCGCCAGCCACGA TGGCGGCAAGCAAGCGCTCGAA ACGGTGCAGCGGCTGTTGCCGG TGCTGTGCCAGGACCATGGCCT GACCCCGGACCAAGTGGTGGCT ATCGCCAGCAACATTGGCGGCA AGCAAGCGCTCGAAACGGTGCA GCGGCTGTTGCCGGTGCTGTGC CAGGACCATGGCCTGACCCCGG ACCAAGTGGTGGCTATCGCCAG CAACATTGGCGGCAAGCAAGCG CTCGAAACGGTGCAGCGGCTGT TGCCGGTGCTGTGCCAGGACCA TGGCCTGACCCCGGACCAAGTG GTGGCTATCGCCAGCAACGGTG GCGGCAAGCAAGCGCTCGAAAC GGTGCAGCGGCTGTTGCCGGTG CTGTGCCAGGACCATGGCCTGA CCCCGGACCAAGTGGTGGCTAT CGCCAGCAACATTGGCGGCAAG CAAGCGCTCGAAACGGTGCAGC GGCTGTTGCCGGTGCTGTGCCA GGACCATGGCCTGACCCCGGAC CAAGTGGTGGCTATCGCCAGCA ACGGTGGCGGCAAGCAAGCGCT CGAAACGGTGCAGCGGCTGTTG CCGGTGCTGTGCCAGGACCATG GCCTGACTCCGGACCAAGTGGT GGCTATCGCCAGCAACATTGGC GGCAAGCAAGCGCTCGAAACGG TGCAGCGGCTGTTGCCGGTGCT GTGCCAGGACCATGGCCTGACC CCGGACCAAGTGGTGGCTATCG CCAGCAACGGTGGCGGCAAGCA AGCGCTCGAAACGGTGCAGCGG CTGTTGCCGGTGCTGTGCCAGG ACCATGGCCTGACCCCGGACCA AGTGGTGGCTATCGCCAGCAAC ATTGGCGGCAAGCAAGCGCTCG AAACGGTGCAGCGGCTGTTGCC GGTGCTGTGCCAGGACCATGGC CTGACCCCGGACCAAGTGGTGG CTATCGCCAGCAACGGTGGCGG CAAGCAAGCGCTCGAAACGGTG CAGCGGCTGTTGCCGGTGCTGT GCCAGGACCATGGCCTGACCCC GGACCAAGTGGTGGCTATCGCC AGCAACGGTGGCGGCAAGCAAG CGCTCGAAACGGTGCAGCGGCT GTTGCCGGTGCTGTGCCAGGAC CATGGCCTGACCCCGGACCAAG TGGTGGCTATCGCCAGCAACGG TGGCGGCAAGCAAGCGCTCGAA ACGGTGCAGCGGCTGTTGCCGG TGCTGTGCCAGGACCATGGCCT GACCCCGGACCAAGTGGTGGCT ATCGCCAGCAACATTGGCGGCA AGCAAGCGCTCGAAACGGTGCA GCGGCTGTTGCCGGTGCTGTGC CAGGACCATGGCCTGACCCCGG ACCAAGTGGTGGCTATCGCCAG CAACGGTGGCGGCAAGCAAGCG CTCGAA |
| 5 | Upstream TALEN Includes Δ152 N-terminus and +63 C-terminus | GTGGACTTGAGGACACTCGGTT ATTCGCAACAGCAACAGGAGAA AATCAAGCCTAAGGTCAGGAGC ACCGTCGCGCAACACCACGAGG CGCTTGTGGGGCATGGCTTCAC TCATGCGCATATTGTCGCGCTT TCACAGCACCCTGCGGCGCTTG GGACGGTGGCTGTCAAATACCA AGATATGATTGCGGCCCTGCCC GAAGCCACGCACGAGGCAATTG TAGGGGTCGGTAAACAGTGGTC GGGGAGCGCGAGCACTTGAGGCC TTGCTGACTGTGGCGGGTGAGC TTAGGGGCCTCCGCTCCAGCT CGACACCGGGCAGCTGCTGAAG ATCGCGAAGAGAGGGGGAGTAA CAGCGGTAGAGGCAGTGCACGC CTGGCGCAATGCGCTCACCGGG GCCCCCTGAACCTGACCCCGG ACCAAGTGGTGGCTATCGCCAG CCACGATGGCGGCAAGCAAGCG CTCGAAACGGTGCAGCGGCTGT TGCCGGTGCTGTGCCAGGACCA TGGCCTGACCCCGGACCAAGTG GTGGCTATCGCCAGCAACGGTG GCGGCAAGCAAGCGCTCGAAAC GGTGCAGCGGCTGTTGCCGGTG CTGTGCCAGGACCATGGCCTGA CCCCGGACCAAGTGGTGGCTAT CGCCAGCAACGGTGGCGGCAAG CAAGCGCTCGAAACGGTGCAGC GGCTGTTGCCGGTGCTGTGCCA GGACCATGGCCTGACCCCGGAC CAAGTGGTGGCTATCGCCAGCA ACATTGGCGGCAAGCAAGCGCT CGAAACGGTGCAGCGGCTGTTG CCGGTGCTGTGCCAGGACCATG GCCTGACTCCGGACCAAGTGGT GGCTATCGCCAGCCACGATGGC GGCAAGCAAGCGCTCGAAACGG TGCAGCGGCTGTTGCCGGTGCT GTGCCAGGACCATGGCCTGACT CCGGACCAAGTGGTGGCTATCG CCAGCCACGATGGCGGCAAGCA AGCGCTCGAAACGGTGCAGCGG CTGTTGCCGGTGCTGTGCCAGG ACCATGGCCTGACTCCGGACCA AGTGGTGGCTATCGCCAGCCAC GATGGCGGCAAGCAAGCGCTCG AAACGGTGCAGCGGCTGTTGCC GGTGCTGTGCCAGGACCATGGC CTGACCCCGGACCAAGTGGTGG CTATCGCCAGCAACGGTGGCGG CAAGCAAGCGCTCGAAACGGTG CAGCGGCTGTTGCCGGTGCTGT GCCAGGACCATGGCCTGACCCC GGACCAAGTGGTGGCTATCGCC AGCAACGGTGGCGGCAAGCAAG CGCTCGAAACGGTGCAGCGGCT GTTGCCGGTGCTGTGCCAGGAC CATGGCCTGACTCCGGACCAAG TGGTGGCTATCGCCAGCCACGA TGGCGGCAAGCAAGCGCTCGAA ACGGTGCAGCGGCTGTTGCCGG TGCTGTGCCAGGACCATGGCCT GACCCCGGACCAAGTGGTGGCT ATCGCCAGCAACGGTGGCGGCA AGCAAGCGCTCGAAACGGTGCA GCGGCTGTTGCCGGTGCTGTGC |

| SEQ ID NO: | Sequence name | Sequence |
|---|---|---|
| | | CAGGACCATGGCCTGACTCCGG |
| | | ACCAAGTGGTGGCTATCGCCAG |
| | | CCACGATGGCGGCAAGCAAGCG |
| | | CTCGAAACGGTGCAGCGGCTGT |
| | | TGCCGGTGCTGTGCCAGGACCA |
| | | TGGCCTGACTCCGGACCAAGTG |
| | | GTGGCTATCGCCAGCCACGATG |
| | | GCGGCAAGCAAGCGCTCGAAAC |
| | | GGTGCAGCGGCTGTTGCCGGTG |
| | | CTGTGCCAGGACCATGGCCTGA |
| | | CTCCGGACCAAGTGGTGGCTAT |
| | | CGCCAGCCACGATGGCGGCAAG |
| | | CAAGCGCTCGAAACGGTGCAGC |
| | | GGCTGTTGCCGGTGCTGTGCCA |
| | | GGACCATGGCCTGACCCCGGAC |
| | | CAAGTGGTGGCTATCGCCAGCA |
| | | ACATTGGCGGCAAGCAAGCGCT |
| | | CGAAACGGTGCAGCGGCTGTTG |
| | | CCGGTGCTGTGCCAGGACCATG |
| | | GCCTGACCCCGGACCAAGTGGT |
| | | GGCTATCGCCAGCAACGGTGGC |
| | | GGCAAGCAAGCGCTCGAAACGG |
| | | TGCAGCGGCTGTTGCCGGTGCT |
| | | GTGCCAGGACCATGGCCTGACC |
| | | CCGGACCAAGTGGTGGCTATCG |
| | | CCAGCAACGGTGGCGGCAAGCA |
| | | AGCGCTCGAAAGCATTGTGCC |
| | | CAGCTGAGCCGGCCTGATCCGG |
| | | CGTTGGCCGCGTTGACCAACGA |
| | | CCATCTGGTGGCGTTGGCATGT |
| | | CTTGGTGGACGTCCCGCGCTCG |
| | | ATGCAGTCAAAAAGGGTCTGCC |
| | | TCATGCTCCCGCATTGATCAAA |
| | | AGAACCAACCGGCGGATTCCCG |
| | | AGAGAACTTCCCATCGAGTCGC |
| | | GGGATCCCAACTAGTCAAAAGT |
| | | GAACTGGAGGAGAAGAAATCTG |
| | | AACTTCGTCATAAAATTGAAATA |
| | | TGTGCCTCATGAATATATTGAA |
| | | TTAATTGAAATTGCCAGAAATT |
| | | CCACTCAGGATAGAATTCTTGA |
| | | AATGAAGGTAATGGAATTTTTT |
| | | ATGAAAGTTTATGGATATAGAG |
| | | GTAAACATTTGGGTGGATCAAG |
| | | GAAACCGGACGGAGCAATTTAT |
| | | ACTGTCGGATCTCCTATTGATT |
| | | ACGGTGTGATCGTGGATACTAA |
| | | AGCTTATAGCGGAGGTTATAAT |
| | | CTGCCAATTGGCCAAGCAGATG |
| | | AAATGCAACGATATGTCGAAGA |
| | | AAATCAAACACGAAACAAACAT |
| | | ATCAACCCTAATGAATGGTGGA |
| | | AAGTCTATCCATCTTCTGTAAC |
| | | GGAATTTAAGTTTTTATTTGTG |
| | | AGTGGTCACTTTAAAGGAAACT |
| | | ACAAAGCTCAGCTTACACGATT |
| | | AAATCATATCACTAATTGTAAT |
| | | GGAGCTGTTCTTAGTGTAGAAG |
| | | AGCTTTTAATTGGTGGAGAAAT |
| | | GATTAAAGCCGGCACATTAACC |
| | | TTAGAGGAAGTCAGACGGAAAT |
| | | TTAATAACGGCGAGATAAACTT |
| | | TAGATCT |
| 6 | Downstream TALEN Includes Δ152 N-terminus and +63 C-terminus | GTGGACTTGAGGACACTCGGTT |
| | | ATTCGCAACAGCAACAGGAGAA |
| | | AATCAAGCCTAAGGTCAGGAGC |
| | | ACCGTCGCGCAACACCACGAGG |
| | | CGCTTGTGGGCATGGCTTCAC |
| | | TCATGCGCATATTGTCGCGCTT |
| | | TCACAGCACCCTGCGGCGCTTG |
| | | GGACGGTGGCTGTCAAATACCA |
| | | AGATATGATTGCGGCCCTGCCC |
| | | GAAGCCACGCACGAGGCAATTG |
| | | TAGGGGTCGGTAAACAGTGGTC |
| | | GGGAGCGCGAGCACTTGAGGCC |
| | | TTGCTGACTGTGGCGGGTGAGC |
| | | TTAGGGGGCCTCCGCTCCAGCT |
| | | CGACACCGGGCAGCTGCTGAAG |
| | | ATCGCGAAGAGAGGGGGAGTAA |
| | | CAGCGGTAGAGGCAGTGCACGC |
| | | CTGGCGCAATGCGCTCACCGGG |
| | | GCCCCCTGAACCTGACCCCGG |
| | | ACCAAGTGGTGGCTATCGCCAG |
| | | CCACGATGGCGGCAAGCAAGCG |
| | | CTCGAAACGGTGCAGCGGCTGT |
| | | TGCCGGTGCTGTGCCAGGACCA |
| | | TGGCCTGACTCCGGACCAAGTG |
| | | GTGGCTATCGCCAGCCACGATG |
| | | GCGGCAAGCAAGCGCTCGAAAC |
| | | GGTGCAGCGGCTGTTGCCGGTG |
| | | CTGTGCCAGGACCATGGCCTGA |
| | | CTCCGGACCAAGTGGTGGCTAT |
| | | CGCCAGCCACGATGGCGGCAAG |
| | | CAAGCGCTCGAAACGGTGCAGC |
| | | GGCTGTTGCCGGTGCTGTGCCA |
| | | GGACCATGGCCTGACCCCGGAC |
| | | CAAGTGGTGGCTATCGCCAGCA |
| | | ACATTGGCGGCAAGCAAGCGCT |
| | | CGAAACGGTGCAGCGGCTGTTG |
| | | CCGGTGCTGTGCCAGGACCATG |
| | | GCCTGACCCCGGACCAAGTGGT |
| | | GGCTATCGCCAGCAACATTGGC |
| | | GGCAAGCAAGCGCTCGAAACGG |
| | | TGCAGCGGCTGTTGCCGGTGCT |
| | | GTGCCAGGACCATGGCCTGACC |
| | | CCGGACCAAGTGGTGGCTATCG |
| | | CCAGCAACATTGGCGGCAAGCA |
| | | AGCGCTCGAAACGGTGCAGCGG |
| | | CTGTTGCCGGTGCTGTGCCAGG |
| | | ACCATGGCCTGACCCCGGACCA |
| | | AGTGGTGGCTATCGCCAGCAAC |
| | | ATTGGCGGCAAGCAAGCGCTCG |
| | | AAACGGTGCAGCGGCTGTTGCC |
| | | GGTGCTGTGCCAGGACCATGGC |
| | | CTGACCCCGGACCAAGTGGTGG |
| | | CTATCGCCAGCAACGGTGGCGG |
| | | CAAGCAAGCGCTCGAAACGGTG |
| | | CAGCGGCTGTTGCCGGTGCTGT |
| | | GCCAGGACCATGGCCTGACCCC |
| | | GGACCAAGTGGTGGCTATCGCC |
| | | AGCAACATTGGCGGCAAGCAAG |
| | | CGCTCGAAACGGTGCAGCGGCT |
| | | GTTGCCGGTGCTGTGCCAGGAC |
| | | CATGGCCTGACCCCGGACCAAG |
| | | TGGTGGCTATCGCCAGCAACGG |
| | | TGGCGGCAAGCAAGCGCTCGAA |
| | | ACGGTGCAGCGGCTGTTGCCGG |
| | | TGCTGTGCCAGGACCATGGCCT |
| | | GACCCCGGACCAAGTGGTGGCT |
| | | ATCGCCAGCAACATTGGCGGCA |
| | | AGCAAGCGCTCGAAACGGTGCA |
| | | GCGGCTGTTGCCGGTGCTGTGC |
| | | CAGGACCATGGCCTGACCCCGG |
| | | ACCAAGTGGTGGCTATCGCCAG |
| | | CAACGGTGGCGGCAAGCAAGCG |
| | | CTCGAAACGGTGCAGCGGCTGT |
| | | TGCCGGTGCTGTGCCAGGACCA |
| | | TGGCCTGACCCCGGACCAAGTG |
| | | GTGGCTATCGCCAGCAACGGTG |
| | | GCGGCAAGCAAGCGCTCGAAAC |
| | | GGTGCAGCGGCTGTTGCCGGTG |
| | | CTGTGCCAGGACCATGGCCTGA |
| | | CCCCGGACCAAGTGGTGGCTAT |
| | | CGCCAGCAACGGTGGCGGCAAG |
| | | CAAGCGCTCGAAACGGTGCAGC |
| | | GGCTGTTGCCGGTGCTGTGCCA |
| | | GGACCATGGCCTGACCCCGGAC |
| | | CAAGTGGTGGCTATCGCCAGCA |
| | | ACATTGGCGGCAAGCAAGCGCT |
| | | CGAAACGGTGCAGCGGCTGTTG |
| | | CCGGTGCTGTGCCAGGACCATG |

| SEQ ID NO: | Sequence name | Sequence |
|---|---|---|
| | | GCCTGACCCCGGACCAAGTGGT |
| | | GGCTATCGCCAGCAACGGTGGC |
| | | GGCAAGCAAGCGCTCGAAAGCA |
| | | TTGTGGCCCAGCTGAGCCGGCC |
| | | TGATCCGGCGTTGGCCGCGTTG |
| | | ACCAACGACCATCTGGTGGCGT |
| | | TGGCATGTCTTGGTGGACGTCC |
| | | CGCGCTCGATGCAGTCAAAAAG |
| | | GGTCTGCCTCATGCTCCCGCAT |
| | | TGATCAAAAGAACCAACCGGCG |
| | | GATTCCCGAGAGAACTTCCCAT |
| | | CGAGTCGCGGGATCCCAACTAG |
| | | TCAAAAGTGAACTGGAGGAGAA |
| | | GAAATCTGAACTTCGTCATAAA |
| | | TTGAAATATGTGCCTCATGAAT |
| | | ATATTGAATTAATTGAAATTGC |
| | | CAGAAATTCCACTCAGGATAGA |
| | | ATTCTTGAAATGAAGGTAATGG |
| | | AATTTTTTATGAAAGTTTATGG |
| | | ATATAGAGGTAAACATTTGGGT |
| | | GGATCAAGGAAACCGGACGGAG |
| | | CAATTTATACTGTCGGATCTCC |
| | | TATTGATTACGGTGTGATCGTG |
| | | GATACTAAAGCTTATAGCGGAG |
| | | GTTATAATCTGCCAATTGGCCA |
| | | AGCAGATGAAATGCAACGTATA |
| | | GTCGAAGAAAATCAAACACGAA |
| | | ACAAACATATCAACCCTAATGA |
| | | ATGGTGGAAAGTCTATCCATCT |
| | | TCTGTAACGGAATTTAAGTTTT |
| | | TATTTGTGAGTGGTCACTTTAA |
| | | AGGAAACTACAAAGCTCAGCTT |
| | | ACACGATTAAATCATATCACTA |
| | | ATTGTAATGGAGCTGTTCTTAG |
| | | TGTAGAAGAGCTTTTAATTGGT |
| | | GGAGAAATGATTAAAGCCGGCA |
| | | CATTAACCTTAGAGGAAGTCAG |
| | | ACGGAAATTTAATAACGGCGAG |
| | | ATAAACTTTAGATCT |
| 7 | Upstream CLYBL TALE binding domain | LTPDQVVAIASHDGGKQALETV QRLLPVLCQDHGLTPDQVVAIA SNGGGKQALETVQRLLPVLCQD HGLTPDQVVAIASNGGGKQALE TVQRLLPVLCQDHGLTPDQVVA IASNIGGKQALETVQRLLPVLC QDHGLTPDQVVAIASHDGGKQA LETVQRLLPVLCQDHGLTPDQV VAIASHDGGKQALETVQRLLPV LCQDHGLTPDQVVAIASHDGGK QALETVQRLLPVLCQDHGLTPD QVVAIASNGGGKQALETVQRLL PVLCQDHGLTPDQVVAIASNGG GKQALETVQRLLPVLCQDHGLT PDQVVAIASHDGGKQALETVQR LLPVLCQDHGLTPDQVVAIASN GGGKQALETVQRLLPVLCQDHG LTPDQVVAIASHDGGKQALETV QRLLPVLCQDHGLTPDQVVAIA SHDGGKQALETVQRLLPVLCQD HGLTPDQVVAIASHDGGKQALE TVQRLLPVLCQDHGLTPDQVVA IASNIGGKQALETVQRLLPVLC QDHGLTPDQVVAIASNGGGKQA LETVQRLLPVLCQDHGLTPDQV VAIASNGGGKQALE |
| 8 | Upstream TALEN Includes Δ152 N-terminus and +63 C-terminus | VDLRTLGYSQQQQEKIKPKVRS TVAQHHEALVGHGFTHAHIVAL SQHPAALGTVAVKYQDMIAALP EATHEAIVGVGKQWSGARALEA LLTVAGELRGPPLQLDTGQLLK IAKRGGVTAVEAVHAWRNALTG APLNLTPDQVVAIASHDGGKQA LETVQRLLPVLCQDHGLTPDQV VAIASNGGGKQALETVQRLLPV LCQDHGLTPDQVVAIASNGGGK QALETVQRLLPVLCQDHGLTPD QVVAIASNIGGKQALETVQRLL PVLCQDHGLTPDQVVAIASHDG GKQALETVQRLLPVLCQDHGLT PDQVVAIASHDGGKQALETVQR LLPVLCQDHGLTPDQVVAIASH DGGKQALETVQRLLPVLCQDHG LTPDQVVAIASNGGGKQALETV QRLLPVLCQDHGLTPDQVVAIA SNGGGKQALETVQRLLPVLCQD HGLTPDQVVAIASHDGGKQALE TVQRLLPVLCQDHGLTPDQVVA IASNGGGKQALETVQRLLPVLC QDHGLTPDQVVAIASHDGGKQA LETVQRLLPVLCQDHGLTPDQV VAIASHDGGKQALETVQRLLPV LCQDHGLTPDQVVAIASHDGGK QALETVQRLLPVLCQDHGLTPD QVVAIASNIGGKQALETVQRLL PVLCQDHGLTPDQVVAIASNGG GKQALETVQRLLPVLCQDHGLT PDQVVAIASNGGGKQALESIVA QLSRPDPALAALTNDHLVALAC LGGRPALDAVKKGLPHAPALIK RTNRRIPERTSHRVAGSQLVKS ELEEKKSELRHKLKYVPHEYIE LIEIARNSTQDRILEMKVMEFF MKVYGYRGKHLGGSRKPDGAIY TVGSPIDYGVIVDTKAYSGGYN LPIGQADEMQRYVEENQTRNKH INPNEWWKVYPSSVTEFKFLFV SGHFKGNYKAQLTRLNHITNCN GAVLSVEELLIGGEMIKAGTLT LEEVRRKFNNGEINFRS |
| 9 | pZT-C13-L | ATGGACTACAAAGACCATGACG GTGATTATAAAGATCATGACAT CGATTACAAGGATGACGATGAC AAGATGGCCCCCAAGAAGAAGA GGAAGGTGGGCATCCACGGGGT ACCTATGGTGGACTTGAGGACA CTCGGTTATTCGCAACAGCAAC AGGAGAAAATCAAGCCTAAGGT CAGGAGCACCGTCGCGCAACAC CACGAGGCGCTTGTGGGCATG GCTTCACTCATGCGCATATTGT CGCGCTTTCACAGCACCCTGCG GCGCTTGGGACGGTGGCTGTCA AATACCAAGATATGATTGCGGC CCTGCCCGAAGCCACGCACGAG GCAATTGTAGGGGTCGGTAAAC AGTGGTCGGGAGCGCGAGCACT TGAGGCCTTGCTGACTGTGGCG GGTGAGCTTAGGGGGCCTCCGC TCCAGCTCGACACCGGGCAGCT GCTGAAGATCGCGAAGAGAGGG GGAGTAACAGCGGTAGAGGCAG TGCACGCCTGGCGCAATGCGCT CACCGGGGCCCCCCTGAACCTG ACCCCGGACCAAGTGGTGGCTA TCGCCAGCCACGATGGCGGCAA GCAAGCGCTCGAAACGGTGCAG CGGCTGTTGCCGGTGCTGTGCC AGGACCATGGCCTGACCCCGGA CCAAGTGGTGGCTATCGCCAGC AACGGTGGCGGCAAGCAAGCGC TCGAAACGGTGCAGCGGCTGTT GCCGGTGCTGTGCCAGGACCAT GGCCTGACCCCGGACCAAGTGG TGGCTATCGCCAGCAACGGTGG CGGCAAGCAAGCGCTCGAAACG GTGCAGCGGCTGTTGCCGGTGC TGTGCCAGGACCATGGCCTGAC CCCGGACCAAGTGGTGGCTATC GCCAGCAACATTGGCGGCAAGC |

| SEQ ID NO: | Sequence name | Sequence |
|---|---|---|
| | | AAGCGCTCGAAACGGTGCAGCG GCTGTTGCCGGTGCTGTGCCAG GACCATGGCCTGACTCCGGACC AAGTGGTGGCTATCGCCAGCCA CGATGGCGGCAAGCAAGCGCTC GAAACGGTGCAGCGGCTGTTGC CGGTGCTGTGCCAGGACCATGG CCTGACTCCGGACCAAGTGGTG GCTATCGCCAGCCACGATGGCG GCAAGCAAGCGCTCGAAACGGT GCAGCGGCTGTTGCCGGTGCTG TGCCAGGACCATGGCCTGACTC CGGACCAAGTGGTGGCTATCGC CAGCCACGATGGCGGCAAGCAA GCGCTCGAAACGGTGCAGCGGC TGTTGCCGGTGCTGTGCCAGGA CCATGGCCTGACCCCGGACCAA GTGGTGGCTATCGCCAGCAACG GTGGCGGCAAGCA

| SEQ ID NO: | Sequence name | Sequence |
|---|---|---|
| | | QVVAIASNIGGKQALETVQRLL PVLCQDHGLTPDQVVAIASNGG GKQALESIVAQLSRPDPALAAL TNDHLVALACLGGRPALDAVKK GLPHAPALIKRTNRRIPERTSH RVAGSQLVKSELEEKKSELRHK LKYVPHEYIELIEIARNSTQDR ILEMKVMEFFMKVYGYRGKHLG GSRKPDGAIYTVGSPIDYGVIV DTKAYSGGYNLPIGQADEMQRY VEENQTRNKHINPNEWWKVYPS SVTEFKFLFVSGHFKGNYKAQL TRLNHITNCNGAVLSVEELLIG GEMIKAGTLTLEEVRRKFNNGE INFRS |
| 12 | pZT-C13-R | ATGGACTACAAAGACCATGACG GTGATTATAAAGATCATGACAT CGATTACAAGGATGACGATGAC AAGATGGCCCCCAAGAAGAAGA GGAAGGTGGGCATCCACGGGGT ACCTATGGTGGACTTGAGGACA CTCGTTATTCGCAACAGCAAC AGGAGAAAATCAAGCCTAAGGT CAGGAGCACCGTCGCGCAACAC CACGAGGCGCTTGTGGGGCATG GCTTCACTCATGCGCATATTGT CGCGCTTTCACAGCACCCTGCG GCGCTTGGGACGGTGGCTGTCA AATACCAAGATATGATTGCGGC CCTGCCCGAAGCCACGCACGAG GCAATTGTAGGGGTCGGTAAAC AGTGGTCGGGAGCGCGAGCACT TGAGGCCTTGCTGACTGTGGCG GGTGAGCTTAGGGGGCCTCCGC TCCAGCTCGACACCGGGCAGCT GCTGAAGATCGCGAAGAGAGGG GGAGTAACAGCGGTAGAGGCAG TGCACGCCTGGCGCAATGCGCT CACCGGGGCCCCCCTGAACCTG ACCCCGGACCAAGTGGTGGCTA TCGCCAGCCACGATGGCGGCAA GCAAGCGCTCGAAACGGTGCAG CGGCTGTTGCCGGTGCTGTGCC AGGACCATGGCCTGACTCCGGA CCAAGTGGTGGCTATCGCCAGC CACGATGGCGGCAAGCAAGCGC TCGAAACGGTGCAGCGGCTGTT GCCGGTGCTGTGCCAGGACCAT GGCCTGACTCCGGACCAAGTGG TGGCTATCGCCAGCCACGATGG CGGCAAGCAAGCGCTCGAAACG GTGCAGCGGCTGTTGCCGGTGC TGTGCCAGGACCATGGCCTGAC CCCGGACCAAGTGGTGGCTATC GCCAGCAACATTGGCGGCAAGC AAGCGCTCGAAACGGTGCAGCG GCTGTTGCCGGTGCTGTGCCAG GACCATGGCCTGACCCCGGACC AAGTGGTGGCTATCGCCAGCAA CATTGGCGGCAAGCAAGCGCTC GAAACGGTGCAGCGGCTGTTGC CGGTGCTGTGCCAGGACCATGG CCTGACCCCGGACCAAGTGGTG GCTATCGCCAGCAACATTGGCG GCAAGCAAGCGCTCGAAACGGT GCAGCGGCTGTTGCCGGTGCTG TGCCAGGACCATGGCCTGACCC CGGACCAAGTGGTGGCTATCGC CAGCAACATTGGCGGCAAGCAA GCGCTCGAAACGGTGCAGCGGC TGTTGCCGGTGCTGTGCCAGGA CCATGGCCTGACCCCGGACCAA GTGGTGGCTATCGCCAGCAACG TGGCGGCAAGCAAGCGCTCGA AACGGTGCAGCGGCTGTTGCCG GTGCTGTGCCAGGACCATGGCC TGACCCCGGACCAAGTGGTGGC TATCGCCAGCAACATTGGCGGC AAGCAAGCGCTCGAAACGGTGC AGCGGCTGTTGCCGGTGCTGTG CCAGGACCATGGCCTGACCCCG GACCAAGTGGTGGCTATCGCCA GCAACGGTGGCGGCAAGCAAGC GCTCGAAACGGTGCAGCGGCTG TTGCCGGTGCTGTGCCAGGACC ATGGCCTGACCCCGGACCAAGT GGTGGCTATCGCCAGCAACATT GGCGGCAAGCAAGCGCTCGAAA CGGTGCAGCGGCTGTTGCCGGT GCTGTGCCAGGACCATGGCCTG ACCCCGGACCAAGTGGTGGCTA TCGCCAGCAACGGTGGCGGCAA GCAAGCGCTCGAAACGGTGCAG CGGCTGTTGCCGGTGCTGTGCC AGGACCATGGCCTGACCCCGGA CCAAGTGGTGGCTATCGCCAGC AACGGTGGCGGCAAGCAAGCGC TCGAAACGGTGCAGCGGCTGTT GCCGGTGCTGTGCCAGGACCAT GGCCTGACCCCGGACCAAGTGG TGGCTATCGCCAGCAACGGTGG CGGCAAGCAAGCGCTCGAAACG GTGCAGCGGCTGTTGCCGGTGC TGTGCCAGGACCATGGCCTGAC CCCGGACCAAGTGGTGGCTATC GCCAGCAACATTGGCGGCAAGC AAGCGCTCGAAACGGTGCAGCG GCTGTTGCCGGTGCTGTGCCAG GACCATGGCCTGACCCCGGACC AAGTGGTGGCTATCGCCAGCAA CGGTGGCGGCAAGCAAGCGCTC GAAAGCATTGTGGCCCAGCTGA GCCGGCCTGATCCGGCGTTGGC CGCGTTGACCAACGACCATCTG GTGGCGTTGGCATGTCTTGGTG GACGTCCCGCGCTCGATGCAGT CAAAAAGGGTCTGCCTCATGCT CCCGCATTGATCAAAAGAACCA ACCGGCGGATTCCCGAGAGAAC TTCCCATCGAGTCGCGGGATCC CAACTAGTCAAAAGTGAACTGG AGGAGAAGAAATCTGAACTTCG TCATAAATTGAAATATGTGCCT CATGAATATATTGAATTAATTG AAATTGCCAGAAATTCCACTCA GGATAGAATTCTTGAAATGAAG GTAATGGAATTTTTTATGAAAG TTTATGGATATAGAGGTAAACA TTTGGGTGGATCAAGGAAACCG GACGGAGCAATTTATACTGTCG GATCTCCTATTGATTACGGTGT GATCGTGGATACTAAAGCTTAT AGCGGAGGTTATAATCTGCCAA TTGGCCAAGCAGATGAAATGCA ACGATATGTCGAAGAAAATCAA ACACGAAACAAACATATCAACC CTAATGAATGGTGGAAAGTCTA TCCATCTTCTGTAACGGAATTT AAGTTTTTATTTGTGAGTGGTC ACTTTAAAGGAAACTACAAAGC TCAGCTTACACGATTAAATCAT ATCACTAATTGTAATGGAGCTG TTCTTAGTGTAGAAGAGCTTTT AATTGGTGGAAATGATTAAA GCCGGCACATTAACCTTAGAGG AAGTCAGACGGAAATTTAATAA CGGCGAGATAAACTTTAGATCT |
| 13 | FokI Nuclease | SQLVKSELEEKKSELRHKLKYV PHEYIELIEIARNSTQDRILEM KVMEFFMKVYGYRGKHLGGSRK |

-continued

| SEQ ID NO: | Sequence name | Sequence |
|---|---|---|
|  |  | PDGAIYTVGSPIDYGVIVDTKA YSGGYNLPIGQADEMQRYVEEN QTRNKHINPNEWWKVYPSSVTE FKFLFVSGHFKGNYKAQLTRLN HITNCNGAVLSVEELLIGGEMI KAGTLTLEEVRRKFNNGEINFR S |
| 14 | FokI Nuclease | TCCCAACTAGTCAAAAGTGAAC TGGAGGAGAAGAAATCTGAACT TCGTCATAAATTGAAATATGTG CCTCATGAATATATTGAATTAA TTGAAATTGCCAGAAATTCCAC TCAGGATAGAATTCTTGAAATG AAGGTAATGGAATTTTTTATGA AAGTTTATGGATATAGAGGTAA ACATTTGGGTGGATCAAGGAAA CCGGACGGAGCAATTTATACTG TCGGATCTCCTATTGATTACGG TGTGATCGTGGATACTAAAGCT TATAGCGGAGGTTATAATCTGC CAATTGGCCAAGCAGATGAAAT GCAACGATATGTCGAAGAAAAT CAAACACGAAACAAACATATCA ACCCTAATGAATGGTGGAAAGT CTATCCATCTTCTGTAACGGAA TTTAAGTTTTTATTTGTGAGTG GTCACTTTAAAGGAAACTACAA AGCTCAGCTTACACGATTAAAT CATATCACTAATTGTAATGGAG CTGTTCTTAGTGTAGAAGAGCT TTTAATTGGTGGAGAAATGATT AAAGCCGGCACATTAACCTTAG AGGAAGTCAGACGGAAATTTAA TAACGGCGAGATAAACTTTAGA TCT |
| 15 | Nuclear localization signal | CCCAAGAAGAAGAGGAAGGTG |
| 16 | Nuclear localization signal | PKKKRKV |
| 17 | FLAG tag | ATGGACTACAAAGACCATGACG GTGATTATAAAGATCATGACAT CGATTACAAGGATGACGATGAC AAG |
| 18 | FLAG tag | MDYKDHDGDYKDHDIDYKDDDD K |
| 19 | CLYBL target region | CTTACCCTTCTCCCATTTCCTC ATCCTTCCAACATAAATATATT TTGGG |
| 20 | primer | CTGCCGTCTCTCTCCTGAGT |
| 21 | primer | GTGGGCTTGTACTCGGTCAT |

DETAILED DESCRIPTION OF SEVERAL EMBODIMENTS

Described herein are recombinant polynucleotide-binding polypeptides, recombinant fusion proteins incorporating the described polynucleotide-binding polypeptides, methods of using the described recombinant polynucleotide-binding polypeptides and recombinant fusion proteins to modify genomic DNA of cells and, in some embodiments, create recombinant cells.

In order for cell transplantation therapies to be feasible, sufficiently large numbers of cells must be engineered and produced, in a timely manner. Both iPSCs and NSCs retain the ability to self-renew unlike terminally differentiated neural cells. However, the engineering of NSCs hold some advantages over engineering of iPSCs for treating neurodegenerative disease and injury. Direct differentiation to NSCs from adult somatic cells or utilization of NSCs obtained directly from patients will shorten significantly the time to obtain sufficient cells for therapy. NSCs are closely related to the primary cells of the nervous system. Engineering neural fate-restricted NSCs also lessens the chance of differentiation to non-neural tissue.

Methods are available for designing TALENs (Bogdanove and Voytas, Science. 2011 Sep. 30; 333(6051):1843-6. doi: 10.1126/science. 1204094), and TALEN-mediated gene targeting is as effective as ZFNs in human embryonic stem cells (hESCs) and iPSCs (Hockenmeyer et al., Nat Biotechnol 29: 731-734). Genomic editing with TALENs and ZFNs capitalizes on the cell's ability to undergo homology directed repair (HDR), following an induced and targeted double-stranded DNA break (DSB). During this time a donor DNA template can be provided to the cell to insert new transgene or delete DNA sequences at the site of DSB (Cheng et al., Genes Cells. 2012 June; 17(6):431-8. doi: 10.1111/j.1365-2443.2012.01599.x. Epub 2012 Apr. 4).

NSCs transplanted in vivo are able to migrate to and home into sites of injury (Madhavan et al., Int J Mol Sci 2010; 11:3513-28. doi:10.3390/ijms11093513) and secrete a variety of neurotrophic factors to enhance survivability of neural cells and stimulate endogenous repair in the brain (De Feo et al., Current Opinion in Neurology 25: 322-333, (2012)). Transplantation of NSCs has resulted in improvements of symptoms in animal models of Parkinson's (see, for example, Im et al., Mol Imaging. 2013 Jun. 1; 12(4):224-34; Xu et al., Cytotherapy. 2010 April; 12(2):226-37. doi: 10.3109/14653240903490371); Huntington's (Madhavan et al., op cit.; Arien-Zakay et al., Int J Mol Sci 2010; 11:3513-28. doi:10.3390/ijms11093513) Alzheimer's disease (Arien-Zakay et al., supra) multiple sclerosis (Carletti et al., Curr Neuropharmacol 2011; 9:313-7. doi:10.2174/157015911795596603), amyotrophic lateral sclerosis (Arien-Zakay et al., op. cit.) spinal cord injury (see, for example, Zhang et al., Acta Anaesthesiol Scand. 2009 October; 53(9):1184-91. doi: 10.1111/j.1399-6576.2009.02024.x. Epub 2009 Jul. 22), stroke (see, for example, Arien-Zakay et al., op. cit.) and traumatic brain injury (Ma et al., Mol Med Rep. 2011 September-October; 4(5):849-56. doi: 10.3892/mmr.2011.510. Epub 2011 Jun. 16). The preliminary results of NSC transplantation studies suggest the potential for treatment of neurodegenerative disease and injury in humans. In specific, non-liming examples, Parkinson's disease, Huntington's disease, multiple sclerosis, amyotrophic lateral sclerosis, stroke, spinal cord injury or traumatic brain injury can be treated in a subject.

TERMS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Cell Culture: Cells grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Central Nervous System (CNS): The part of the nervous system of an animal that contains a high concentration of cell bodies and synapses and is the main site of integration of nervous activity. In higher animals, the CNS generally refers to the brain and spinal cord.

Differentiation: The process whereby relatively unspecialized cells (e.g., embryonic cells or stem cells) acquire specialized structural and/or functional features characteristic of mature cells. Similarly, "differentiate" refers to this process. Typically, during differentiation, cellular structure alters and tissue-specific proteins and properties appear. The term "differentiated neuronal cell" refers to cells expressing a protein characteristic of the specific neuronal cell type, exhibiting synaptic vesicle release, or having an electrophysiological characteristic of a neuronal cells (e.g., sustained bursts of action potentials). A differentiated neuronal cell can be, for example, a dopaminergic cell, a serotonergic cell or a GABAnergic cell.

Differentiation medium: A synthetic set of culture conditions with the nutrients necessary to support the growth or survival of microorganisms or culture cells, and which allows the differentiation of cells, such as neuronal stem cells.

Donor polynucleotide: A polynucleotide that is capable of specifically inserting into a genomic locus.

Downstream: A relative position on a polynucleotide, wherein the "downstream" position is closer to the 3' end of the polynucleotide than the reference point. In the instance of a double-stranded polynucleotide, the orientation of 5' and 3' ends are based on the sense strand, as opposed to the antisense strand.

Embryonic Stem (ES) Cells: Pluripotent cells isolated from the inner cell mass of the developing blastocyst, or the progeny of these cells. "ES cells" can be derived from any organism. ES cells can be derived from mammals, including mice, rats, rabbits, guinea pigs, goats, pigs, cows, monkeys and humans. In specific, non-limiting examples, the cells are human or murine. Without being bound by theory, ES cells can generate a variety of the cells present in the body (bone, muscle, brain cells, etc.), provided they are exposed to conditions conducive to developing these cell types. Methods for producing murine ES cells can be found in U.S. Pat. No. 5,670,372, which is herein incorporated by reference. Methods for producing human ES cells can be found in U.S. Pat. No. 6,090,622, WO 00/70021 and WO 00/27995, which are herein incorporated by reference.

Effective amount or Therapeutically effective amount: The amount of agent, such a cell, for example NSCs, that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount sufficient to reduce or eliminate a symptom of a disease. In another embodiment, a therapeutically effective amount is an amount sufficient to overcome the disease itself.

Exogenous: Not normally present in a cell, but can be introduced by genetic, biochemical or other methods. Exogenous nucleic acids include DNA and RNA, which can be single or double-stranded; linear, branched or circular; and can be of any length. By contrast, an "endogenous" molecule is one that is normally present in a particular cell at a particular developmental stage under particular environmental conditions.

Expand: A process by which the number or amount of cells in a culture is increased due to cell division. Similarly, the terms "expansion" or "expanded" refers to this process. The terms "proliferate," "proliferation" or "proliferated" may be used interchangeably with the words "expand," "expansion" or "expanded." Typically, during an expansion phase, the cells do not differentiate to form mature cells.

Expansion medium: A synthetic set of culture conditions suitable for the expansion of cells, such as neuronal stem cells. Tissue culture media generally include a carbon source, a nitrogen source and a buffer to maintain pH. In one embodiment, a medium contains a minimal essential media, such as DMEM, supplemented with various nutrients to enhance neuronal stem cell growth. Additionally, the minimal essential media may be supplemented with additives such as horse, calf or fetal bovine serum.

FokI nuclease: A nonspecific DNA nuclease that occurs naturally in *Flavobacterium okeanokoites*. The term includes recombinant and mutant forms of the protein, fragments of the FokI nuclease protein, and recombinant and mutant forms thereof that retain nuclease activity that are, or may be, fused to a DNA-binding polypeptide.

The term "fusion" or "fused" when used in the context of a fusion protein, or similar construct, means the covalent joining of two polypeptide products (or their corresponding polynucleotides) by genetic engineering. The fused segments may be fused directly to one another, but may also be indirectly fused to one another having interceding sequences between the segments of interest.

Genomic insertion site: A site of the genome that is targeted for, or has undergone, insertion of an exogenous polynucleotide.

Growth factor: A substance that promotes cell growth, survival, and/or differentiation. Growth factors include molecules that function as growth stimulators (mitogens), molecules that function as growth inhibitors (e.g. negative growth factors) factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are bFGF, epidermal growth factor (EGF), CNTF, HGF, nerve growth factor (NGF), and actvin-A.

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Induced pluripotent stem cell" ("iPS" cell or "iPSC"): A pluripotent stem cell artificially derived from a non-pluripotent cell, typically an adult somatic cell, by recombinant expression of specific factors in the non-pluripotent cell.

Factors that may be used to for iPSCs include, but are not limited to, one or more of Oct-3/4, certain members of the Sox gene family (Sox1, Sox2, Sox3, and Sox15), Klf family members (Klf1, Klf2, Klf4, and Klf5), factors of the Myc family (c-myc, L-myc, and N-myc), Nanog, and LIN28, as defined by current knowledge in the art. Other factors or methods useful for creating iPSCs are also known in the art and are considered to produce cells that fall within the scope of this definition.

Isolated: An "isolated" biological component (such as a nucleic acid, peptide or cell) has been substantially separated, produced apart from, or purified away from other biological components or cells of the organism in which the component naturally occurs, i.e., other chromosomal and extrachromosomal DNA and RNA, cells and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Lineage-specific: Characteristics of a cell that indicate the cell will become one of a limited number of related cell types or a particular cell type, such as a differentiated cell or a cell undergoing the process of differentiation into a specific cell type or a mature cell type.

Modulate: A change in the content of genomic DNA gene. Modulation can include, but is not limited to, gene activation, gene repression, gene deletion, polynucleotide insertion, and polynucleotide excision.

Neural cell: A cell that exhibits a morphology, a function, and a phenotypic characteristic similar to that of glial cells and neurons derived from the central nervous system and/or the peripheral nervous system.

There are several types of neurons (neuronal cells). Cholinergic neurons manufacture acetylcholine. GABAergic neurons manufacture gamma aminobutyric acid (GABA). Glutamatergic neurons manufacture glutamate. Dopaminergic neurons manufacture dopamine. Serotonergic neurons manufacture serotonin.

Neuronal stem cell (NSC): Undifferentiated, multipotent, self-renewing neural cell. A NSC is a multipotent stem cell which is able to divide and, under appropriate conditions, has self-renewal capability and can terminally differentiate into neurons, astrocytes, and oligodendrocytes. Hence, the neural stem cell is "multipotent" because stem cell progeny have multiple differentiation pathways. A NSC is capable of self maintenance, meaning that with each cell division, at least one daughter cell will also be, on average, a stem cell. Neural stem cells can be derived from tissues including, but not limited to brain and spinal cord. A "long term" NSC divides in culture for at least 15 cell divisions, such as at least 15, 20, 25, 30, 35, 40, 45 or 50 cell divisions. A long term retains the properties of a neuronal stem cell, such as expression of nestin and sox1, and has the capacity to differentiate into neurons and glia in appropriate culture conditions in vitro.

NSCs can be obtained from a cadaver or living subject, including from fetal tissue and adult brain biopsies. NSCs can be produced from other stem cells, such as induced pluripotent stem cells or embryonic stem cells. NSCs can be autologous or heterologous to a recipient.

Neurological disorder: A disorder in the nervous system, including the central nervous system (CNS) and peripheral nervous system (PNS). Examples of neurological disorders include Parkinson's disease, Huntington's disease, Alzheimer's disease, severe seizure disorders including epilepsy, familial dysautonomia as well as injury or trauma to the nervous system, such as neurotoxic injury or disorders of mood and behavior such as addiction, schizophrenia and amyotrophic lateral sclerosis. Neuronal disorders also include Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and other lipid storage and genetic brain diseases and/or schizophrenia Neurodegenerative disorder: An abnormality in the nervous system of a subject, such as a mammal, in which neuronal integrity is threatened. Without being bound by theory, neuronal integrity can be threatened when neuronal cells display decreased survival or when the neurons can no longer propagate a signal. Specific, non-limiting examples of a neurodegenerative disorder are Alzheimer's disease, Pantothenate kinase associated neurodegeneration, Parkinson's disease, Huntington's disease (Dexter et al., *Brain* 114:1953-1975, 1991), HIV encephalopathy (Miszkziel et al., *Magnetic Res. Imag.* 15:1113-1119, 1997), and amyotrophic lateral sclerosis.

Alzheimer's disease manifests itself as pre-senile dementia. The disease is characterized by confusion, memory failure, disorientation, restlessness, speech disturbances, and hallucination in mammals (*Medical, Nursing, and Allied Health Dictionary*, 4th Ed., 1994, Editors: Anderson, Anderson, Glanze, St. Louis, Mosby).

Parkinson's disease is a slowly progressive, degenerative, neurologic disorder characterized by resting tremor, loss of postural reflexes, and muscle rigidity and weakness (*Medical, Nursing, and Allied Health Dictionary*, 4th Ed., 1994, Editors: Anderson, Anderson, Glanze, St. Louis, Mosby).

Amyotrophic lateral sclerosis is a degenerative disease of the motor neurons characterized by weakness and atrophy of the muscles of the hands, forearms and legs, spreading to involve most of the body and face (*Medical, Nursing, and Allied Health Dictionary*, 4th Ed., 1994, Editors: Anderson, Anderson, Glanze, St. Louis, Mosby).

Pantothenate kinase associated neurodegeneration (PKAN, also known as Hallervorden-Spatz syndrome) is an autosomal recessive neurodegenerative disorder associated with brain iron accumulation. Clinical features include extrapyramidal dysfunction, onset in childhood, and a relentlessly progressive course (Dooling et al., *Arch. Neurol.* 30:70-83, 1974). PKAN is a clinically heterogeneous group of disorders that includes classical disease with onset in the first two decades, dystonia, high globus pallidus iron with a characteristic radiographic appearance (Angelini et al., *J. Neurol.* 239:417-425, 1992), and often either pigmentary retinopathy or optic atrophy (Dooling et al., *Arch. Neurol.* 30:70-83, 1974; Swaiman et al., *Arch. Neurol* 48:1285-1293, 1991).

A "neurodegenerative-related disorder" is a disorder such as speech disorders that are associated with a neurodegenerative disorder. Specific non-limiting examples of a neurodegenerative related disorders include, but are not limited to, palilalia, tachylalia, echolalia, gait disturbance, perseverative movements, bradykinesia, spasticity, rigidity, retinopathy, optic atrophy, dysarthria, and dementia.

Nucleofection: Electroporation. Nucleofection uses a combination of electrical parameters, generated by a device called Nucleofector, with cell-type specific reagents. The substrate is transferred directly into the cell nucleus and the cytoplasm.

Peripheral Nervous System (PNS): The part of an animal's nervous system other than the Central Nervous System. Generally, the PNS is located in the peripheral parts of the body and includes cranial nerves, spinal nerves and their branches, and the autonomic nervous system.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent or "drug": A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Polypeptide: Three or more covalently attached amino acids. The term encompasses proteins, protein fragments, and protein domains. A "DNA-binding" polypeptide is a polypeptide with the ability to specifically bind DNA.

The term "polypeptide" is specifically intended to cover naturally occurring proteins, as well as those which are recombinantly or synthetically produced. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Recombination: A process of exchange of genetic information between two polynucleotides. "Homologous recombination (HR)" refers to the specialized form of an exchange that takes place, for example, during repair of double-strand breaks in cells. Nucleotide sequence homology is utilized in recombination, for example using a "donor" molecule to template repair of a "target" molecule (i.e., the one that experienced the double-strand break), and is variously known as "non-crossover gene conversion" or "short tract gene conversion," because it leads to the transfer of genetic information from the donor to the target.

Safe harbor: A locus in the genome where a polynucleotide may be inserted without causing deleterious effects to the host cell. Examples of safe harbor loci known to exist within mammalian cells may be found within the AAVS1 gene, the CYBL gene, and the CCR5 gene.

Selectable marker: A gene introduced into a cell, such mammalian cells in culture, for example a NSC, that confers a trait suitable for artificial selection from cells that do not possess the gene.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a FGF polypeptide will possess a relatively high degree of sequence identity when aligned using standard methods.

Methods of alignment of sequences for comparison are well known in the art. Various programs and alignment algorithms are described in Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul, et al., *Nature Genet.*, 6:119, 1994 presents a detailed consideration of sequence alignment methods and homology calculations.

The NCBI Basic Local Alignment Search Tool (BLAST) (Altschul, et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a FGF polypeptide are typically characterized by possession of at least about 75%, for example at least about 80%, sequence identity counted over the full length alignment with the amino acid sequence of the factor using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding: A sequence-specific, non-covalent interaction between macromolecules (e.g., between a polypeptide and a polynucleotide). Not all components of a binding interaction need be sequence-specific (e.g., contacts with phosphate residues in a DNA backbone), as long as the interaction as a whole is sequence-specific. The term should not be construed to indicate that a macromolecule described as participating in specific binding, or as being specific for another given macromolecule, cannot bind to another macromolecule, but rather that the specific nature of the interaction is significantly favored over a nonspecific or random binding. Such "specific binding" interactions are generally characterized by a dissociation constant ($K_d$) of $10^{-6}$ $M^{-1}$ or lower.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human.

Synapse: Highly specialized intercellular junctions between neurons and between neurons and effector cells across which a nerve impulse is conducted (synaptically active). Generally, the nerve impulse is conducted by the release from one neuron (presynaptic neuron) of a chemical transmitter (such as dopamine or serotonin) which diffuses across the narrow intercellular space to the other neuron or effector cell (post-synaptic neuron). Generally neurotransmitters mediate their effects by interacting with specific receptors incorporated in the post-synaptic cell. "Synaptically active" refers to cells (e.g., differentiated neurons) which receive and transmit action potentials characteristic of mature neurons.

Transduced, Transformed and Transfected: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses (Wolff, J. A., ed, *Gene Therapeutics*, Birkhauser, Boston, USA, 1994). In the case of infection by retroviruses, the infecting retrovirus particles are absorbed by the target cells, resulting in reverse transcription of the retroviral RNA genome and integration of the resulting provirus into the cellular DNA. Methods for the introduction of genes into cells are known (e.g. see U.S. Pat. No. 6,110,743, herein incorporated by reference). These methods can be used to transduce a NSC or a cell produced by the methods described herein.

Genetic modification of the target cell is an indicium of successful transfection. "Genetically modified cells" refers to cells whose genotypes have been altered as a result of cellular uptakes of exogenous nucleotide sequence by transfection. A reference to a transfected cell or a genetically modified cell includes both the particular cell into which a vector or polynucleotide is introduced and progeny of that cell.

Transgene: An exogenous gene.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

Upstream: A relative position on a polynucleotide, wherein the "upstream" position is closer to the 5' end of the polynucleotide than the reference point. In the instance of a double-stranded polynucleotide, the orientation of 5' and 3' ends are based on the sense strand, as opposed to the antisense strand.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Zinc finger DNA binding domain: A polypeptide domain that binds DNA in a sequence-specific manner through one or more zinc fingers, which are regions of amino acid sequence within the binding domain whose structure is stabilized through coordination of a zinc ion.

Zinc finger binding domains, for example the recognition helix of a zinc finger, can be "engineered" to bind to a predetermined nucleotide sequence. Rational criteria for design of zinc finger binding domains include application of substitution rules and computerized algorithms for processing information in a database storing information of existing ZFP designs and binding data, see for example U.S. Pat. No. 5,789,538; U.S. Pat. No. 5,925,523; U.S. Pat. No. 6,007,988; U.S. Pat. No. 6,013,453; U.S. Pat. No. 6,140,081; U.S. Pat. No. 6,200,759; U.S. Pat. No. 6,453,242; and U.S. Pat. No. 6,534,261; and PCT Publication Nos. WO 95/19431; WO 96/06166; WO 98/53057; WO 98/53058; WO 98/53059; WO 98/53060; WO 98/54311; WO 00/27878; WO 01/60970; WO 01/88197; WO 02/016536; WO 02/099084 and WO 03/016496.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, "A or B" is intended to include "A," "B," and "both A and B," unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Compositions for Targeting NSCs

Disclosed below are compositions that can be used to genetically modify NSCs. These compositions can be used in any of the methods disclosed herein.

A. DNA-Binding Polypeptides

The recombinant polynucleotide-binding polypeptides of use in the methods disclosed herein can occur in a variety of forms. In some embodiments the recombinant polynucleotide-binding polypeptide is a recombinant DNA-binding polypeptide that specifically binds to a genomic target sequence of a subject (e.g., in a neuronal stem cell). In one embodiment the targeted genomic sequence bound by the recombinant DNA-binding polypeptide falls within sequence of SEQ ID NO: 19, or its corresponding antisense sequence. In another embodiment the targeted sequence bound by the recombinant DNA-binding polypeptide (e.g., in the genome of the neuronal stem cell) includes the sequence of SEQ ID NO: 1. In yet another embodiment, the targeted sequence bound by the recombinant DNA-binding polypeptide is the sequence of SEQ ID NO: 1. Alternatively, the targeted sequence bound by the recombinant DNA-binding polypeptide may include a sequence that is antisense, or complementary, to the sequence of SEQ ID NO: 1. In one embodiment, the targeted sequence bound by the recombinant DNA-binding polypeptide is a sequence that is antisense, or complementary, to the sequence of SEQ ID NO: 1. In another embodiment the targeted sequence bound by the recombinant DNA-binding polypeptide includes the sequence of SEQ ID NO: 3. In a further embodiment, the targeted sequence bound by the recombinant DNA-binding polypeptide is the sequence of SEQ ID NO: 3. Alternatively, the targeted sequence bound by the recombinant DNA-binding polypeptide can include a sequence that is antisense, or complementary, to the sequence of SEQ ID NO: 3. In one embodiment, the targeted sequence bound by the recombinant DNA-binding polypeptide is a sequence that is antisense, or complementary, to the sequence of SEQ ID NO: 3.

In some embodiments the described recombinant DNA-binding polypeptide includes a zinc-finger domain or a transcription activator-like effector (TALE) domain, or a polypeptide fragment thereof that retains the DNA binding function of the TALE domain or the zinc-finger domain. Furthermore, the recombinant DNA-binding polypeptide may also be combined with a polypeptide having nuclease activity, such as a zinc-finger domain or a transcription activator-like effector (TALE) domain fused to a nuclease protein, or a fragment thereof. Exemplary nucleases include S1 nucleoase, mung bean nuclease, pancreatic DNAase I, micrococcal nuclease; yeast HO endonuclease; see also Linn et al. (eds.) Nucleases, Cold Spring Harbor Laboratory Press, 1993).

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at nine nucleotides from its recognition site on one strand and 13 nucleotides from its recognition site on the other (see, for example, U.S. Pat. Nos. 5,356,802; 5,436,150 and 5,487,994; Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31, 978-31, 982). Thus, in one embodiment, a nuclease domain from at least one Type IIS restriction enzyme is utilized. An exemplary Type IIS restriction enzyme, whose cleavage domain is separable from the binding domain, is Fok1. This particular enzyme is active as a dimer. Bitinaite et al. (1998) Proc. Natl. Acad. Sci. USA 95: 10,570-10,575. Additional forms of FokI nuclease are set forth in U.S. Published Patent Application No. 20110027235, which is incorporated herein by reference.

In some embodiments the polypeptide having nuclease activity that is fused with the recombinant DNA-binding polypeptide is the FokI nuclease, or a derivative or fragment thereof that retains the nuclease activity. In some embodiments, the Fok1 nuclease is at least about 80%, at least about 85%, at least about 90%, at least about 95%, at least about 96%, at least about 97%, at least about 98%, at least about 99%, or about 100% identical to SEQ ID NO: 13.

In the case of a recombinant DNA-binding polypeptide produced from a TALE domain, fusion with a polypeptide having nuclease activity forms a transcription activator-like effector nuclease (TALEN). Some of the TALEN embodiments described herein are designed to specifically target a genomic sequence that falls within the sequence of SEQ ID NO: 19, or its corresponding antisense sequence, such as, for example, the sequence of SEQ ID NO: 1 or 3. In one embodiment the targeted sequence bound by a described TALE domain includes the sequence of SEQ ID NO: 1. In one embodiment, the targeted sequence bound by a described TALE domain is the sequence of SEQ ID NO: 1. Alternatively, the targeted sequence bound by a described TALE domain may include a sequence that is antisense, or complementary, to the sequence of SEQ ID NO: 1. In one embodiment, the targeted sequence bound by a described TALE domain is a sequence that is antisense, or complementary, to the sequence of SEQ ID NO: 1. In another embodiment the targeted sequence bound by a described TALE domain includes the sequence of SEQ ID NO: 3. In one embodiment, the targeted sequence bound by a described TALE domain is the sequence of SEQ ID NO: 3. Alternatively, the targeted sequence bound by a described TALE domain may include a sequence that is antisense, or complementary, to the sequence of SEQ ID NO: 3. In one embodiment, the targeted sequence bound by a described TALE domain is a sequence that is antisense, or complementary, to the sequence of SEQ ID NO: 3.

The TALE domains of use in the methods disclosed herein can be linked to a polypeptide having nuclease activity to form a TALEN, which can be used to cleave DNA at a specific location of interest. In one embodiment the targeted sequence bound by a described TALEN includes the sequence of SEQ ID NO: 1. In one embodiment, the targeted sequence bound by a described TALEN is the sequence of SEQ ID NO: 1. Alternatively, the targeted sequence bound by a described TALEN may include a sequence that is antisense, or complementary, to the sequence of SEQ ID NO: 1. In one embodiment, the targeted sequence bound by a described TALEN is a sequence that is antisense, or complementary, to the sequence of SEQ ID NO: 1. In another embodiment the targeted sequence bound by a described TALEN includes the sequence of SEQ ID NO: 3. In one embodiment, the targeted sequence bound by a described TALEN is the sequence of SEQ ID NO: 3. Alternatively, the targeted sequence bound by a described TALEN may include a sequence that is antisense, or complementary, to the sequence of SEQ ID NO: 3. In one embodiment, the targeted sequence bound by a described TALEN is a sequence that is antisense, or complementary, to the sequence of SEQ ID NO: 3.

For the methods disclosed herein, the recombinant DNA-binding polypeptide may also be combined with a polypeptide having nuclease activity, such as a zinc-finger domain or a transcription activator-like effector (TALE) domain fused to a nuclease protein, or a fragment thereof. In some embodiments the polypeptide having nuclease activity that is fused with the recombinant DNA-binding polypeptide is the fokI nuclease, or a derivative or fragment thereof that retains the nuclease activity. In the case of a recombinant DNA-binding polypeptide produced from a TALE domain, fusion with a polypeptide having nuclease activity forms a transcription activator-like effector nuclease (TALEN).

Some of the TALEN embodiments of use in the disclosed methods are designed to specifically target a genomic sequence that falls within the sequence of SEQ ID NO: 19, or its corresponding antisense sequence, such as, for example, the sequence of SEQ ID NO: 1 or 3. In one embodiment the TALE domain includes the amino acid sequence of SEQ ID NO: 7. In another embodiment the TALE domain includes an amino acid sequence of SEQ ID NO: 10. In further embodiments a TALE domain is fused to a polypeptide having nuclease activity to form a TALEN. One TALEN of use in the methods disclosed herein is a TALE domain that includes the amino acid sequence of SEQ ID NO: 7 is incorporated into a polypeptide having nuclease activity. In one such embodiment, the amino acid sequence of SEQ ID NO: 7 is incorporated into a polypeptide that also includes a fokI nuclease, or a fragment thereof. For example, the amino acid sequence of SEQ ID NO: 7 may be incorporated into a polypeptide that also includes the amino acid sequence of SEQ ID NO: 13. One embodiment of a polypeptide where the amino acid sequence of SEQ ID NO: 7 is incorporated with the amino acid sequence of SEQ ID NO: 13, is the polypeptide of SEQ ID NO: 8. One TALEN of use in the methods disclosed herein is a TALE domain that includes the amino acid sequence of SEQ ID NO: 10 is incorporated into a polypeptide having nuclease activity. In one such embodiment, the amino acid sequence of SEQ ID NO: 10 is incorporated into a polypeptide that also includes a fokI nuclease, or a fragment thereof that retains nuclease activity. For example, the amino acid sequence of SEQ ID NO: 10 may be incorporated into a polypeptide that also includes the amino acid sequence of SEQ ID NO: 13. One embodiment of a polypeptide where the amino acid sequence of SEQ ID NO: 10 is incorporated with the amino acid sequence of SEQ ID NO: 13, is the polypeptide of SEQ ID NO: 11.

The TALE constructs of use in the methods disclosed herein can be used to target specific DNA sequences, such as a genomic sequence of interest in an NSC. When coupled with a polypeptide having nuclease activity to form a TALEN, these constructs can be used to target a specific polynucleotide of interest for modification (e.g., in the genome of the NSC). In one embodiment the described TALE domain includes the amino acid sequence of SEQ ID NO: 7 which can target the sequence of SEQ ID NO: 1 specifically. In another embodiment the TALE domain includes an amino acid sequence of SEQ ID NO: 10 which can target the sequence of SEQ ID NO: 3 specifically. In further embodiments a described TALE domain is fused to a polypeptide having nuclease activity to form a TALEN. One TALEN described herein is a TALE domain that includes the amino acid sequence of SEQ ID NO: 7 is incorporated into a polypeptide having nuclease activity, which can target the sequence of SEQ ID NO: 1 specifically. In one such embodiment, the amino acid sequence of SEQ ID NO: 7 is incorporated into a polypeptide that also includes a fokI nuclease, or a fragment thereof that retains nuclease activity, and can target the sequence of SEQ ID NO: 1 specifically and mediate cleavage of a DNA sequence proximal to the segment where the polynucleotide is bound. For example, the amino acid sequence of SEQ ID NO: 7 may be incorporated into a polypeptide that also includes the amino acid sequence of SEQ ID NO: 13, for specific targeting of the sequence of SEQ ID NO: 1 and cleavage of the polynucleotide sequence proximal to the binding locus. One embodiment of a polypeptide where the amino acid sequence of SEQ ID NO: 7 is incorporated with the amino acid sequence of SEQ ID NO: 13, is the polypeptide of SEQ ID NO: 8, which can specifically bind the sequence of SEQ ID NO: 1 and cleave the polynucleotide sequence proximal to the binding locus. Another TALEN of use in the methods disclosed herein is a TALE domain that includes the amino acid sequence of SEQ ID NO: 10 is incorporated into a polypeptide having nuclease activity, which can target the sequence of SEQ ID NO: 3 specifically. In one such embodiment, the amino acid sequence of SEQ ID NO: 10 is incorporated into a polypeptide that also includes a fokI nuclease, or a fragment thereof that retains nuclease activity, and can target the sequence of SEQ ID NO: 3 specifically and mediate cleavage of a DNA sequence proximal to the segment where the polynucleotide is bound. For example, the amino acid sequence of SEQ ID NO: 10 may be incorporated into a polypeptide that also includes the amino acid sequence of SEQ ID NO: 13, for specific targeting of the sequence of SEQ ID NO: 3 and cleavage of the polynucleotide sequence proximal to the binding locus. One embodiment of a polypeptide where the amino acid sequence of SEQ ID NO: 10 is incorporated with the amino acid sequence of SEQ ID NO: 13, is the polypeptide of SEQ ID NO: 11, which can specifically bind the sequence of SEQ ID NO: 3 and cleave the polynucleotide sequence proximal to the binding locus.

Modifications could be made to the described subject matter resulting in substantially similar polypeptides and constructs that carry out essentially the same functions, in substantially the same way, as the described polynucleotide-binding polypeptides and related nuclease constructs. For zinc-finger-based constructs, or CRISPR technology, could be used to target the loci described herein to modify a genome of a cell or chromosomal DNA. Accordingly, such variations are considered to be within the scope of the present disclosure.

Many of the embodiments disclosed in this section are described in combination with, or in the context of, fokI nuclease, or a nuclease-retaining fragment thereof; however, it should be understood that other nuclease proteins, or functional fragments thereof, could also be used in an analogous manner to form the described compositions and carry out the described methods. For example, mung bean nuclease, pancreatic DNAase I, micrococcal nuclease, yeast HO endonuclease, and others may be used in this context. (See, e.g., Linn et al. 1993 and Schierling et al., Nucleic Acids Res. 2012 March; 40(6): 2623-2638.)

Polynucleotides and Vectors

Polynucleotides and vectors are of use in the methods disclosed herein. The polynucleotides encode the polypeptides disclosed above. In some embodiments, the polynucleotides and vectors encode recombinant DNA-binding polypeptides, zinc-finger or TALE domains, nuclease proteins or polypeptides, fusion proteins produced from the fusion of DNA-binding polypeptides and nuclease proteins or polypeptides, such as TALENs. In some embodiments the expression of the polypeptides encoded by the vectors are controlled by an inducible promoter, such as a promoter that directs expression specifically in neuronal and/or glial cells. Suitable promoters include, but are not limited to, the doubecourtin (DCX) promoter and glial fibrillary acidic protein (GFAP). In other embodiments the expression of the polypeptides encoded by the vectors are controlled by a repressible promoter. Recombinant (e.g., Neuronal stem) cells can be modified by the described vectors, for example transfected cells or cells having an expression product of the vectors.

The polypeptides described herein can be encoded by a variety of polynucleotides due to the degeneracy of the genetic code. Thus, the polynucleotides provided herein may be altered to encode the same corresponding amino acid sequences disclosed herein, as would be understood by those skilled in the art. Accordingly, the use of such varied polynucleotide sequences should be considered within the scope of the presently claimed methods. The amino acid sequence of SEQ ID NO: 7 may be encoded by a nucleotide having the sequence of SEQ ID NO: 2. The amino acid sequence of SEQ ID NO: 8 may be encoded by a nucleotide having the sequence of SEQ ID NO: 5. The amino acid sequence of SEQ ID NO: 10 may be encoded by a nucleotide having the sequence of SEQ ID NO: 4. The amino acid sequence of SEQ ID NO: 11 may be encoded by a nucleotide having the sequence of SEQ ID NO: 6. The amino acid sequence of SEQ ID NO: 13 may be encoded by a nucleotide having the sequence of SEQ ID NO: 14.

Furthermore, the vectors of use in the methods disclosed herein, that express the polynucleotides, or produce the polypeptides, may be substituted for other vectors having similar functional capabilities that would be understood by those skilled in the art having benefit of the present disclosure. In one embodiment, the polypeptide of SEQ ID NO: 8 may be produced by the polynucleotide of SEQ ID NO: 9. In another embodiment the polypeptide of SEQ ID NO: 11 may be encoded by the polynucleotide of SEQ ID NO: 12.

Also described are cells that have been modified to include one or more of the polynucleotides described herein. The cells described herein that may be modified to include one or more disclosed polynucleotides include, but are not limited to, somatic cells, embryonic stem cells, iPS cells, or autologous cells of a subject. A variety of methods of transforming cells to include a polynucleotide can be used to produce the modified cells described herein, as would be understood by those skilled in the art. In particular embodiments the forgoing cells may be modified by nucleofection to cause the recited polynucleotides to be present in the nucleus of the cells. In more particular embodiments the forgoing cells may be modified by nucleofection, using a Nucleofector™ apparatus, to cause the recited polynucleotides to be present in the nucleus of the cells. In some embodiments, the nucleofection provides a transfection efficiency of at least about 60%, at least about 65%, at least about 70%, at least about 75%, at least about 80%, at least about 85%, at least about 90%, or at least about 95%. In specific non-limiting example, the transfection efficiency is at least about 80%, at least about 85%, at least about 90%, at least about 95%, at least about 96%, about 97%, about 98% or about 99%. In one embodiment a cell is modified to include a polynucleotide having the sequence of SEQ ID NO: 2. In one embodiment a stem cell is modified to include a polynucleotide having the sequence of SEQ ID NO: 2. In one embodiment a somatic cell is modified to include a polynucleotide having the sequence of SEQ ID NO: 2. In one embodiment an iPS cell is modified to include a polynucleotide having the sequence of SEQ ID NO: 2. In one embodiment an autologous cell of a subject is modified to include a polynucleotide having the sequence of SEQ ID NO: 2. In one embodiment a cell is modified to include a polynucleotide having the sequence of SEQ ID NO: 4. In one embodiment a stem cell is modified to include a polynucleotide having the sequence of SEQ ID NO: 4. In one embodiment a somatic cell is modified to include a polynucleotide having the sequence of SEQ ID NO: 4. In one embodiment an iPS cell is modified to include a polynucleotide having the sequence of SEQ ID NO: 4. In one embodiment an autologous cell of a subject is modified to include a polynucleotide having the sequence of SEQ ID NO: 4. In one embodiment a cell is modified to include a polynucleotide having the sequence of SEQ ID NO: 5. In one embodiment a stem cell is modified to include a polynucleotide having the sequence of SEQ ID NO: 5. In one embodiment a somatic cell is modified to include a polynucleotide having the sequence of SEQ ID NO: 5. In one embodiment an iPS cell is modified to include a polynucleotide having the sequence of SEQ ID NO: 5. In one embodiment an autologous cell of a subject is modified to include a polynucleotide having the sequence of SEQ ID NO: 5. In one embodiment a cell is modified to include a polynucleotide having the sequence of SEQ ID NO: 6. In one embodiment a stem cell is modified to include a polynucleotide having the sequence of SEQ ID NO: 6. In one embodiment a somatic cell is modified to include a polynucleotide having the sequence of SEQ ID NO: 6. In one embodiment an iPS cell is modified to include a polynucleotide having the sequence of SEQ ID NO: 6. In one embodiment an autologous cell of a subject is modified to include a polynucleotide having the sequence of SEQ ID NO: 6. In one embodiment a cell is modified to include a polynucleotide having the sequence of SEQ ID NO: 9. In one embodiment a stem cell is modified to include a polynucleotide having the sequence of SEQ ID NO: 9. In one embodiment a somatic cell is modified to include a polynucleotide having the sequence of SEQ ID NO: 9. In one embodiment an iPS cell is modified to include a polynucleotide having the sequence of SEQ ID NO: 9. In one embodiment an autologous cell of a subject is modified to include a polynucleotide having the sequence of SEQ ID NO: 9. In one embodiment a cell is modified to include a polynucleotide having the sequence of SEQ ID NO: 12. In one embodiment a stem cell is modified to include a polynucleotide having the sequence of SEQ ID NO: 12. In one embodiment a somatic cell is modified to include a polynucleotide having the sequence of SEQ ID NO: 12. In one embodiment an iPS cell is modified to include a polynucleotide having the sequence of SEQ ID NO: 12. In one embodiment an autologous cell of a subject is modified to include a polynucleotide having the sequence of SEQ ID NO: 12. In one embodiment the genome of a cell is modified to include an exogenous polynucleotide encoding a gene of interest. In one embodiment the genome of a stem cell is modified to include an exogenous polynucleotide encoding a gene of interest. In one embodiment the genome of an iPS cell is modified to include an exogenous polynucleotide encoding a gene of interest. In one embodiment the genome of a somatic cell is modified to include an exogenous polynucleotide encoding a gene of interest. In one embodiment the genome of an autologous cell of a subject is modified to include an exogenous polynucleotide encoding a gene of interest. In one embodiment a cell is modified to have a polypeptide encoded by a polynucleotide having the sequence of SEQ ID NO: 2. In one embodiment a stem cell is modified to have a polypeptide encoded by a polynucleotide having the sequence of SEQ ID NO: 2. In one embodiment a somatic cell is modified to have a polypeptide encoded by a polynucleotide having the sequence of SEQ ID NO: 2. In one embodiment an iPS cell is modified to have a polypeptide encoded by a polynucleotide having the sequence of SEQ ID NO: 2. In one embodiment an autologous cell of a subject is modified to have a polypeptide encoded by a polynucleotide having the sequence of SEQ ID NO: 2. In one embodiment a cell is modified to have a polypeptide encoded by a polynucleotide having the sequence of SEQ ID NO: 4. In one embodiment a stem cell is modified to have a polypeptide encoded by a polynucleotide having the sequence of SEQ ID NO: 4. In one embodiment a somatic cell is modified to have a polypeptide encoded by a polynucleotide having the sequence of SEQ ID NO: 4. In one embodiment an iPS cell is modified to have a polypeptide encoded by a polynucleotide having the sequence of SEQ ID NO: 4. In one embodiment an autologous cell of a subject is modified to have a polypeptide encoded by a polynucleotide having the sequence of SEQ ID NO: 4. In one embodiment a cell is modified to have a polypeptide encoded by a polynucleotide having the sequence of SEQ ID NO: 5. In one embodiment a stem cell is modified to have a polypeptide encoded by a polynucleotide having the sequence of SEQ ID NO: 5. In one embodiment a somatic cell is modified to have a polypeptide encoded by a polynucleotide having the sequence of SEQ ID NO: 5. In one embodiment an iPS cell is modified to have a polypeptide encoded by a polynucleotide having the sequence of SEQ ID NO: 5. In one embodiment an autologous cell of a subject is modified to have a polypeptide encoded by a polynucleotide having the sequence of SEQ ID NO: 5. In one embodiment a cell is modified to have a polypeptide encoded by a polynucleotide having the sequence of SEQ ID NO: 6. In one embodiment a stem cell is modified to have a polypeptide encoded by a polynucleotide having the sequence of SEQ ID NO: 6. In one embodiment a somatic cell is modified to have a polypeptide encoded by a polynucleotide having the sequence of SEQ ID NO: 6. In one embodiment an iPS cell is modified to have a polypeptide encoded by a polynucleotide having the sequence of SEQ ID NO: 6. In one embodiment an autologous cell of a subject is modified to have a polypeptide encoded by a polynucleotide having the sequence of SEQ ID NO: 6.

Provided herein are donor polynucleotides that may be inserted into the genome of a cell (e.g., neuronal stem cell). In some embodiments the donor polynucleotides are double-stranded polynucleotides with sense and/or antisense strand polynucleotide overhangs that are at least partially complementary to corresponding polynucleotide overhangs of cleaved genomic DNA to facilitate insertion of the donor polynucleotide with the cleaved genomic DNA. In additional embodiments the donor polynucleotides are single-stranded polynucleotides with sense and/or antisense strand polynucleotide overhangs (portions) that are at least partially complementary to corresponding polynucleotide overhangs of cleaved genomic DNA to facilitate insertion of the donor polynucleotide with the cleaved genomic DNA. In some embodiments the donor polynucleotide may express a polypeptide once inserted into the genome of a cell (e.g., neuronal cell or a cell differentiated therefrom). In some embodiments the expressed polypeptide can be a protein that can function to induce cell differentiation or maturation to proceed in a particular manner, such as toward a specific cell lineage, such as neuronal or glial cells. In some embodiments the expression of a polypeptide by the donor polynucleotide may be controlled by an inducible promoter, such as a promoter expressed in neuronal cells and/or glial cells. In other embodiments, the expression of a polypeptide by the donor polynucleotide may be controlled by a repressible promoter. In still other embodiments the donor polynucleotide may encode more than one polypeptide, for example, the donor polynucleotide may include an expression cassette having a plurality of genes. In certain embodiments the where the donor polynucleotide encodes more than one polypeptide, the donor polynucleotide may have inducible promoters to regulate the expression of certain genes and repressible promoters to regulate the expression of other genes. In some embodiments, the donor polynucleotide is a single-stranded or double-stranded donor polynucleotide with sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, such that the polynucleotide is introduced into the genome of the cell. In some embodiments, the overhangs are from about 15 base pairs to about 500 base pairs. In some embodiments, the overhangs are at least 15 nucleotides in length, such as 20, 30, 40, 50, 60, 70, 80, 90, 100, 200, 300, 400, 500, 600, 700, 800, 900, or 1,000 base pairs. In one embodiment the overhangs are at least 15 base pairs. In one embodiment, the overhangs are about 15 base pairs. In one embodiment, the overhangs are about 25 base pairs. In one embodiment, the overhangs are about 30 base pairs. In one embodiment, the overhangs are about 35 base pairs. In one embodiment, the overhangs are about 40 base pairs. In one embodiment, the overhangs are about 50 base pairs. In one embodiment, the overhangs are about 55 base pairs. In one embodiment, the overhangs are about 60 base pairs. In one embodiment, the overhangs are about 65 base pairs. In one embodiment, the overhangs are about 70 base pairs. In one embodiment, the overhangs are about 75 base pairs. In one embodiment, the overhangs are about 100 base pairs. In one embodiment, the overhangs are about 150 base pairs. In one embodiment, the overhangs are about 200 base pairs. In one embodiment, the overhangs are about 300 base pairs. In one embodiment, the overhangs are about 400 base pairs. In one embodiment, the overhangs are about 500 base pairs. The complementarity need not be 100% complementarity. For example, the complementary overhangs can be 95%, 96%, 97%, 98%, or 99% complementary to the overhangs of the cleaved DNA.

In some embodiments, the methods include inserting a donor polynucleotide into the genome of a cell. The donor sequence can be of any length, such as between 2 and 30,000 nucleotides in length (or any integer value therebetween), such as between 50 and 5,000 nucleotides in length, for example between about 100 and 1,000 nucleotides in length (or any integer there between), or about 200 and 500 nucleotides in length. Techniques for determining nucleic acid and amino acid sequence identity are known in the art.

Many of the embodiments disclosed in this section are described in combination with, or in the context of, fokI nuclease, or a nuclease-retaining fragment thereof; however, it should be understood that other nuclease proteins, or functional fragments thereof, could also be used in an analogous manner to form the described compositions and carryout the described methods. For example, mung bean nuclease, pancreatic DNAase I, micrococcal nuclease; yeast HO endonuclease; and other may be used in this context. (See, e.g., Linn et al. (eds.) Nucleases, Cold Spring Harbor Laboratory Press, 1993 and Schierling et al., Nucleic Acids Res. 2012 March; 40(6): 2623-2638.)

Kits incorporating the recombinant polynucleotides described herein are also described. These kits may further include one or more of a transfection reagent, a nucleofection reagent, a selection agent, or instructions for using the kit.

Modification of Genomic DNA

Described herein are methods of using the described polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs. One application for use with some of the compositions described herein is a method of modifying the genomic DNA of a cell by introducing into the cell a first polypeptide with a DNA-binding domain specific for a DNA sequence upstream of a genomic sequence of interest and a second polypeptide with a DNA-binding domain specific for a DNA sequence downstream from the genomic sequence of interest, wherein the first and second polypeptides mediate cleavage of the genomic DNA and excise a genomic sequence of interest, thereby modifying the genomic DNA of the cell.

One application for use with some of the compositions described herein is a method of modifying the genomic DNA of a cell by introducing into the cell a first polypeptide with a DNA-binding domain, having the sequence of SEQ ID NO: 7, specific for a DNA sequence upstream of a genomic sequence of interest and a second polypeptide with a DNA-binding domain, having the sequence of SEQ ID NO: 10, specific for a DNA sequence downstream from the genomic sequence of interest, wherein the first and second polypeptides mediate cleavage of the genomic DNA and excise a genomic sequence of interest, thereby modifying the genomic DNA of the cell.

One application for use with some of the compositions described herein is a method of modifying the genomic DNA of a cell by introducing into the cell a first polypeptide with a DNA-binding domain specific for a DNA sequence within the sequence of SEQ ID NO: 19 upstream of a genomic sequence of interest and a second polypeptide with a DNA-binding domain specific for a DNA sequence within the sequence of SEQ ID NO: 19 downstream from the genomic sequence of interest, wherein the first and second polypeptides mediate cleavage of the genomic DNA and excise a genomic sequence of interest, thereby modifying the genomic DNA of the cell.

Another application for use with some of the compositions described herein is a method of modifying the genomic DNA of a cell by introducing into the cell a first TALEN with a DNA-binding domain specific for a DNA sequence within human chromosome 13 that binds upstream of a genomic sequence of interest and a second TALEN with a DNA-binding domain specific for a DNA sequence within human chromosome 13 that binds downstream from the genomic sequence of interest, whereby the TALEN cleaves the genomic DNA and excises the genomic sequence of interest, thereby modifying the genomic DNA of the cell.

Another application for use with some of the compositions described herein is a method of modifying the genomic DNA of a cell by introducing into the cell a first TALEN with a DNA-binding domain specific for a DNA sequence within the CLYBL safe-harbor locus that binds upstream of a genomic sequence of interest and a second TALEN with a DNA-binding domain specific for a DNA sequence within the CLYBL safe-harbor locus that binds downstream from the genomic sequence of interest, whereby the TALEN cleaves the genomic DNA and excises the genomic sequence of interest, thereby modifying the genomic DNA of the cell.

One embodiment of the described method of modifying the genomic DNA of a cell involves introducing into the cell a first TALEN with a DNA-binding domain specific for a DNA sequence within intron 2 of the CLYBL safe-harbor locus that binds upstream of a genomic sequence of interest and a second TALEN with a DNA-binding domain specific for a DNA sequence within intron 2 of the CLYBL safe-harbor locus that binds downstream from the genomic sequence of interest, whereby the TALEN cleaves the genomic DNA and excises the genomic sequence of interest, thereby modifying the genomic DNA of the cell.

Another application for use with some of the compositions described herein is a method of modifying the genomic DNA of a cell by introducing into the cell a first TALEN with a DNA-binding domain specific for a DNA sequence within the sequence of SEQ ID NO: 19 that binds upstream of a genomic sequence of interest and a second TALEN with a DNA-binding domain specific for a DNA sequence within the sequence of SEQ ID NO: 19 that binds downstream from the genomic sequence of interest, whereby the TALEN cleaves the genomic DNA and excises the genomic sequence of interest, thereby modifying the genomic DNA of the cell.

Another application for use with some of the compositions described herein is a method of modifying the genomic DNA of a cell by introducing into the cell a first TALEN with a DNA-binding domain specific for a DNA sequence having the sequence of SEQ ID NO: 1 that binds upstream of a genomic sequence of interest and a second TALEN with a DNA-binding domain specific for a DNA sequence having the sequence of SEQ ID NO: 3 that binds downstream from the genomic sequence of interest, whereby the TALEN cleaves the genomic DNA and excises the genomic sequence of interest, thereby modifying the genomic DNA of the cell.

One embodiment of the method of modifying genomic DNA includes introducing into the cell a first TALEN, having the sequence of SEQ ID NO: 7, with a DNA-binding domain specific for a DNA sequence upstream of a genomic sequence of interest and a second TALEN with a DNA-binding domain specific for a DNA sequence downstream from the genomic sequence of interest, whereby the TALEN cleaves the genomic DNA and excises the genomic sequence of interest, thereby modifying the genomic DNA of the cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method of modifying genomic DNA includes introducing into the cell a first TALEN with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, whereby the TALEN cleaves the genomic DNA and excises the genomic sequence of interest, thereby modifying the genomic DNA of the cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method of modifying genomic DNA includes introducing into the cell a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, whereby the TALEN cleaves the genomic DNA and excises the genomic sequence of interest, thereby modifying the genomic DNA of the cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method of modifying genomic DNA includes introducing into the cell a first TALEN, having the sequence of SEQ ID NO: 8, with a DNA-binding domain specific for a DNA sequence upstream of a genomic sequence of interest and a second TALEN with a DNA-binding domain specific for a DNA sequence downstream from the genomic sequence of interest, whereby the TALEN cleaves the genomic DNA and excises the genomic sequence of interest, thereby modifying the genomic DNA of the cell.

One embodiment of the method of modifying genomic DNA includes introducing into the cell a first TALEN with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, whereby the TALEN cleaves the genomic DNA and excises the genomic sequence of interest, thereby modifying the genomic DNA of the cell.

One embodiment of the method of modifying genomic DNA includes introducing into the cell a first TALEN, having the sequence of SEQ ID NO: 8, with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, whereby the TALEN cleaves the genomic DNA and excises the genomic sequence of interest, thereby modifying the genomic DNA of the cell.

Another application for use with some of the compositions described herein is a method of modifying the genomic DNA of a cell by introducing into the cell a first TALEN with a DNA-binding domain specific for a DNA sequence within human chromosome 13 that binds to the sense strand of DNA upstream of a genomic sequence of interest and a second TALEN with a DNA-binding domain specific for a DNA sequence within human chromosome 13 that binds to the antisense strand of DNA downstream from the genomic sequence of interest, whereby the TALEN cleaves the genomic DNA and excises the genomic sequence of interest, thereby modifying the genomic DNA of the cell.

Another application for use with some of the compositions described herein is a method of modifying the genomic DNA of a cell by introducing into the cell a first TALEN with a DNA-binding domain specific for a DNA sequence within the CLYBL safe-harbor locus that binds to the sense strand of DNA upstream of a genomic sequence of interest and a second TALEN with a DNA-binding domain specific for a DNA sequence within the CLYBL safe-harbor locus that binds to the antisense strand of DNA downstream from the genomic sequence of interest, whereby the TALEN cleaves the genomic DNA and excises the genomic sequence of interest, thereby modifying the genomic DNA of the cell.

One embodiment of the described method of modifying the genomic DNA of a cell involves introducing into the cell a first TALEN with a DNA-binding domain specific for a DNA sequence within intron 2 of the CLYBL safe-harbor locus that binds to the sense strand of DNA upstream of a genomic sequence of interest and a second TALEN with a DNA-binding domain specific for a DNA sequence within intron 2 of the CLYBL safe-harbor locus that binds to the antisense strand of DNA downstream from the genomic sequence of interest, whereby the TALEN cleaves the genomic DNA and excises the genomic sequence of interest, thereby modifying the genomic DNA of the cell.

Another application for use with some of the compositions described herein is a method of modifying the genomic DNA of a cell by introducing into the cell a first TALEN with a DNA-binding domain specific for a DNA sequence within the sequence of SEQ ID NO: 19 that binds to the sense strand of DNA upstream of a genomic sequence of interest and a second TALEN with a DNA-binding domain specific for a DNA sequence within the sequence of SEQ ID NO: 19 that binds to the antisense strand of DNA downstream from the genomic sequence of interest, whereby the TALEN cleaves the genomic DNA and excises the genomic sequence of interest, thereby modifying the genomic DNA of the cell.

Another application for use with some of the compositions described herein is a method of modifying the genomic DNA of a cell by introducing into the cell a first TALEN with a DNA-binding domain specific for a DNA sequence having the sequence of SEQ ID NO: 1 that binds to the sense strand of DNA upstream of a genomic sequence of interest and a second TALEN with a DNA-binding domain specific for a DNA sequence having the sequence of SEQ ID NO: 3 that binds to the antisense strand of DNA downstream from the genomic sequence of interest, whereby the TALEN cleaves the genomic DNA and excises the genomic sequence of interest, thereby modifying the genomic DNA of the cell.

One embodiment of the method of modifying genomic DNA includes introducing into the cell a first TALEN, having the sequence of SEQ ID NO: 7, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, whereby the TALEN cleaves the genomic DNA and excises the genomic sequence of interest, thereby modifying the genomic DNA of the cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method of modifying genomic DNA includes introducing into the cell a first TALEN with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, whereby the TALEN cleaves the genomic DNA and excises the genomic sequence of interest, thereby modifying the genomic DNA of the cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method of modifying genomic DNA includes introducing into the cell a first TALEN, having the sequence of SEQ ID NO: 7, with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, whereby the TALEN cleaves the genomic DNA and excises the genomic sequence of interest, thereby modifying the genomic DNA of the cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method of modifying genomic DNA includes introducing into the cell a first TALEN, having the sequence of SEQ ID NO: 8, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, whereby the TALEN cleaves the genomic DNA and excises the genomic sequence of interest, thereby modifying the genomic DNA of the cell.

One embodiment of the method of modifying genomic DNA includes introducing into the cell a first TALEN with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, whereby the TALEN cleaves the genomic DNA and excises the genomic sequence of interest, thereby modifying the genomic DNA of the cell.

One embodiment of the method of modifying genomic DNA includes introducing into the cell a first TALEN, having the sequence of SEQ ID NO: 8, with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, whereby the TALEN cleaves the genomic DNA and excises the genomic sequence of interest, thereby modifying the genomic DNA of the cell.

In accordance with the methods of modifying genomic DNA described in this section, it should be understood that broadly applicable further aspects of these methods may be carried out as needed or desired. In one embodiment the described methods can be carried out to cause polynucleotide excision in both copies of the same chromosome. In one embodiment the described methods can be carried out using nucleofection of a polynucleotide or vectors encoding the polypeptides or TALENs used with these methods. In a particular embodiment, nucleofection may be carried out using a Nucleofector™ apparatus. In some embodiments, the nucleofection provides a transfection efficiency of at least about 60%, at least about 65%, at least about 70%, at least about 75%, at least about 80%, at least about 85%, at least about 90%, or at least about 95%. In specific non-limiting example, the transfection efficiency is at least about 80%, at least about 85%, at least about 90%, at least about 95%, at least about 96%, about 97%, about 98% or about 99%. In some embodiments the step of introducing a first polypeptide or TALEN into a cell involves transfecting the cell with a polynucleotide encoding the polypeptide or TALEN. In some embodiments the step of introducing a second polypeptide or TALEN into a cell involves transfecting the cell with a polynucleotide encoding the polypeptide or TALEN. In some embodiments a single vector may be used to transfect a cell with polynucleotides that encode an upstream TALEN and the nucleic acid encoding the downstream TALEN. The methods described in the section are useful with a variety of cell types, including embryonic stem cells, somatic cells, iPS cells, autologous cells of a subject, and particular cell types generally known to exist in mammals.

Many of the embodiments disclosed in this section are described in combination with, or in the context of, fokI nuclease, or a nuclease-retaining fragment thereof; however, it should be understood that other nuclease proteins, or functional fragments thereof, could also be used in an analogous manner to form the described compositions and carryout the described methods. For example, mung bean nuclease, pancreatic DNAase I, micrococcal nuclease; yeast HO endonuclease; and others may be used in this context. (See, e.g., Linn et al. (eds.) Nucleases, Cold Spring Harbor Laboratory Press, 1993 and Schierling et al., Nucleic Acids Res. 2012 March; 40(6): 2623-2638.)

Insertion of a Sequence of Interest into Genomic DNA

Provided herein are methods of using the described polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs for inserting a polynucleotide into the genome of a cell. One embodiment of the described method is carried out by introducing into a cell a first polypeptide with a DNA-binding domain specific for a DNA sequence upstream of a genomic sequence of interest, a second polypeptide with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA, providing for the introduction of the donor polynucleotide into the genome of the cell. Particular loci of interest for inserting a polynucleotide into the genome of a cell are safe harbor loci, as described herein.

One embodiment of the described method is carried out by introducing into a cell a first polypeptide with a DNA-binding domain, having the sequence of SEQ ID NO: 7, specific for a DNA sequence upstream of a genomic sequence of interest, a second polypeptide with a DNA-binding domain, having the sequence of SEQ ID NO: 10, specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA, providing for the introduction of the donor polynucleotide into the genome of the cell.

One embodiment of the described method is carried out by introducing into a cell a first polypeptide with a DNA-binding domain specific for a DNA sequence within the sequence of SEQ ID NO: 19 upstream of a genomic sequence of interest, a second polypeptide with a DNA-binding domain specific for a DNA sequence within a sequence complementary to the sequence of SEQ ID NO: 19 downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA, providing for the introduction of the donor polynucleotide into the genome of the cell.

One embodiment of the described method is carried out by introducing into a cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Described herein are methods of using the described polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs. One application for use with some of the compositions described herein is a method of inserting a polynucleotide into the genome of a cell by introducing into the cell a first TALEN with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Another application for use with some of the compositions described herein is a method of inserting a polynucleotide into the genome of a cell by introducing into the cell a first TALEN with a DNA-binding domain specific for a DNA sequence within human chromosome 13 that binds upstream of a genomic sequence of interest and a second TALEN with a DNA-binding domain specific for a DNA sequence within human chromosome 13 that binds downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Another application for use with some of the compositions described herein is a method of inserting a polynucleotide into the genome of a cell by introducing into the cell a first TALEN with a DNA-binding domain specific for a DNA sequence within the CLYBL safe-harbor locus that binds upstream of a genomic sequence of interest and a second TALEN with a DNA-binding domain specific for a DNA sequence within the CLYBL safe-harbor locus that binds downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

One embodiment of the described method of inserting a polynucleotide into the genome of a cell involves introducing into the cell a first TALEN with a DNA-binding domain specific for a DNA sequence within intron 2 of the CLYBL safe-harbor locus that binds upstream of a genomic sequence of interest and a second TALEN with a DNA-binding domain specific for a DNA sequence within intron 2 of the CLYBL safe-harbor locus that binds downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Another application for use with some of the compositions described herein is a method of inserting a polynucleotide into the genome of a cell by introducing into the cell a first TALEN with a DNA-binding domain specific for a DNA sequence within the sequence of SEQ ID NO: 19 that binds upstream of a genomic sequence of interest and a second TALEN with a DNA-binding domain specific for a DNA sequence within the sequence of SEQ ID NO: 19 that binds downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Another application for use with some of the compositions described herein is a method of inserting a polynucleotide into the genome of a cell by introducing into the cell a first TALEN with a DNA-binding domain specific for a DNA sequence having the sequence of SEQ ID NO: 1 that binds upstream of a genomic sequence of interest and a second TALEN with a DNA-binding domain specific for a DNA sequence having the sequence of SEQ ID NO: 3 that binds downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

One embodiment of the method of inserting a polynucleotide into the genome of a cell includes introducing into the cell a first TALEN, having the sequence of SEQ ID NO: 7, with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method of inserting a polynucleotide into the genome of a cell includes introducing into the cell a first TALEN with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method of inserting a polynucleotide into the genome of a cell includes introducing into the cell a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method of inserting a polynucleotide into the genome of a cell includes introducing into the cell a first TALEN, having the sequence of SEQ ID NO: 8, with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

One embodiment of the method of inserting a polynucleotide into the genome of a cell includes introducing into the cell a first TALEN with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

One embodiment of the method of inserting a polynucleotide into the genome of a cell includes introducing into the cell a first TALEN, having the sequence of SEQ ID NO: 8, with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Another application for use with some of the compositions described herein is a method of inserting a polynucleotide into the genome of a cell by introducing into the cell a first TALEN with a DNA-binding domain specific for a DNA sequence within human chromosome 13 that binds to the sense strand of DNA upstream of a genomic sequence of interest and a second TALEN with a DNA-binding domain specific for a DNA sequence within human chromosome 13 that binds to the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Another application for use with some of the compositions described herein is a method of inserting a polynucleotide into the genome of a cell by introducing into the cell a first TALEN with a DNA-binding domain specific for a DNA sequence within the CLYBL safe-harbor locus that binds to the sense strand of DNA upstream of a genomic sequence of interest and a second TALEN with a DNA-binding domain specific for a DNA sequence within the CLYBL safe-harbor locus that binds to the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

One embodiment of the described method of inserting a polynucleotide into the genome of a cell involves introducing into the cell a first TALEN with a DNA-binding domain specific for a DNA sequence within intron 2 of the CLYBL safe-harbor locus that binds to the sense strand of DNA upstream of a genomic sequence of interest and a second TALEN with a DNA-binding domain specific for a DNA sequence within intron 2 of the CLYBL safe-harbor locus that binds to the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Another application for use with some of the compositions described herein is a method of inserting a polynucleotide into the genome of a cell by introducing into the cell a first TALEN with a DNA-binding domain specific for a DNA sequence within the sequence of SEQ ID NO: 19 that binds to the sense strand of DNA upstream of a genomic sequence of interest and a second TALEN with a DNA-binding domain specific for a DNA sequence within the sequence of SEQ ID NO: 19 that binds to the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

Another application for use with some of the compositions described herein is a method of inserting a polynucleotide into the genome of a cell by introducing into the cell a first TALEN with a DNA-binding domain specific for a DNA sequence having the sequence of SEQ ID NO: 1 that binds to the sense strand of DNA upstream of a genomic sequence of interest and a second TALEN with a DNA-binding domain specific for a DNA sequence having the sequence of SEQ ID NO: 3 that binds to the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

One embodiment of the method of inserting a polynucleotide into the genome of a cell includes introducing into the cell a first TALEN, having the sequence of SEQ ID NO: 7, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method of inserting a polynucleotide into the genome of a cell includes introducing into the cell a first TALEN with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method of inserting a polynucleotide into the genome of a cell includes introducing into the cell a first TALEN, having the sequence of SEQ ID NO: 7, with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method of inserting a polynucleotide into the genome of a cell includes introducing into the cell a first TALEN, having the sequence of SEQ ID NO: 8, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

One embodiment of the method of inserting a polynucleotide into the genome of a cell includes introducing into the cell a first TALEN with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

One embodiment of the method of inserting a polynucleotide into the genome of a cell includes introducing into the cell a first TALEN, having the sequence of SEQ ID NO: 8, with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single-stranded or double-stranded donor polynucleotide with sense and/or antisense strand polynucleotide overhangs that are complementary to corresponding polynucleotide overhangs of genomic DNA cleaved by the introduced TALENs at a genomic insertion site, wherein said complementary overhangs facilitate homologous recombination of the donor polynucleotide with the cleaved genomic DNA, providing for the introduction of the donor polynucleotide into the genome of the cell.

In accordance with the methods of inserting a polynucleotide into the genome of a cell described in this section it should be understood that broadly applicable further aspects of these methods may be carried out as needed or desired. As should be understood by those skilled in the art, the methods described in this section may be useful for treating diseases conditions that may be improved by overexpression, or in some instances regulated expression, of a particular gene. Examples of gene products suitable for this purpose include CYBB (cytochrome b-245, beta polypeptide), CYBA (cytochrome b-245 alpha polypeptide), NCF1 (neutrophil cytosolic factor 1) and NCF2 (neutrophil cytosolic factor 2) for chronic granulomatous disease (CGD); HBB (hemoglobin, beta) for sickle cell disease and beta-thalassemia; IL2RG (interleukin 2 receptor, gamma) and ADA (adenosine deaminase) for severe combined immunodeficiency (SCID); WAS (wiskott-aldrich syndrome) for wiskott-aldrich syndrome; ABCD1 (ATP-binding cassette, sub-family D, member 1) for X-linked adrenoleukodystrophy (X-ALD); PSMB8 (proteasome subunit, beta type, 8), PSMB4 (proteasome subunit, beta type, 4), PSMB9 (proteasome subunit, beta type, 9), PSMA3 (proteasome subunit, alpha type, 3) for Chronic Atypical Neutrophilic Dermatosis with Lipodystrophy and Elevated Temperature (CANDLE).

In one embodiment the described methods can be carried out to cause polynucleotide excision in both copies of the same chromosome. In one embodiment the described methods can be carried out using nucleofection of a polynucleotide or vectors encoding the polypeptides or TALENs used with these methods. In a particular embodiment, nucleofection may be carried out using a Nucleofector™ apparatus. In some embodiments, the nucleofection provides a transfection efficiency of at least about 60%, at least about 65%, at least about 70%, at least about 75%, at least about 80%, at least about 85%, at least about 90%, or at least about 95%. In specific non-limiting example, the transfection efficiency is at least about 80%, at least about 85%, at least about 90%, at least about 95%, at least about 96%, about 97%, about 98% or about 99%. In some embodiments the step of introducing a first polypeptide or TALEN into a cell involves transfecting the cell with a polynucleotide encoding the polypeptide or TALEN. In some embodiments the step of introducing a second polypeptide or TALEN into a cell involves transfecting the cell with a polynucleotide encoding the polypeptide or TALEN. In some embodiments a single vector may be used to transfect a cell with polynucleotides that encode an upstream TALEN and the nucleic acid encoding the downstream TALEN. The methods described in the section are useful with a variety of cell types, including embryonic stem cells, somatic cells, iPS cells, autologous cells of a subject, and particular cell types generally known to exist in mammals. In some embodiments the stem cells used to carry out the described methods may be "long term" stem cells, or iPSCs, capable of dividing in culture for at least 15 cell divisions, such as at least 15, 20, 25, 30, 35, 40, 45 or 50 cell divisions while retaining the properties of a stem cell or iPSC.

In some embodiments of this section, the donor polynucleotide is a single-stranded or double-stranded donor polynucleotide with sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, such that the polynucleotide is introduced into the genome of the cell. In some embodiments, the overhangs are from about 15 base pairs to about 500 base pairs. In some embodiments, the overhangs are at least 15 nucleotides in length, such as 20, 30, 40, 50, 60, 70, 80, 90, 100, 200, 300, 400, 500, 600, 700, 800, 900, or 1,000 base pairs. In one embodiment the overhangs are at least 15 base pairs. In one embodiment, the overhangs are about 15 base pairs. In one embodiment, the overhangs are about 25 base pairs. In one embodiment, the overhangs are about 30 base pairs. In one embodiment, the overhangs are about 35 base pairs. In one embodiment, the overhangs are about 40 base pairs. In one embodiment, the overhangs are about 50 base pairs. In one embodiment, the overhangs are about 55 base pairs. In one embodiment, the overhangs are about 60 base pairs. In one embodiment, the overhangs are about 65 base pairs. In one embodiment, the overhangs are about 70 base pairs. In one embodiment, the overhangs are about 75 base pairs. In one embodiment, the overhangs are about 100 base pairs. In one embodiment, the overhangs are about 150 base pairs. In one embodiment, the overhangs are about 200 base pairs. In one embodiment, the overhangs are about 300 base pairs. In one embodiment, the overhangs are about 400 base pairs. In one embodiment, the overhangs are about 500 base pairs. The complementarity need not be 100% complementarity. For example, the complementary overhangs can be 95%, 96%, 97%, 98%, or 99% complementary to the overhangs of the cleaved DNA.

In some embodiments, the methods include inserting a donor polynucleotide into the genome of a cell. The donor sequence can be of any length, such as between 2 and 30,000 nucleotides in length (or any integer value therebetween), such as between 50 and 5,000 nucleotides in length, for example between about 100 and 1,000 nucleotides in length (or any integer there between), or about 200 and 500 nucleotides in length. Techniques for determining nucleic acid and amino acid sequence identity are known in the art.

Many of the embodiments disclosed in this section are described in combination with, or in the context of, fokI nuclease, or a nuclease-retaining fragment thereof; however, it should be understood that other nuclease proteins, or functional fragments thereof, could also be used in an analogous manner to form the described compositions and carryout the described methods. For example, mung bean nuclease, pancreatic DNAase I, micrococcal nuclease; yeast HO endonuclease; and other may be used in this context. (See, e.g., Linn et al. (eds.) Nucleases, Cold Spring Harbor Laboratory Press, 1993 and Schierling et al., Nucleic Acids Res. 2012 March; 40(6): 2623-2638.)

Production of iPS Cells

An induced pluripotent stem cell may also be produced from a somatic cell using the methods and compositions described herein. Accordingly, provided herein are methods of using the described polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs for. Particular loci of interest for inserting a polynucleotide into the genome of a cell are safe harbor loci, as described herein.

One embodiment of the described method for producing an iPS cell from a somatic cell is carried out by introducing into a somatic cell a first polypeptide with a DNA-binding domain specific for a DNA sequence upstream of a genomic sequence of interest, a second polypeptide with a DNA-binding domain specific for a DNA sequence downstream from the genomic sequence of interest, and a single-stranded or double-stranded donor polynucleotide encoding one or more factors sufficient to convert a somatic cell into a pluripotent stem cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the somatic cell into an induced pluripotent stem cell.

One embodiment of the described method for producing an iPS cell from a somatic cell is carried out by introducing into a somatic cell a first polypeptide with a DNA-binding domain, having the sequence of SEQ ID NO: 7, specific for a DNA sequence upstream of a genomic sequence of interest, a second polypeptide with a DNA-binding domain, having the sequence of SEQ ID NO: 10, specific for a DNA sequence downstream from the genomic sequence of interest, and a single-stranded or double-stranded donor polynucleotide encoding one or more factors sufficient to convert a somatic cell into a pluripotent stem cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the somatic cell into an induced pluripotent stem cell.

One embodiment of the described method for producing an iPS cell from a somatic cell is carried out by introducing into a somatic cell a first polypeptide with a DNA-binding domain specific for a DNA sequence within the sequence of SEQ ID NO: 19 upstream of a genomic sequence of interest, a second polypeptide with a DNA-binding domain specific for a DNA sequence within a sequence complementary to the sequence of SEQ ID NO: 19 downstream from the genomic sequence of interest, and a single-stranded or double-stranded donor polynucleotide encoding one or more factors sufficient to convert a somatic cell into a pluripotent stem cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the somatic cell into an induced pluripotent stem cell.

Another such method involves introducing into a somatic cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One application for use with some of the compositions described herein is a method for producing an iPS cell from a somatic cell by introducing into the somatic cell a first TALEN with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Another application for use with some of the compositions described herein is a method for producing an iPS cell from a somatic cell by introducing into the somatic cell a first TALEN with a DNA-binding domain specific for a DNA sequence within human chromosome 13 that binds upstream of a genomic sequence of interest and a second TALEN with a DNA-binding domain specific for a DNA sequence within human chromosome 13 that binds downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Another application for use with some of the compositions described herein is a method for producing an iPS cell from a somatic cell by introducing into the somatic cell a first TALEN with a DNA-binding domain specific for a DNA sequence within the CLYBL safe-harbor locus that binds upstream of a genomic sequence of interest and a second TALEN with a DNA-binding domain specific for a DNA sequence within the CLYBL safe-harbor locus that binds downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One embodiment of the described method for producing an iPS cell from a somatic cell by introducing into the somatic cell a first TALEN with a DNA-binding domain specific for a DNA sequence within intron 2 of the CLYBL safe-harbor locus that binds upstream of a genomic sequence of interest and a second TALEN with a DNA-binding domain specific for a DNA sequence within intron 2 of the CLYBL safe-harbor locus that binds downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Another application for use with some of the compositions described herein is a method for producing an iPS cell from a somatic cell by introducing into the somatic cell a first TALEN with a DNA-binding domain specific for a DNA sequence within the sequence of SEQ ID NO: 19 that binds upstream of a genomic sequence of interest and a second TALEN with a DNA-binding domain specific for a DNA sequence within the sequence of SEQ ID NO: 19 that binds downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Another application for use with some of the compositions described herein is a method for producing an iPS cell from a somatic cell by introducing into the somatic cell a first TALEN with a DNA-binding domain specific for a DNA sequence having the sequence of SEQ ID NO: 1 that binds upstream of a genomic sequence of interest and a second TALEN with a DNA-binding domain specific for a DNA sequence having the sequence of SEQ ID NO: 3 that binds downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One embodiment of the method for producing an iPS cell from a somatic cell includes introducing into the somatic cell a first TALEN, having the sequence of SEQ ID NO: 7, with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method for producing an iPS cell from a somatic cell includes introducing into the somatic cell a first TALEN with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method for producing an iPS cell from a somatic cell includes introducing into the somatic cell a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method for producing an iPS cell from a somatic cell includes introducing into the somatic cell a first TALEN, having the sequence of SEQ ID NO: 8, with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One embodiment of the method for producing an iPS cell from a somatic cell includes introducing into the somatic cell a first TALEN with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One embodiment of the method for producing an iPS cell from a somatic cell includes introducing into the somatic cell a first TALEN, having the sequence of SEQ ID NO: 8, with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Another application for use with some of the compositions described herein is a method for producing an iPS cell from a somatic cell by introducing into the somatic cell a first TALEN with a DNA-binding domain specific for a DNA sequence within human chromosome 13 that binds to the sense strand of DNA upstream of a genomic sequence of interest and a second TALEN with a DNA-binding domain specific for a DNA sequence within human chromosome 13 that binds to the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Another application for use with some of the compositions described herein is a method for producing an iPS cell from a somatic cell by introducing into the somatic cell a first TALEN with a DNA-binding domain specific for a DNA sequence within the CLYBL safe-harbor locus that binds to the sense strand of DNA upstream of a genomic sequence of interest and a second TALEN with a DNA-binding domain specific for a DNA sequence within the CLYBL safe-harbor locus that binds to the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One embodiment of the described method for producing an iPS cell from a somatic cell by introducing into the somatic cell a first TALEN with a DNA-binding domain specific for a DNA sequence within intron 2 of the CLYBL safe-harbor locus that binds to the sense strand of DNA upstream of a genomic sequence of interest and a second TALEN with a DNA-binding domain specific for a DNA sequence within intron 2 of the CLYBL safe-harbor locus that binds to the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Another application for use with some of the compositions described herein is a method for producing an iPS cell from a somatic cell by introducing into the somatic cell a first TALEN with a DNA-binding domain specific for a DNA sequence within the sequence of SEQ ID NO: 19 that binds to the sense strand of DNA upstream of a genomic sequence of interest and a second TALEN with a DNA-binding domain specific for a DNA sequence within the sequence of SEQ ID NO: 19 that binds to the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

Another application for use with some of the compositions described herein is a method for producing an iPS cell from a somatic cell by introducing into the somatic cell a first TALEN with a DNA-binding domain specific for a DNA sequence having the sequence of SEQ ID NO: 1 that binds to the sense strand of DNA upstream of a genomic sequence of interest and a second TALEN with a DNA-binding domain specific for a DNA sequence having the sequence of SEQ ID NO: 3 that binds to the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One embodiment of the method for producing an iPS cell from a somatic cell includes introducing into the somatic cell a first TALEN, having the sequence of SEQ ID NO: 7, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method for producing an iPS cell from a somatic cell includes introducing into the somatic cell a first TALEN with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method for producing an iPS cell from a somatic cell includes introducing into the somatic cell a first TALEN, having the sequence of SEQ ID NO: 7, with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method for producing an iPS cell from a somatic cell includes introducing into the somatic cell a first TALEN, having the sequence of SEQ ID NO: 8, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One embodiment of the method for producing an iPS cell from a somatic cell includes introducing into the somatic cell a first TALEN with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

One embodiment of the method for producing an iPS cell from a somatic cell includes introducing into the somatic cell a first TALEN, having the sequence of SEQ ID NO: 8, with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single-stranded or double-stranded donor polynucleotide encoding one or more factors sufficient to convert a somatic cell into a pluripotent stem cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the somatic cell into an induced pluripotent stem cell.

In accordance with the methods for producing an iPS cell from a somatic cell described in this section it should be understood that broadly applicable further aspects of these methods may be carried out as needed or desired. In one embodiment the described methods can be carried out to cause a donor polynucleotide encoding one or more factors sufficient to convert a somatic cell into a pluripotent stem cell to be inserted into both copies of the same chromosome of a somatic cell. Factors sufficient for producing an iPS cell from a somatic cell applicable to the methods discussed include but are not limited to of Oct-3/4, certain members of the Sox gene family (Sox1, Sox2, Sox3, and Sox15, Klf family members (Klf1, Klf2, Klf4, and Klf5), factors of the Myc family (c-myc, L-myc, and N-myc), Nanog, and LIN28, as defined by current knowledge in the art. Other such factors adequate for this purpose that are known in the art should be considered within the scope of this disclosure. These factors may be used alone or in combination with one another to cause a somatic cell to become an iPS cell due to their expression in the cell. In one embodiment the described methods can be carried out using nucleofection of a polynucleotide or vectors encoding the polypeptides or TALENs used with these methods. In a particular embodiment, nucleofection may be carried out using a Nucleofector™ apparatus. In some embodiments, the nucleofection provides a transfection efficiency of at least about 60%, at least about 65%, at least about 70%, at least about 75%, at least about 80%, at least about 85%, at least about 90%, or at least about 95%. In specific non-limiting example, the transfection efficiency is at least about 80%, at least about 85%, at least about 90%, at least about 95%, at least about 96%, about 97%, about 98% or about 99%. In some embodiments the step of introducing a first polypeptide or TALEN into a somatic cell involves transfecting the cell with a polynucleotide encoding the polypeptide or TALEN. In some embodiments the step of introducing a second polypeptide or TALEN into a somatic cell involves transfecting the cell with a polynucleotide encoding the polypeptide or TALEN. In some embodiments a single vector may be used to transfect a somatic cell with polynucleotides that encode an upstream TALEN and the nucleic acid encoding the downstream TALEN. The methods described in the section are useful with a variety of somatic cell types, including, autologous cells of a subject, and particular somatic cell types generally known to exist in mammals.

In some embodiments of this section, the donor polynucleotide is a single-stranded or double-stranded donor polynucleotide with sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, such that the polynucleotide is introduced into the genome of the cell. In some embodiments, the overhangs are from about 15 base pairs to about 500 base pairs. In some embodiments, the overhangs are at least 15 nucleotides in length, such as 20, 30, 40, 50, 60, 70, 80, 90, 100, 200, 300, 400, 500, 600, 700, 800, 900, or 1,000 base pairs. In one embodiment the overhangs are at least 15 base pairs. In one embodiment, the overhangs are about 15 base pairs. In one embodiment, the overhangs are about 25 base pairs. In one embodiment, the overhangs are about 30 base pairs. In one embodiment, the overhangs are about 35 base pairs. In one embodiment, the overhangs are about 40 base pairs. In one embodiment, the overhangs are about 50 base pairs. In one embodiment, the overhangs are about 55 base pairs. In one embodiment, the overhangs are about 60 base pairs. In one embodiment, the overhangs are about 65 base pairs. In one embodiment, the overhangs are about 70 base pairs. In one embodiment, the overhangs are about 75 base pairs. In one embodiment, the overhangs are about 100 base pairs. In one embodiment, the overhangs are about 150 base pairs. In one embodiment, the overhangs are about 200 base pairs. In one embodiment, the overhangs are about 300 base pairs. In one embodiment, the overhangs are about 400 base pairs. In one embodiment, the overhangs are about 500 base pairs. The complementarity need not be 100% complementarity. For example, the complementary overhangs can be 95%, 96%, 97%, 98%, or 99% complementary to the overhangs of the cleaved DNA.

In some embodiments, the methods include inserting a donor polynucleotide into the genome of a cell. The donor sequence can be of any length, such as between 2 and 30,000 nucleotides in length (or any integer value therebetween), such as between 50 and 5,000 nucleotides in length, for example between about 100 and 1,000 nucleotides in length (or any integer there between), or about 200 and 500 nucleotides in length. Techniques for determining nucleic acid and amino acid sequence identity are known in the art.

Many of the embodiments disclosed in this section are described in combination with, or in the context of, fokI nuclease, or a nuclease-retaining fragment thereof; however, it should be understood that other nuclease proteins, or functional fragments thereof, could also be used in an analogous manner to form the described compositions and carryout the described methods. For example, mung bean nuclease, pancreatic DNAase I, micrococcal nuclease; yeast HO endonuclease; and other may be used in this context. (See, e.g., Linn et al. (eds.) Nucleases, Cold Spring Harbor Laboratory Press, 1993 and Schierling et al., Nucleic Acids Res. 2012 March; 40(6): 2623-2638.)

Differentiation of iPS Cells

An induced pluripotent stem cell may also be caused to differentiate into a lineage-specific cell using methods and compositions described herein. Accordingly, provided herein are methods of using the described polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs for causing an iPS cell to differentiate into a lineage-specific cell. In some embodiments the iPSCs used to carry out the described methods may be "long term" iPSCs that are capable of dividing in culture for at least 15 cell divisions, such as at least 15, 20, 25, 30, 35, 40, 45 or 50 cell divisions while retaining the properties of the iPSC.

One embodiment of the described method for causing an iPS cell to differentiate into a lineage-specific cell is carried out by introducing into an iPS cell a first polypeptide with a DNA-binding domain specific for a DNA sequence upstream of a genomic sequence of interest, a second polypeptide with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the iPS cell into a lineage-specific cell.

One embodiment of the described method for causing an iPS cell to differentiate into a lineage-specific cell is carried out by introducing into an iPS cell a first polypeptide with a DNA-binding domain specific for a DNA sequence upstream of a genomic sequence of interest, a second polypeptide with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the iPS cell into a lineage-specific cell.

One embodiment of the described method for causing an iPS cell to differentiate into a lineage-specific cell is carried out by introducing into an iPS cell a first polypeptide with a DNA-binding domain, having the sequence of SEQ ID NO: 7, specific for a DNA sequence upstream of a genomic sequence of interest, a second polypeptide with a DNA-binding domain, having the sequence of SEQ ID NO: 10, specific for a DNA sequence downstream from the genomic sequence of interest, and a single-stranded or double-stranded donor polynucleotide encoding one or more factors sufficient to differentiate an iPS cell into a lineage-specific cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the iPS cell into a lineage-specific cell.

One embodiment of the described method for causing an iPS cell to differentiate into a lineage-specific cell is carried out by introducing into an iPS cell a first polypeptide with a DNA-binding domain specific for a DNA sequence within the sequence of SEQ ID NO: 19 upstream of a genomic sequence of interest, a second polypeptide with a DNA-binding domain specific for a DNA sequence within a sequence complementary to the sequence of SEQ ID NO: 19 downstream from the genomic sequence of interest, and a single-stranded or double-stranded donor polynucleotide encoding one or more factors sufficient to differentiate an iPS cell into a lineage-specific cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the iPS cell into a lineage-specific cell.

Another such method involves introducing into an iPS cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One application for use with some of the compositions described herein is a method for causing an iPS cell to differentiate into a lineage-specific cell by introducing into the iPS cell a first TALEN with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

Another application for use with some of the compositions described herein is a method for causing an iPS cell to differentiate into a lineage-specific cell by introducing into the iPS cell a first TALEN with a DNA-binding domain specific for a DNA sequence within human chromosome 13 that binds upstream of a genomic sequence of interest and a second TALEN with a DNA-binding domain specific for a DNA sequence within human chromosome 13 that binds downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

Another application for use with some of the compositions described herein is a method for causing an iPS cell to differentiate into a lineage-specific cell by introducing into the iPS cell a first TALEN with a DNA-binding domain specific for a DNA sequence within the CLYBL safe-harbor locus that binds upstream of a genomic sequence of interest and a second TALEN with a DNA-binding domain specific for a DNA sequence within the CLYBL safe-harbor locus that binds downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One embodiment of the described method for causing an iPS cell to differentiate into a lineage-specific cell is by introducing into the iPS cell a first TALEN with a DNA-binding domain specific for a DNA sequence within intron 2 of the CLYBL safe-harbor locus that binds upstream of a genomic sequence of interest and a second TALEN with a DNA-binding domain specific for a DNA sequence within intron 2 of the CLYBL safe-harbor locus that binds downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

Another application for use with some of the compositions described herein is a method for causing an iPS cell to differentiate into a lineage-specific cell by introducing into the iPS cell a first TALEN with a DNA-binding domain specific for a DNA sequence within the sequence of SEQ ID NO: 19 that binds upstream of a genomic sequence of interest and a second TALEN with a DNA-binding domain specific for a DNA sequence within the sequence of SEQ ID NO: 19 that binds downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

Another application for use with some of the compositions described herein is a method for causing an iPS cell to differentiate into a lineage-specific cell by introducing into the iPS cell a first TALEN with a DNA-binding domain specific for a DNA sequence having the sequence of SEQ ID NO: 1 that binds upstream of a genomic sequence of interest and a second TALEN with a DNA-binding domain specific for a DNA sequence having the sequence of SEQ ID NO: 3 that binds downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One embodiment of the method for causing an iPS cell to differentiate into a lineage-specific cell includes introducing into the iPS cell a first TALEN, having the sequence of SEQ ID NO: 7, with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method for causing an iPS cell to differentiate into a lineage-specific cell includes introducing into the iPS cell a first TALEN with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method for causing an iPS cell to differentiate into a lineage-specific cell includes introducing into the iPS cell a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method for causing an iPS cell to differentiate into a lineage-specific cell includes introducing into the iPS cell a first TALEN, having the sequence of SEQ ID NO: 8, with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One embodiment of the method for causing an iPS cell to differentiate into a lineage-specific cell includes introducing into the iPS cell a first TALEN with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One embodiment of the method for causing an iPS cell to differentiate into a lineage-specific cell includes introducing into the iPS cell a first TALEN, having the sequence of SEQ ID NO: 8, with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

Another application for use with some of the compositions described herein is a method for causing an iPS cell to differentiate into a lineage-specific cell by introducing into the iPS cell a first TALEN with a DNA-binding domain specific for a DNA sequence within human chromosome 13 that binds to the sense strand of DNA upstream of a genomic sequence of interest and a second TALEN with a DNA-binding domain specific for a DNA sequence within human chromosome 13 that binds to the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

Another application for use with some of the compositions described herein is a method for causing an iPS cell to differentiate into a lineage-specific cell by introducing into the iPS cell a first TALEN with a DNA-binding domain specific for a DNA sequence within the CLYBL safe-harbor locus that binds to the sense strand of DNA upstream of a genomic sequence of interest and a second TALEN with a DNA-binding domain specific for a DNA sequence within the CLYBL safe-harbor locus that binds to the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One embodiment of the described method for causing an iPS cell to differentiate into a lineage-specific cell is by introducing into the iPS cell a first TALEN with a DNA-binding domain specific for a DNA sequence within intron 2 of the CLYBL safe-harbor locus that binds to the sense strand of DNA upstream of a genomic sequence of interest and a second TALEN with a DNA-binding domain specific for a DNA sequence within intron 2 of the CLYBL safe-harbor locus that binds to the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

Another application for use with some of the compositions described herein is a method for causing an iPS cell to differentiate into a lineage-specific cell by introducing into the iPS cell a first TALEN with a DNA-binding domain specific for a DNA sequence within the sequence of SEQ ID NO: 19 that binds to the sense strand of DNA upstream of a genomic sequence of interest and a second TALEN with a DNA-binding domain specific for a DNA sequence within the sequence of SEQ ID NO: 19 that binds to the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

Another application for use with some of the compositions described herein is a method for causing an iPS cell to differentiate into a lineage-specific cell by introducing into the iPS cell a first TALEN with a DNA-binding domain specific for a DNA sequence having the sequence of SEQ ID NO: 1 that binds to the sense strand of DNA upstream of a genomic sequence of interest and a second TALEN with a DNA-binding domain specific for a DNA sequence having the sequence of SEQ ID NO: 3 that binds to the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One embodiment of the method for causing an iPS cell to differentiate into a lineage-specific cell includes introducing into the iPS cell a first TALEN, having the sequence of SEQ ID NO: 7, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method for causing an iPS cell to differentiate into a lineage-specific cell includes introducing into the iPS cell a first TALEN with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method for causing an iPS cell to differentiate into a lineage-specific cell includes introducing into the iPS cell a first TALEN, having the sequence of SEQ ID NO: 7, with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method for causing an iPS cell to differentiate into a lineage-specific cell includes introducing into the iPS cell a first TALEN, having the sequence of SEQ ID NO: 8, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One embodiment of the method for causing an iPS cell to differentiate into a lineage-specific cell includes introducing into the iPS cell a first TALEN with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

One embodiment of the method for causing an iPS cell to differentiate into a lineage-specific cell includes introducing into the iPS cell a first TALEN, having the sequence of SEQ ID NO: 8, with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single-stranded or double-stranded donor polynucleotide encoding one or more factors sufficient to differentiate an iPS cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the iPS cell into a lineage-specific cell.

In accordance with the methods causing an iPS cell to differentiate into a lineage-specific cell described in this section it should be understood that broadly applicable further aspects of these methods may be carried out as needed or desired. In one embodiment the described methods can be carried out to cause a donor polynucleotide encoding one or more factors sufficient to differentiate an iPS cell into a lineage-specific cell to be inserted into both copies of the same chromosome of an iPS cell. Factors sufficient to differentiate an iPS cell into a lineage-specific cell applicable to the methods discussed include but are not limited to transforming growth factor beta (TGF-β), bone morphogenetic protein (BMP), NODAL, ACTIVIN, NOTCH, WNT, sonic hedgehog (SHH), JAK/STAT, and fibroblast growth factor (FGF) signaling pathway factors. These factors may be used alone or in combination with one another to cause an iPS cell to differentiate into a lineage-specific cell due to their expression in the cell. In one embodiment the described methods can be carried out using nucleofection of a polynucleotide or vectors encoding the polypeptides or TALENs used with these methods. In a particular embodiment, nucleofection may be carried out using a Nucleofector™ apparatus. In some embodiments, the nucleofection provides a transfection efficiency of at least about 60%, at least about 65%, at least about 70%, at least about 75%, at least about 80%, at least about 85%, at least about 90%, or at least about 95%. In specific non-limiting example, the transfection efficiency is at least about 80%, at least about 85%, at least about 90%, at least about 95%, at least about 96%, about 97%, about 98% or about 99%. In some embodiments the step of introducing a first polypeptide or TALEN into an iPS cell involves transfecting the cell with a polynucleotide encoding the polypeptide or TALEN. In some embodiments the step of introducing a second polypeptide or TALEN into an iPS cell involves transfecting the cell with a polynucleotide encoding the polypeptide or TALEN. In some embodiments a single vector may be used to transfect an iPS cell with polynucleotides that encode an upstream TALEN and the nucleic acid encoding the downstream TALEN. The methods described in the section are useful with a variety of an iPS cell types, including, autologous cells of a subject, and particular an iPS cell types generally known to exist in mammals.

In some embodiments of this section, the donor polynucleotide is a single-stranded or double-stranded donor polynucleotide with sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, such that the polynucleotide is introduced into the genome of the cell. In some embodiments, the overhangs are from about 15 base pairs to about 500 base pairs. In some embodiments, the overhangs are at least 15 nucleotides in length, such as 20, 30, 40, 50, 60, 70, 80, 90, 100, 200, 300, 400, 500, 600, 700, 800, 900, or 1,000 base pairs. In one embodiment the overhangs are at least 15 base pairs. In one embodiment, the overhangs are about 15 base pairs. In one embodiment, the overhangs are about 25 base pairs. In one embodiment, the overhangs are about 30 base pairs. In one embodiment, the overhangs are about 35 base pairs. In one embodiment, the overhangs are about 40 base pairs. In one embodiment, the overhangs are about 50 base pairs. In one embodiment, the overhangs are about 55 base pairs. In one embodiment, the overhangs are about 60 base pairs. In one embodiment, the overhangs are about 65 base pairs. In one embodiment, the overhangs are about 70 base pairs. In one embodiment, the overhangs are about 75 base pairs. In one embodiment, the overhangs are about 100 base pairs. In one embodiment, the overhangs are about 150 base pairs. In one embodiment, the overhangs are about 200 base pairs. In one embodiment, the overhangs are about 300 base pairs. In one embodiment, the overhangs are about 400 base pairs. In one embodiment, the overhangs are about 500 base pairs. The complementarity need not be 100% complementarity. For example, the complementary overhangs can be 95%, 96%, 97%, 98%, or 99% complementary to the overhangs of the cleaved DNA.

In some embodiments, the methods include inserting a donor polynucleotide into the genome of a cell. The donor sequence can be of any length, such as between 2 and 30,000 nucleotides in length (or any integer value therebetween), such as between 50 and 5,000 nucleotides in length, for example between about 100 and 1,000 nucleotides in length (or any integer there between), or about 200 and 500 nucleotides in length. Techniques for determining nucleic acid and amino acid sequence identity are known in the art.

Many of the embodiments disclosed in this section are described in combination with, or in the context of, fokI nuclease, or a nuclease-retaining fragment thereof; however, it should be understood that other nuclease proteins, or functional fragments thereof, could also be used in an analogous manner to form the described compositions and carryout the described methods. For example, mung bean nuclease, pancreatic DNAase I, micrococcal nuclease; yeast HO endonuclease; and other may be used in this context. (See, e.g., Linn et al. (eds.) Nucleases, Cold Spring Harbor Laboratory Press, 1993 and Schierling et al., Nucleic Acids Res. 2012 March; 40(6): 2623-2638.)

Differentiation of Embryonic Stem Cells

An embryonic stem (ES) cell may also be caused to differentiate into a lineage-specific cell using methods and compositions described herein. Accordingly, provided herein are methods of using the described polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs for causing an ES cell to differentiate into a lineage-specific cell. In some embodiments the ES cell used to carry out the described methods may be "long term" ES cell that are capable of dividing in culture for at least 15 cell divisions, such as at least 15, 20, 25, 30, 35, 40, 45 or 50 cell divisions while retaining the properties of an ES cell.

One embodiment of the described method for causing an ES cell to differentiate into a lineage-specific cell is carried out by introducing into an ES cell a first polypeptide with a DNA-binding domain specific for a DNA sequence upstream of a genomic sequence of interest, a second polypeptide with a DNA-binding domain specific for a DNA sequence downstream from the genomic sequence of interest, and a single-stranded or double-stranded donor polynucleotide encoding one or more factors sufficient to differentiate an ES cell into a lineage-specific cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the ES cell into a lineage-specific cell.

One embodiment of the described method for causing an ES cell to differentiate into a lineage-specific cell is carried out by introducing into an ES cell a first polypeptide with a DNA-binding domain specific for a DNA sequence upstream of a genomic sequence of interest, a second polypeptide with a DNA-binding domain specific for a DNA sequence downstream from the genomic sequence of interest, and a single-stranded or double-stranded donor polynucleotide encoding one or more factors sufficient to differentiate an ES cell into a lineage-specific cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the ES cell into a lineage-specific cell.

One embodiment of the described method for causing an ES cell to differentiate into a lineage-specific cell is carried out by introducing into an ES cell a first polypeptide with a DNA-binding domain, having the sequence of SEQ ID NO: 7, specific for a DNA sequence upstream of a genomic sequence of interest, a second polypeptide with a DNA-binding domain, having the sequence of SEQ ID NO: 10, specific for a DNA sequence downstream from the genomic sequence of interest, and a single-stranded or double-stranded donor polynucleotide encoding one or more factors sufficient to differentiate an ES cell into a lineage-specific cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the ES cell into a lineage-specific cell.

One embodiment of the described method for causing an ES cell to differentiate into a lineage-specific cell is carried out by introducing into an ES cell a first polypeptide with a DNA-binding domain specific for a DNA sequence within the sequence of SEQ ID NO: 19 upstream of a genomic sequence of interest, a second polypeptide with a DNA-binding domain specific for a DNA sequence within a sequence complementary to the sequence of SEQ ID NO: 19 downstream from the genomic sequence of interest, and a single-stranded or double-stranded donor polynucleotide encoding one or more factors sufficient to differentiate an ES cell into a lineage-specific cell, comprising sense and/or antisense strand polynucleotide overhangs that are complementary to corresponding polynucleotide overhangs of genomic DNA cleaved by the introduced polypeptides at a genomic insertion site, wherein said complementary overhangs facilitate insertion of the donor polynucleotide to the cleaved genomic DNA. The integrated donor DNA can then be expressed by the cell and convert the ES cell into a lineage-specific cell.

Another such method involves introducing into an ES cell a first TALEN with a DNA-binding domain specific for a DNA sequence upstream of a genomic sequence of interest, a second TALEN with a DNA-binding domain specific for a DNA sequence downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One application for use with some of the compositions described herein is a method for causing an ES cell to differentiate into a lineage-specific cell by introducing into the ES cell a first TALEN with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

Another application for use with some of the compositions described herein is a method for causing an iPS cell to differentiate into a lineage-specific cell by introducing into the ES cell a first TALEN with a DNA-binding domain specific for a DNA sequence within human chromosome 13 that binds upstream of a genomic sequence of interest and a second TALEN with a DNA-binding domain specific for a DNA sequence within human chromosome 13 that binds downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

Another application for use with some of the compositions described herein is a method for causing an ES cell to differentiate into a lineage-specific cell by introducing into the ES cell a first TALEN with a DNA-binding domain specific for a DNA sequence within the CLYBL safe-harbor locus that binds upstream of a genomic sequence of interest and a second TALEN with a DNA-binding domain specific for a DNA sequence within the CLYBL safe-harbor locus that binds downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One embodiment of the described method for causing an ES cell to differentiate into a lineage-specific cell is by introducing into the ES cell a first TALEN with a DNA-binding domain specific for a DNA sequence within intron 2 of the CLYBL safe-harbor locus that binds upstream of a genomic sequence of interest and a second TALEN with a DNA-binding domain specific for a DNA sequence within intron 2 of the CLYBL safe-harbor locus that binds downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

Another application for use with some of the compositions described herein is a method for causing an ES cell to differentiate into a lineage-specific cell by introducing into the ES cell a first TALEN with a DNA-binding domain specific for a DNA sequence within the sequence of SEQ ID NO: 19 that binds upstream of a genomic sequence of interest and a second TALEN with a DNA-binding domain specific for a DNA sequence within the sequence of SEQ ID NO: 19 that binds downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

Another application for use with some of the compositions described herein is a method for causing an ES cell to differentiate into a lineage-specific cell by introducing into the ES cell a first TALEN with a DNA-binding domain specific for a DNA sequence having the sequence of SEQ ID NO: 1 that binds upstream of a genomic sequence of interest and a second TALEN with a DNA-binding domain specific for a DNA sequence having the sequence of SEQ ID NO: 3 that binds downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One embodiment of the method for causing an ES cell to differentiate into a lineage-specific cell includes introducing into the ES cell a first TALEN, having the sequence of SEQ ID NO: 7, with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method for causing an ES cell to differentiate into a lineage-specific cell includes introducing into the ES cell a first TALEN with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method for causing an ES cell to differentiate into a lineage-specific cell includes introducing into the ES cell a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method for causing an ES cell to differentiate into a lineage-specific cell includes introducing into the ES cell a first TALEN, having the sequence of SEQ ID NO: 8, with a DNA-binding domain specific for a DNA sequence upstream of a genomic sequence of interest and a second TALEN with a DNA-binding domain specific for a DNA sequence downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One embodiment of the method for causing an ES cell to differentiate into a lineage-specific cell includes introducing into the ES cell a first TALEN with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One embodiment of the method for causing an ES cell to differentiate into a lineage-specific cell includes introducing into the ES cell a first TALEN, having the sequence of SEQ ID NO: 8, with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

Another application for use with some of the compositions described herein is a method for causing an ES cell to differentiate into a lineage-specific cell by introducing into the ES cell a first TALEN with a DNA-binding domain specific for a DNA sequence within human chromosome 13 that binds to the sense strand of DNA upstream of a genomic sequence of interest and a second TALEN with a DNA-binding domain specific for a DNA sequence within human chromosome 13 that binds to the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

Another application for use with some of the compositions described herein is a method for causing an ES cell to differentiate into a lineage-specific cell by introducing into the ES cell a first TALEN with a DNA-binding domain specific for a DNA sequence within the CLYBL safe-harbor locus that binds to the sense strand of DNA upstream of a genomic sequence of interest and a second TALEN with a DNA-binding domain specific for a DNA sequence within the CLYBL safe-harbor locus that binds to the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One embodiment of the described method for causing an ES cell to differentiate into a lineage-specific cell is by introducing into the ES cell a first TALEN with a DNA-binding domain specific for a DNA sequence within intron 2 of the CLYBL safe-harbor locus that binds to the sense strand of DNA upstream of a genomic sequence of interest and a second TALEN with a DNA-binding domain specific for a DNA sequence within intron 2 of the CLYBL safe-harbor locus that binds to the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

Another application for use with some of the compositions described herein is a method for causing an ES cell to differentiate into a lineage-specific cell by introducing into the ES cell a first TALEN with a DNA-binding domain specific for a DNA sequence within the sequence of SEQ ID NO: 19 that binds to the sense strand of DNA upstream of a genomic sequence of interest and a second TALEN with a DNA-binding domain specific for a DNA sequence within the sequence of SEQ ID NO: 19 that binds to the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

Another application for use with some of the compositions described herein is a method for causing an ES cell to differentiate into a lineage-specific cell by introducing into the ES cell a first TALEN with a DNA-binding domain specific for a DNA sequence having the sequence of SEQ ID NO: 1 that binds to the sense strand of DNA upstream of a genomic sequence of interest and a second TALEN with a DNA-binding domain specific for a DNA sequence having the sequence of SEQ ID NO: 3 that binds to the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One embodiment of the method for causing an ES cell to differentiate into a lineage-specific cell includes introducing into the ES cell a first TALEN, having the sequence of SEQ ID NO: 7, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method for causing an ES cell to differentiate into a lineage-specific cell includes introducing into the ES cell a first TALEN with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method for causing an ES cell to differentiate into a lineage-specific cell includes introducing into the ES cell a first TALEN, having the sequence of SEQ ID NO: 7, with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method for causing an ES cell to differentiate into a lineage-specific cell includes introducing into the ES cell a first TALEN, having the sequence of SEQ ID NO: 8, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One embodiment of the method for causing an ES cell to differentiate into a lineage-specific cell includes introducing into the ES cell a first TALEN with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

One embodiment of the method for causing an ES cell to differentiate into a lineage-specific cell includes introducing into the ES cell a first TALEN, having the sequence of SEQ ID NO: 8, with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single-stranded or double-stranded donor polynucleotide encoding one or more factors sufficient to differentiate an ES cell into a lineage-specific cell, where the donor polynucleotide has sense and/or antisense strand polynucleotide overhangs that are complementary to corresponding polynucleotide overhangs of genomic DNA cleaved by the introduced TALENs at a genomic insertion site, wherein said complementary overhangs facilitate integration of the donor polynucleotide with the cleaved genomic DNA. The integrated donor DNA can then be expressed by the cell and convert the ES cell into a lineage-specific cell.

In accordance with the methods causing an ES cell to differentiate into a lineage-specific cell described in this section it should be understood that broadly applicable further aspects of these methods may be carried out as needed or desired. In one embodiment the described methods can be carried out to cause a donor polynucleotide encoding one or more factors sufficient to differentiate an ES cell into a lineage-specific cell to be inserted into both copies of the same chromosome of an ES cell. Factors sufficient to differentiate an ES cell into a lineage-specific cell applicable to the methods discussed include but are not limited to transforming growth factor beta (TGF-β), bone morphogenetic protein (BMP), NODAL, ACTIVIN, NOTCH, WNT, sonic hedgehog (SHH), JAK/STAT, and fibroblast growth factor (FGF) signaling pathway factors. These factors may be used alone or in combination with one another to cause an ES cell to differentiate into a lineage-specific cell due to their expression in the cell. In one embodiment the described methods can be carried out using nucleofection of a polynucleotide or vectors encoding the polypeptides or TALENs used with these methods. In a particular embodiment, nucleofection may be carried out using a Nucleofector™ apparatus. In some embodiments, the nucleofection provides a transfection efficiency of at least about 60%, at least about 65%, at least about 70%, at least about 75%, at least about 80%, at least about 85%, at least about 90%, or at least about 95%. In specific non-limiting example, the transfection efficiency is at least about 80%, at least about 85%, at least about 90%, at least about 95%, at least about 96%, about 97%, about 98% or about 99%. In some embodiments the step of introducing a first polypeptide or TALEN into an ES cell involves transfecting the cell with a polynucleotide encoding the polypeptide or TALEN. In some embodiments the step of introducing a second polypeptide or TALEN into an ES cell involves transfecting the cell with a polynucleotide encoding the polypeptide or TALEN. In some embodiments a single vector may be used to transfect an ES cell with polynucleotides that encode an upstream TALEN and the nucleic acid encoding the downstream TALEN. The methods described in the section are useful with a variety of an ES cell types, including, autologous cells of a subject, and particular an ES cell types generally known to exist in mammals.

In some embodiments of this section, the donor polynucleotide is a single-stranded or double-stranded donor polynucleotide with sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, such that the polynucleotide is introduced into the genome of the cell. In some embodiments, the overhangs are from about 15 base pairs to about 500 base pairs. In one embodiment the overhangs are at least 15 base pairs. In some embodiments, the overhangs are at least 15 nucleotides in length, such as 20, 30, 40, 50, 60, 70, 80, 90, 100, 200, 300, 400, 500, 600, 700, 800, 900, or 1,000 base pairs. In one embodiment, the overhangs are about 15 base pairs. In one embodiment, the overhangs are about 25 base pairs. In one embodiment, the overhangs are about 30 base pairs. In one embodiment, the overhangs are about 35 base pairs. In one embodiment, the overhangs are about 40 base pairs. In one embodiment, the overhangs are about 50 base pairs. In one embodiment, the overhangs are about 55 base pairs. In one embodiment, the overhangs are about 60 base pairs. In one embodiment, the overhangs are about 65 base pairs. In one embodiment, the overhangs are about 70 base pairs. In one embodiment, the overhangs are about 75 base pairs. In one embodiment, the overhangs are about 100 base pairs. In one embodiment, the overhangs are about 150 base pairs. In one embodiment, the overhangs are about 200 base pairs. In one embodiment, the overhangs are about 300 base pairs. In one embodiment, the overhangs are about 400 base pairs. In one embodiment, the overhangs are about 500 base pairs. The complementarity need not be 100% complementarity. For example, the complementary overhangs can be 95%, 96%, 97%, 98%, or 99% complementary to the overhangs of the cleaved DNA.

In some embodiments, the methods include inserting a donor polynucleotide into the genome of a cell. The donor sequence can be of any length, such as between 2 and 30,000 nucleotides in length (or any integer value therebetween), such as between 50 and 5,000 nucleotides in length, for example between about 100 and 1,000 nucleotides in length (or any integer there between), or about 200 and 500 nucleotides in length. Techniques for determining nucleic acid and amino acid sequence identity are known in the art.

Many of the embodiments disclosed in this section are described in combination with, or in the context of, fokI nuclease, or a nuclease-retaining fragment thereof; however, it should be understood that other nuclease proteins, or functional fragments thereof, could also be used in an analogous manner to form the described compositions and carryout the described methods. For example, mung bean nuclease, pancreatic DNAase I, micrococcal nuclease; yeast HO endonuclease; and other may be used in this context. (See, e.g., Linn et al. (eds.) Nucleases, Cold Spring Harbor Laboratory Press, 1993 and Schierling et al., Nucleic Acids Res. 2012 March; 40(6): 2623-2638.)

Screening Methods

It should be noted that cells produced by the methods disclosed herein can also be used to screen pharmaceutical agents to select for agents that affect specific human cell types.

In some embodiments, methods are provided for assessing the physiological effect of a polypeptide on a cell of interest. The methods include introducing into a polynucleotide into the cell using any of the methods disclosed above, and assessing a parameter of the neuronal stem cell, thereby determining the physiological effect of the polypeptide on the cell.

In some embodiments, methods are provided for assessing the physiological effect of a polypeptide on a cell of interest. The methods include excising a polynucleotide from the cell using any of the methods disclosed above, and assessing a parameter of the cell, thereby determining the physiological effect of the polypeptide on the cell of interest.

A method is provided herein for selecting an agent that affects the differentiation of human cells of interest. In one embodiment, the agent affects the differentiation of human cells into a differentiated cell fate.

The test compound can be any compound of interest, including chemical compounds, small molecules, polypeptides or other biological agents (for example antibodies or cytokines). In several examples, a panel of potential agents is screened, such as a panel of cytokines or growth factors is screened.

Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, Science 249:386-390, 1992; Markland et al., Gene 109:13-19, 1991), a peptide library (U.S. Pat. No. 5,264,563); a peptidomimetic library (Blondelle et al., Trends Anal Chem. 14:83-92, 1995); a nucleic acid library (O'Connell et al., Proc. Natl Acad. Sci., USA 93:5883-5887, 1996; Tuerk and Gold, Science 249:505-510, 1990; Gold et al., Ann. Rev. Biochem. 64:763-797, 1995); an oligosaccharide library (York et al., Carb. Res. 285:99-128, 1996; Liang et al., Science 274: 1520-1522, 1996; Ding et al., Adv. Expt. Med. Biol. 376: 261-269, 1995); a lipoprotein library (de Kruif et al., FEBS Lett. 3 99:23 2-23 6, 1996); a glycoprotein or glycolipid library (Karaoglu et al., J Cell Biol. 130.567-577, 1995); or a chemical library containing, for example, drugs or other pharmaceutical agents (Gordon et al., J Med. Chem. 37. 1385-1401, 1994; Ecker and Crooke, BioTechnology 13:351-360, 1995). Polynucleotides can be particularly useful as agents that can alter a function of ES cells because nucleic acid molecules having binding specificity for cellular targets, including cellular polypeptides, exist naturally, and because synthetic molecules having such specificity can be readily prepared and identified (see, for example, U.S. Pat. No. 5,750,342).

In one embodiment, for a high throughput format, cells can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the cells, particularly with respect to the function being examined. An advantage of using a high throughput format is that a number of test agents can be examined in parallel, and, if desired, control reactions also can be run under identical conditions as the test conditions. As such, the methods disclosed herein provide a means to screen one, a few, or a large number of test agents in order to identify an agent that can alter a function of cells, for example, an agent that induces the cells to differentiate into a desired cell type, or that prevents spontaneous differentiation, for example, by maintaining a high level of expression of regulatory molecules.

The cells are contacted with test compounds sufficient for the compound to interact with the cell. When the compound binds a discrete receptor, the cells are contacted for a sufficient time for the agent to bind its receptor. In some embodiments, the cells are incubated with the test compound for an amount of time sufficient to affect phosphorylation of a substrate. In some embodiments, cells are treated in vitro with test compounds at 37° C. in a 5% CO2 humidified atmosphere. Following treatment with test compounds, cells are washed with Ca2+ and Mg2+ free PBS and total protein is extracted as described (Haldar et al., Cell Death Diff. 1:109-115, 1994; Haldar et al., Nature 342:195-198, 1989; Haldar et al., Cancer Res. 54:2095-2097, 1994). In additional embodiments, serial dilutions of test compound are used.

NSCs

NSCs are of use in any of the methods disclosed herein. NSCs can be obtained from the central nervous system of a mammal, including, but not limited to, a human. NSCs have been isolated from several mammalian species, including mice, rats, pigs and humans, see PCT Publication No. WO 93/01275, PCT Publication No. WO 94/09119, PCT Publication No. WO 94/10292, PCT Publication No. WO 94/16718 and Cattaneo et al. (1996 Mol. Brain. Res. 42:161-66). These cells can be obtained from a variety of tissues including but not limited to, forebrain, hindbrain, whole brain and spinal cord. NSCs can be isolated and cultured using methods known in the art, for example using methods disclosed in U.S. Pat. No. 5,958,767 hereby incorporated by reference. The NSCs can be obtained from a cadaver or living subject. NSCs can be obtained from fetal tissue and adult brain biopsies. The NSCs can also be produced from other stem cells, such as induced pluripotent stem cells or embryonic stem cells. NSCs can be induced to proliferate and differentiate either by culturing the cells in suspension or on an adherent substrate (see U.S. Pat. No. 5,750,376 and U.S. Pat. No. 5,753,506).

NSCs can also be produced from other pluripotent and multipotent stem cells, such as induced pluripotent stem cells and embryonic stem cells. NSCs can be isolated from many different types of tissues, for example, from donor tissue by dissociation of individual cells from the connecting extracellular matrix of the tissue, or from commercial sources of NSCs. In one non-limiting example, tissue from brain is removed using sterile procedures, and the cells are dissociated using any method known in the art including treatment with enzymes such as trypsin, collagenase and the like, or by using physical methods of dissociation such as mincing or treatment with a blunt instrument. Dissociation of neural cells, and other multipotent stem cells, can be carried out in a sterile tissue culture medium. Dissociated cells are centrifuged at low speed, between 200 and 2000 rpm, usually between 400 and 800 rpm, the suspension medium is aspirated, and the cells are then resuspended in culture medium.

Following isolation, NSCs are incubated in a culturing medium in a culture apparatus for a period of time or until the cells reach confluency before passing the cells to another culture apparatus. The culturing apparatus can be of any culture apparatus commonly used for culturing cells in vitro. Preferably, the level of confluency of the cells is greater than 70% before passing the cells to another culture apparatus. More preferably, the level of confluency of the cells is greater than 90%. A period of time can be any time suitable for the culture of cells in vitro. The culturing medium may be replaced during the culture of the NSCs. NSCs are then harvested from the culture apparatus. The NSCs can be used immediately or they can be cryopreserved and stored for use at a later time. NSCs may be harvested by trypsinization, or any other procedure used to harvest cells from a culture apparatus.

In some embodiments, the NSCs are long term NSCs. Thus, in specific non-limiting examples, a neuronal stem cell of use in the methods disclosed herein divides in culture for at least 15 cell divisions. The NSC can maintain NSC markers such as nestin and sox1, and differentiate into neurons and glia under defined differentiation media and appropriate culture conditions in vitro. In specific non-limiting examples, the NSC divides in culture for least 15, 20, 25, 30, 35, 40, 45 or 50 cell divisions.

Standard culture media typically contains a variety of essential components required for cell viability, including inorganic salts, carbohydrates, hormones, essential amino acids, vitamins, and the like. In some embodiments, DMEM or F-12 is used as a culture medium. Both media are commercially available (DMEM; GIBCO, Grand Island, N.Y.; F-12, GIBCO, Grand Island, N.Y.). A premixed formulation of DMEM/F-12 is also available commercially. Additional additives can be used, such as glutamine, heparin, sodium bicarbonate and/or N2 supplement (Life Technologies, Gaithersburg, Md.). The pH of the culture medium is typically between 6-8, such as about 7, for example about 7.4. Cells are typically cultured at a temperature between 30-40° C., such as between 35-38° C., such as between 35-37° C., for example at 37° C.

Also disclosed are NSCs, and cells differentiated therefrom, that have been modified to express one or more of the polynucleotides disclosed herein. The NSCs can express any of the polypeptides disclosed above. In some embodiments a NSC is modified to include a polynucleotide including the sequence of SEQ ID NO: 2. In one embodiment a NSC is modified to include a polynucleotide including the sequence of SEQ ID NO: 4. In other embodiments a NSC is modified to include a polynucleotide including the sequence of SEQ ID NO: 5. In yet other embodiments a NSC is modified to include a polynucleotide including the sequence of SEQ ID NO: 6. In yet other embodiments, a NSC is modified to include a polynucleotide including the sequence of SEQ ID NO: 9. In additional embodiments a NSC is modified to include a polynucleotide including the sequence of SEQ ID NO: 12. Polypeptides encoded by one or more of SEQ ID NOs: 2, 4, 5, and/or 6 can be expressed by a NSC.

Methods for Engineering NSCs

Methods are provided for modifying the genome of a NSC. In some embodiments, these methods include, but are not limited to, introducing a polynucleotide of interest into a safe harbor locus in a genome of a NSC and excising a polynucleotide of interest from a NSC. In additional embodiments, the methods include excise a polynucleotide of interest from an NSC. In further embodiments, the method includes introducing a mutation into a polypeptide of interest.

The disclosed methods can target any safe harbor locus, such as AAVS1, CYBL and CCR5. In some embodiments, the safe harbor locus is CYBL. In additional embodiments, the methods allow for integration of a DNA into an intron of the CYBL safe harbor locus, such as intron 2 of the CLYBL safe harbor locus.

The NSC can be any NSC of interest, as disclosed above. In some embodiments the step of introducing a first polypeptide or TALEN into a cell involves transfecting the NSC with a polynucleotide encoding the polypeptide or TALEN. In some embodiments the step of introducing a second polypeptide or TALEN into a cell involves transfecting the cell with a polynucleotide encoding the polypeptide or TALEN. In some embodiments a single vector may be used to transfect a cell with polynucleotides that encode an upstream TALEN and the nucleic acid encoding the downstream TALEN.

Methods for introducing DNA into NSC include chemical and physical methods. Chemical methods include iposome-based gene transfer or lipofection, calcium phosphate-mediated gene transfer, DEAE-dextran transfection techniques, and polyethyleneimine (PEI)-mediated delivery. Physical methods include ballistic gene transfer (introduces particles coated with DNA into cells), microinjection, and nucleofection (Amaxa biosystem, 2004). In some embodiments, nucleofection can be used to introduce the polynucleotides disclosed herein into NSCs. In specific non-liming examples, the nucleofection involves the use of a nucleofectin D apparatus. In some embodiments, the nucleofection provides a transfection efficiency of at least about 60%, at least about 65%, at least about 70%, at least about 75%, at least about 80%, at least about 85%, at least about 90%, or at least about 95% of the transfected cells include the introduced DNA. In specific non-limiting examples, the nucleofection provides a transfection efficiency of at least about 80%, such as at least about 85%, at least about 90%, or at least about 95%, about 96%, 97%, about 98%, or about 99% of the transfected cells include the introduced DNA The method can include contacting the neuronal stem cell with the upstream TALEN, the downstream TALEN, and the polynucleotide of interest at a ratio of about 1:1:1. In additional embodiments, a ratio of about 1:2:1 or 2:1:1 or 1:1:2 is utilized. In other embodiments, 1:3:1 or 3:1:1 or 1:1:3 is utilized. In yet other embodiments a ratio of 1:4:1 or 4:1:1 or 1:4:1 I is utilized. In further embodiments a ratio of 1:5:1 or 5:1:1 or 1:1:5 is utilized.

In some embodiments, the donor polynucleotide encodes an agent for inducing the proliferation and/or differentiation of neuronal precursor cells, glial precursor cells, or glial cells. The agent can be a trophic agent or a growth factor. In specific non-limiting examples, the agent is nerve growth factor, insulin, fibroblast growth factor, glial derived neurotropic factor, a Notch ligand, Delta, brain derived neurotrophic factor, glial derived neurotrophic factor, bone morphogenic protein-2 or 4 (BMP-2/4), cilliarly neurotrophic factor (CNTF), heregulin-1 beta, platelet derived growth factor (PDGF)-1 or PDGF-B. In additional embodiments, the donor polynucleotide encodes a selectable marker and/or a detectable label. Suitable detectable labels include, but are not limited to, enzymes such as horse radish peroxidase and alkaline phosphatase, and fluorescent proteins, such as green fluorescent protein.

The donor polynucleotide can include a promoter operably linked to a heterologous nucleic acid, such as a nucleic acid encoding an agent of interest and/or a selectable marker and/or a detectable marker. The promoter can be constitutive or inducible. The promoter can be a lineage specific promoter, such as a promoter suitable for expression in neuronal cells and/or glial cells. In specific non-limiting examples, the promoter is a doublecourtin (DCX) or a GFAP promoter.

In some embodiments, the donor polynucleotide is a single or double-stranded donor polynucleotide with sense and/or antisense strand polynucleotide overhangs that are complementary to corresponding polynucleotide overhangs of cleaved the genomic DNA when cleaved at the genomic insertion site. In one non-limiting example, the donor polynucleotide is single stranded.

In another non-limiting example, the donor polynucleotide is double stranded with sense and/or antisense single stranded polynucleotide overhangs that are complementary to corresponding polynucleotide overhangs of the cleaved genomic DNA. The complementary overhangs facilitate homologous recombination of the donor polynucleotide with the cleaved genomic DNA, such that the polynucleotide is introduced into the genome of the cell. In some embodiments, the overhangs are at least 15 nucleotides in length, such as 20, 30, 40, 50, 60, 70, 80, 90, 100, 200, 300, 400, 500, 600, 700, 800, 900, or 1,000 base pairs. The complementarity need not be 100% complementarity. For example, the complementary overhangs can be 95%, 96%, 97%, 98%, or 99% complementary to the overhangs of the cleaved DNA. In additional embodiments, the complementary overhangs are at least 98% or at least 99% homologous to the overhangs of the cleaved DNA.

In some embodiments, the methods include inserting a donor polynucleotide into the genome of a NSC. The donor sequence can be of any length, such as between 2 and 30,000 nucleotides in length (or any integer value therebetween), such as between 50 and 5,00 nucleotides in length, for example between about 100 and 1,000 nucleotides in length (or any integer value therebetween), or about 200 and 500 nucleotides in length (or any integer value therebetween). Techniques for determining nucleic acid and amino acid sequence identity are known in the art.

In some embodiments, the methods include introducing into the neuronal stem cell (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, to allow introduction of the polynucleotide into the genome of the cell. These methods provide introduction of the donor polynucleotide into the genomic insertion site into the safe harbor locus in the genome of the neuronal stem cell. In some embodiments, the upstream TALEN binds to the sense strand of a genomic DNA locus flanking the insertion site and the downstream TALEN binds to the antisense strand of a genomic DNA locus flanking the insertion site.

In some embodiments the upstream TALEN comprises SEQ ID NO:8. In additional embodiments, the downstream TALEN comprises SEQ ID NO:11. In further embodiments, the DNA cleavage domain comprises a FokI nuclease domain, such as, but not limited to, SEQ ID NO: 13. In some embodiments, the genomic sense strand locus bound by the upstream TALEN comprises SEQ ID NO: 1. In yet other embodiments, the genomic antisense strand locus bound by the downstream TALEN comprises SEQ ID NO: 3. In further embodiments, the donor polynucleotide is inserted into both copies of the same chromosome, such as chromosome 13, for example into an intron on chromosome 13, such as intron 2 of chromosome 13 in the CYBL gene. In some embodiments, the polynucleotide is inserted into the two copies of the same chromosome.

One application is a method of modifying the genomic DNA of a NSC, by introducing into the NSC a first polypeptide with a DNA-binding domain, having the sequence of SEQ ID NO: 7 specific for a DNA sequence upstream of a genomic sequence of interest and a second polypeptide with a DNA-binding domain, having the sequence of SEQ ID NO: 10 specific for a DNA sequence downstream from the genomic sequence of interest, wherein the first and second polypeptides mediate cleavage of the genomic DNA and excises a genomic sequence of interest, thereby modifying the genomic DNA of the NSC. Another application is a method of modifying the genomic DNA of a NSC by introducing into the NSC a first polypeptide with a DNA-binding domain specific for a DNA sequence within the sequence of SEQ ID NO: 19 upstream of a genomic sequence of interest and a second polypeptide with a DNA-binding domain specific for a DNA sequence within the sequence of SEQ ID NO: 19 downstream from the genomic sequence of interest, wherein the first and second polypeptides mediate cleavage of the genomic DNA and excises a genomic sequence of interest, thereby modifying the genomic DNA of the NSC. Yet another application is a method of modifying the genomic DNA of a NSC by introducing into the NSC a first TALEN with a DNA-binding domain specific for a DNA sequence within human chromosome 13 that binds upstream of a genomic sequence of interest and a second TALEN with a DNA-binding domain specific for a DNA sequence within human chromosome 13 that binds downstream from the genomic sequence of interest, whereby the TALEN cleaves the genomic DNA and excises the genomic sequence of interest, thereby modifying the genomic DNA of the NSC.

Another application is a method of modifying the genomic DNA of a NSC that includes introducing into the cell a first TALEN with a DNA-binding domain specific for a DNA sequence within the CLYBL safe-harbor locus that binds upstream of a genomic sequence of interest and a second TALEN with a DNA-binding domain specific for a DNA sequence within the CLYBL safe-harbor locus that binds downstream from the genomic sequence of interest, whereby the TALEN cleaves the genomic DNA and excises the genomic sequence of interest, thereby modifying the genomic DNA of the NSC.

In some embodiments, the methods include introducing a single or double-stranded donor polynucleotide with sense and/or antisense strand polynucleotide overhangs that are complementary to corresponding polynucleotide overhangs of genomic DNA into the NSC. In other embodiments, the methods include introducing a single-stranded donor polynucleotide with sense and/or antisense strand polynucleotide overhangs (regions) that are complementary to corresponding polynucleotide overhangs of genomic DNA into the NSC, wherein the overhangs are at least 15 nucleotides in length, such as 20, 30, 40, 50, 60, 70, 80, 90, 100, 200, 300, 400, 500, 600, 700, 800, 900 or 1,000 base pairs in length. The complementarity need not be 100% complementarity. For example, the complementary overhangs can be 95%, 96%, 97%, 98%, or 99% complementary to the overhangs of the cleaved DNA. In additional embodiments, the complementary overhangs are at least 98% or at least 99% homologous to the overhangs of the cleaved DNA.

One embodiment of the disclosed method of modifying the genomic DNA of a NSC involves introducing into the cell a first TALEN with a DNA-binding domain specific for a DNA sequence within an intron, such as intron 2, of the CLYBL safe-harbor locus that binds upstream of a genomic sequence of interest and a second TALEN with a DNA-binding domain specific for a DNA sequence within the intron, such as intron 2, of the CLYBL safe-harbor locus that binds downstream from the genomic sequence of interest, whereby the TALEN cleaves the genomic DNA and excises the genomic sequence of interest, thereby modifying the genomic DNA of the NSC. Another embodiment is a method of modifying the genomic DNA of a NSC that includes introducing into the NSC a first TALEN with a DNA-binding domain specific for a DNA sequence within the sequence of SEQ ID NO: 19 that binds upstream of a genomic sequence of interest and a second TALEN with a DNA-binding domain specific for a DNA sequence within the sequence of SEQ ID NO: 19 that binds downstream from the genomic sequence of interest, whereby the TALEN cleaves the genomic DNA and excises the genomic sequence of interest, thereby modifying the genomic DNA of the NSC.

Another embodiment is a method of modifying the genomic DNA of a NSC that includes introducing into the NSC a first TALEN with a DNA-binding domain specific for a DNA sequence having the sequence of SEQ ID NO: 1 that binds upstream of a genomic sequence of interest and a second TALEN with a DNA-binding domain specific for a DNA sequence having the sequence of SEQ ID NO: 3 that binds downstream from the genomic sequence of interest, whereby the TALEN cleaves the genomic DNA and excises the genomic sequence of interest, thereby modifying the genomic DNA of the NSC.

One embodiment of the method of modifying genomic DNA includes introducing into the NSC a first TALEN, having the sequence of SEQ ID NO: 7 with a DNA-binding domain specific for a DNA sequence upstream of a genomic sequence of interest and a second TALEN with a DNA-binding domain specific for a DNA sequence downstream from the genomic sequence of interest, whereby the TALEN cleaves the genomic DNA and excises the genomic sequence of interest, thereby modifying the genomic DNA of the cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

Another embodiment of the method of modifying genomic DNA includes introducing into the NSC a first TALEN with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, whereby the TALEN cleaves the genomic DNA and excises the genomic sequence of interest, thereby modifying the genomic DNA of the NSC. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

A further embodiment of the method of modifying genomic DNA includes introducing into the NSC a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, whereby the TALEN cleaves the genomic DNA and excises the genomic sequence of interest, thereby modifying the genomic DNA of the cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

An additional embodiment of the method of modifying genomic DNA includes introducing into the NSC a first TALEN, having the sequence of SEQ ID NO: 8, with a DNA-binding domain specific for a DNA sequence upstream of a genomic sequence of interest and a second TALEN with a DNA-binding domain specific for a DNA sequence downstream from the genomic sequence of interest, whereby the TALEN cleaves the genomic DNA and excises the genomic sequence of interest, thereby modifying the genomic DNA of the NSC.

One embodiment of the method of modifying genomic DNA includes introducing into the NSC a first TALEN with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, whereby the TALEN cleaves the genomic DNA and excises the genomic sequence of interest, thereby modifying the genomic DNA of the NSC.

One embodiment of the method of modifying genomic DNA includes introducing into the NSC a first TALEN, having the sequence of SEQ ID NO: 8, with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, whereby the TALEN cleaves the genomic DNA and excises the genomic sequence of interest, thereby modifying the genomic DNA of the NSC.

Methods are provided for modifying the genomic DNA of a NSC that include introducing into the cell a first TALEN with a DNA-binding domain specific for a DNA sequence within human chromosome 13 that binds to the sense strand of DNA upstream of a genomic sequence of interest and a second TALEN with a DNA-binding domain specific for a DNA sequence within human chromosome 13 that binds to the antisense strand of DNA downstream from the genomic sequence of interest. The TALEN cleave the genomic DNA and excise the genomic sequence of interest, thereby modifying the genomic DNA of the NSC.

In some embodiments, methods are provided for modifying the genomic DNA of a NSC that include introducing into the cell a first TALEN with a DNA-binding domain specific for a DNA sequence within the CLYBL safe-harbor locus that binds to the sense strand of DNA upstream of a genomic sequence of interest and a second TALEN with a DNA-binding domain specific for a DNA sequence within the CLYBL safe-harbor locus that binds to the antisense strand of DNA downstream from the genomic sequence of interest. The TALEN cleave the genomic DNA and excise the genomic sequence of interest, thereby modifying the genomic DNA of the NSC.

In additional embodiments, methods are provided for modifying the genomic DNA of a NSC that include introducing into the cell a first TALEN with a DNA-binding domain specific for a DNA sequence within an intron of the CYBL safe-harbor locus (such as intron 2 of the CLYBL safe-harbor locus) that binds to the sense strand of DNA upstream of a genomic sequence of interest and a second TALEN with a DNA-binding domain specific for a DNA sequence within intron 2 of the CLYBL safe-harbor locus that binds to the antisense strand of DNA downstream from the genomic sequence of interest. The TALEN cleave the genomic DNA and excise the genomic sequence of interest, thereby modifying the genomic DNA of the NSC.

In further embodiments, methods are provided for modifying the genomic DNA of a NSC that include introducing into the NSC a first TALEN with a DNA-binding domain specific for a DNA sequence within the sequence of SEQ ID NO: 19 that binds to the sense strand of DNA upstream of a genomic sequence of interest and a second TALEN with a DNA-binding domain specific for a DNA sequence within the sequence of SEQ ID NO: 19 that binds to the antisense strand of DNA downstream from the genomic sequence of interest. The TALEN cleave the genomic DNA and excise the genomic sequence of interest, thereby modifying the genomic DNA of the NSC.

In further embodiments, method are provided for modifying the genomic DNA of a NSC that include introducing into the cell a first TALEN with a DNA-binding domain specific for a DNA sequence having the sequence of SEQ ID NO: 1 that binds to the sense strand of DNA upstream of a genomic sequence of interest and a second TALEN with a DNA-binding domain specific for a DNA sequence having the sequence of SEQ ID NO: 3 that binds to the antisense strand of DNA downstream from the genomic sequence of interest. The TALEN cleave the genomic DNA and excise the genomic sequence of interest, thereby modifying the genomic DNA of the NSC.

In some embodiments, methods are provided for modifying genomic DNA that include introducing into the NSC a first TALEN, having the sequence of SEQ ID NO: 7, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest. The TALEN cleave the genomic DNA and excise the genomic sequence of interest, thereby modifying the genomic DNA of the cell. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method of modifying genomic DNA includes introducing into the NSC a first TALEN with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest. The TALEN cleave the genomic DNA and excise the genomic sequence of interest, thereby modifying the genomic DNA of the NSC. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method of modifying genomic DNA includes introducing into the NSC a first TALEN, having the sequence of SEQ ID NO: 7, with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest. The TALEN cleave the genomic DNA and excise the genomic sequence of interest, thereby modifying the genomic DNA of the cell. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7, may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method of modifying genomic DNA includes introducing into the NSC a first TALEN, having the sequence of SEQ ID NO: 8, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest> The TALEN cleave the genomic DNA and excise the genomic sequence of interest, thereby modifying the genomic DNA of the cell.

Another embodiment of the method of modifying genomic DNA includes introducing into the NSC a first TALEN with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest. The TALEN cleave the genomic DNA and excise the genomic sequence of interest, thereby modifying the genomic DNA of the cell.

Yet another embodiment of the method of modifying genomic DNA includes introducing into the NSC a first TALEN, having the sequence of SEQ ID NO: 8, with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest. The TALEN cleaves the genomic DNA and excises the genomic sequence of interest, thereby modifying the genomic DNA of the NSC.

In accordance with the methods of modifying genomic DNA described in this section it should be understood that broadly applicable further aspects of these methods may be carried out as needed or desired. In one embodiment the described methods can be carried out to cause polynucleotide excision in both copies of the same chromosome.

Provided herein are methods of using the described polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs for inserting a polynucleotide into the genome of a NSC. In some embodiments, the method is carried out by introducing into a NSC a first polypeptide with a DNA-binding domain specific for a DNA sequence upstream of a genomic sequence of interest, a second polypeptide with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced polypeptides at a genomic insertion site. The complementary overhangs facilitate insertion of the donor polynucleotide to the cleaved genomic DNA, providing for the introduction of the donor polynucleotide into the genome of the NSC.

One embodiment of the disclosed method is carried out by introducing into a NSC a first polypeptide with a DNA-binding domain, including the sequence of SEQ ID NO: 7, specific for a DNA sequence upstream of a genomic sequence of interest, a second polypeptide with a DNA-binding domain, including the sequence of SEQ ID NO: 10, specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced polypeptides at a genomic insertion site. The complementary overhangs facilitate insertion of the donor polynucleotide to the cleaved genomic DNA, providing for the introduction of the donor polynucleotide into the genome of the NSC.

In some embodiments, the method includes introducing into a NSC a first polypeptide with a DNA-binding domain specific for a DNA sequence within the sequence of SEQ ID NO: 19 upstream of a genomic sequence of interest, a second polypeptide with a DNA-binding domain specific for a DNA sequence within the sequence of SEQ ID NO: 19 downstream from the genomic sequence of interest, and a single or double-stranded donor polynucleotide with sense and/or antisense strand polynucleotide overhangs that are complementary to corresponding polynucleotide overhangs of genomic DNA cleaved by the introduced polypeptides at a genomic insertion site. The complementary overhangs facilitate insertion of the donor polynucleotide to the cleaved genomic DNA, providing for the introduction of the donor polynucleotide into the genome of the NSC.

In some embodiments, the methods include introducing into a NSC a first TALEN with a DNA-binding domain specific for a DNA sequence upstream of a genomic sequence of interest, a second TALEN with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

Methods are also provided for using the polynucleotide-binding polypeptides, the recombinant DNA-binding polypeptides, zinc-finger or TALE domains, nuclease proteins or polypeptides, fusion proteins produced from the fusion of polynucleotide-binding polypeptides and nuclease proteins or polypeptides, and TALENs. One application is a method of inserting a polynucleotide into the genome of a NSC by introducing into the NSC a first TALEN with a DNA-binding domain specific for a DNA sequence upstream of a genomic sequence of interest and a second TALEN with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

Methods are also provided for inserting a polynucleotide into the genome of a NSC by introducing into the NSC a first TALEN with a DNA-binding domain specific for a DNA sequence within human chromosome 13 that binds upstream of a genomic sequence of interest and a second TALEN with a DNA-binding domain specific for a DNA sequence within human chromosome 13 that binds downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

In some embodiments, methods are provided for inserting a polynucleotide into the genome of a NSC by introducing into the NSC a first TALEN with a DNA-binding domain specific for a DNA sequence within the CLYBL safe-harbor locus that binds upstream of a genomic sequence of interest and a second TALEN with a DNA-binding domain specific for a DNA sequence within the CLYBL safe-harbor locus that binds downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

One embodiment of the described method of inserting a polynucleotide into the genome of a NSC involves introducing into the NSC a first TALEN with a DNA-binding domain specific for a DNA sequence within an intron (such as intron 2) of the CLYBL safe-harbor locus that binds upstream of a genomic sequence of interest and a second TALEN with a DNA-binding domain specific for a DNA sequence within intron 2 of the CLYBL safe-harbor locus that binds downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

Another application is a method of inserting a polynucleotide into the genome of a NSC by introducing into the NSC a first TALEN with a DNA-binding domain specific for a DNA sequence within the sequence of SEQ ID NO: 19 that binds upstream of a genomic sequence of interest and a second TALEN with a DNA-binding domain specific for a DNA sequence within the sequence of SEQ ID NO: 19 that binds downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

In some embodiments, methods are provided for inserting a polynucleotide into the genome of a NSC by introducing into the NSC a first TALEN with a DNA-binding domain specific for a DNA sequence having the sequence of SEQ ID NO: 1 that binds upstream of a genomic sequence of interest and a second TALEN with a DNA-binding domain specific for a DNA sequence having the sequence of SEQ ID NO: 3 that binds downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

One embodiment of the method of inserting a polynucleotide into the genome of a NSC includes introducing into the NSC a first TALEN, having the sequence of SEQ ID NO: 7, with a DNA-binding domain specific for a DNA sequence upstream of a genomic sequence of interest and a second TALEN with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method of inserting a polynucleotide into the genome of a NSC includes introducing into the NSC a first TALEN with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method of inserting a polynucleotide into the genome of a NSC includes introducing into the NSC a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method of inserting a polynucleotide into the genome of a NSC includes introducing into the NSC a first TALEN, having the sequence of SEQ ID NO: 8, with a DNA-binding domain specific for a DNA sequence upstream of a genomic sequence of interest and a second TALEN with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

One embodiment of the method of inserting a polynucleotide into the genome of a NSC includes introducing into the NSC a first TALEN with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

One embodiment of the method of inserting a polynucleotide into the genome of a NSC includes introducing into the NSC a first TALEN, having the sequence of SEQ ID NO: 8, with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

In some embodiments, a method of inserting a polynucleotide into the genome of a NSC includes introducing into the NSC a first TALEN with a DNA-binding domain specific for a DNA sequence within human chromosome 13 that binds to the sense strand of DNA upstream of a genomic sequence of interest and a second TALEN with a DNA-binding domain specific for a DNA sequence within human chromosome 13 that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

In additional embodiments, methods are provided for inserting a polynucleotide into the genome of a NSC that include introducing into the NSC a first TALEN with a DNA-binding domain specific for a DNA sequence within the CLYBL safe-harbor locus that binds to the sense strand of DNA upstream of a genomic sequence of interest and a second TALEN with a DNA-binding domain specific for a DNA sequence within the CLYBL safe-harbor locus that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

One embodiment of the described method of inserting a polynucleotide into the genome of a NSC involves introducing into the NSC a first TALEN with a DNA-binding domain specific for a DNA sequence within intron 2 of the CLYBL safe-harbor locus that binds to the sense strand of DNA upstream of a genomic sequence of interest and a second TALEN with a DNA-binding domain specific for a DNA sequence within intron 2 of the CLYBL safe-harbor locus that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

In additional embodiments, methods are provided for inserting a polynucleotide into the genome of a NSC that include introducing into the NSC a first TALEN with a DNA-binding domain specific for a DNA sequence within the sequence of SEQ ID NO: 19 that binds to the sense strand of DNA upstream of a genomic sequence of interest and a second TALEN with a DNA-binding domain specific for a DNA sequence within the sequence of SEQ ID NO: 19 that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

In further embodiments, methods are provided for inserting a polynucleotide into the genome of a NSC that include introducing into the NSC a first TALEN with a DNA-binding domain specific for a DNA sequence having the sequence of SEQ ID NO: 1 that binds to the sense strand of DNA upstream of a genomic sequence of interest and a second TALEN with a DNA-binding domain specific for a DNA sequence having the sequence of SEQ ID NO: 3 that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

One embodiment of the method of inserting a polynucleotide into the genome of a NSC includes introducing into the NSC a first TALEN, having the sequence of SEQ ID NO: 7, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13.

One embodiment of the method of inserting a polynucleotide into the genome of a NSC includes introducing into the NSC a first TALEN with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13.

One embodiment of the method of inserting a polynucleotide into the genome of a NSC includes introducing into the NSC a first TALEN, having the sequence of SEQ ID NO: 7, with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13.

One embodiment of the method of inserting a polynucleotide into the genome of a NSC includes introducing into the NSC a first TALEN, having the sequence of SEQ ID NO: 8, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

One embodiment of the method of inserting a polynucleotide into the genome of a NSC includes introducing into the NSC a first TALEN with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

One embodiment of the method of inserting a polynucleotide into the genome of a NSC includes introducing into the NSC a first TALEN, having the sequence of SEQ ID NO: 8, with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC.

In accordance with the methods of inserting a polynucleotide into the genome of a NSC described in this section it should be understood that broadly applicable further aspects of these methods may be carried out as needed or desired. In one embodiment the described methods can be carried out to cause polynucleotide excision in both copies of the same chromosome.

In some embodiments the step of introducing a first polypeptide or TALEN into a NSC involves transfecting the NSC with a polynucleotide encoding the polypeptide or TALEN. In some embodiments the step of introducing a second polypeptide or TALEN into a NSC involves transfecting the NSC with a polynucleotide encoding the polypeptide or TALEN. In some embodiments a single vector may be used to transfect a NSC with polynucleotides that encode an upstream TALEN and the nucleic acid encoding the downstream TALEN.

Differentiation of NSC

Methods are provided for inducing a NSCs to differentiate to a neuronal and/or glial cells. The NSCs can be differentiated into neuronal cells, including cholinergic neurons, GABAnergic neurons, glutaminergic neurons, serotonergic neurons and domainergic neurons. The NSCs can be differentiated into glial cells including astrocytes, neuroglia and oligodendrocytes.

In some embodiments, the method includes expressing an agent for inducing the proliferation and/or differentiation of neuronal or glial cells in the NSC. The agent can be a trophic agent or a growth factor. The agent or growth factor can be encoded by the polynucleotide of interest.

In specific non-limiting examples, the agent is nerve growth factor, nerve growth factor, insulin, fibroblast growth factor, glial derived neurotropic factor, a Notch ligand, Delta, brain derived neurotrophic factor, glial derived neurotrophic factor, bone morphogenic protein-2 or 4 (BMP-2/4), cilliarly neurotrophic factor (CNTF), heregulin-1 beta, platelet derived growth factor (PDGF)-1 or PDGF-B. In other embodiments, the donor polynucleotide also encodes a selectable marker and/or a detectable label. Suitable detectable labels include, but are not limited to, enzymes such as horse radish peroxidase and alkaline phosphatase, and fluorescent proteins, such as green fluorescent protein.

The donor polynucleotide can include a promoter operably linked to a heterologous nucleic acid, such as a nucleic acid encoding an agent of interest and/or a selectable marker and/or a detectable marker. The promoter can be constitutive or inducible. The promoter can be a lineage specific promoter, such as a promoter suitable for expression in neuronal cells and/or glial cells. In specific non-limiting examples, the promoter is an doublecourtin or a GFAP promoter.

Methods for introducing DNA into NSC include chemical and physical methods. Chemical methods include iposome-based gene transfer or lipofection, calcium phosphate-mediated gene transfer, DEAE-dextran transfection techniques, and polyethyleneimine (PEI)-mediated delivery. Physical methods include ballistic gene transfer (introduces particles coated with DNA into cells), microinjection, and nucleofection (Amaxa biosystem, 2004). In some embodiments, nucleofection can be used to introduce the polynucleotides disclosed herein into NSCs. In a specific non-liming example, the nucleofection involves the use of a nucleofectin D apparatus. In some embodiments, the nucleofection provides a transfection efficiency of at least about 60%, at least about 65%, at least about 70%, at least about 75%, at least about 80%, at least about 85%, at least about 90%, or at least about 95%. In specific non-limiting example, the transfection efficiency is at least about 80%, at least about 85%, at least about 90%, at least about 95%, at least about 96%, about 97%, about 98% or about 99%.

The method can include contacting the neuronal stem cell with the upstream TALEN, the downstream TALEN, and the polynucleotide of interest at a ratio of about 1:1:1. In additional embodiments, a ratio of about 1:2:1 or 2:1:1 or 1:1:2 is utilized. In other embodiments, 1:3:1 or 3:1:1 or 1:1:3 is utilized. In yet other embodiments a ratio of 1:4:1 or 4:1:1 or 1:4:1 I is utilized. In further embodiments a ratio of 1:5:1 or 5:1:1 or 1:1:5 is utilized.

Undifferentiated neural stem cells differentiate into neuroblasts and glioblasts which give rise to neurons and glial cells. Methods of culturing neural stem cells and neuronal/glial progenitor cells are well known to those of skill in the art (Hazel and Muller, 1997; U.S. Pat. No. 5,750,376, which are both incorporated herein by reference). Methods for isolating and culturing neuronal precursor cells are disclosed, for example, in U.S. Pat. No. 6,610,540, which is incorporated herein by reference. The NSC, or cells that are produced therefrom, can be cultured in a growth medium or a differentiation medium.

In some embodiments, these methods include introducing into the NSC (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the NSC, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the NSC, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, thereby introducing the donor polynucleotide into the genome of the NSC. In some embodiments, the upstream TALEN binds to the sense strand of a genomic DNA locus flanking the insertion site and the downstream TALEN binds to the antisense strand of a genomic DNA locus flanking the insertion site. In additional embodiments, the donor polynucleotide encodes one or more agents sufficient to differentiate the NSC into the neuronal or glial cell.

In some embodiments, the methods include introducing into the NSC (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the NSC, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the NSC, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, to allow introduction of the polynucleotide into the genome of the NSC. These methods provide introduction of the donor polynucleotide into the genomic insertion site into the safe harbor locus in the genome of the NSC. In some embodiments, the upstream TALEN binds to the sense strand of a genomic DNA locus flanking the insertion site and the downstream TALEN binds to the antisense strand of a genomic DNA locus flanking the insertion site. In some embodiments, the donor polynucleotide encodes one or more agents sufficient to differentiate the NSC into the neuronal or glial cell.

In some embodiments the upstream TALEN comprises SEQ ID NO:8. In additional embodiments, the downstream TALEN comprises SEQ ID NO:11. In further embodiments, the DNA cleavage domain comprises a FokI nuclease domain, such as, but not limited to, SEQ ID NO: 13. In some embodiments, the genomic sense strand locus bound by the upstream TALEN comprises SEQ ID NO: 1. In yet other embodiments, the genomic antisense strand locus bound by the downstream TALEN comprises SEQ ID NO: 3. In further embodiments, the donor polynucleotide is inserted into both copies of the same chromosome, such as chromosome 13, for example into intron 2 of chromosome 13. In some embodiments, the polynucleotide is inserted into the two copies of the same chromosome. The donor polynucleotide encodes one or more factors sufficient to differentiate the NSC into the neuronal or glial cell. In some embodiments, the donor polynucleotide encodes one or more factor sufficient to differentiate the NSC into the neuronal or glial cell.

A further embodiment of the method of differentiating a NSC includes introducing into the NSC a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, whereby the TALEN cleaves the genomic DNA and excises the genomic sequence of interest, thereby modifying the genomic DNA of the NSC. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13. In some embodiments, the donor polynucleotide encodes one or more agents sufficient to differentiate the NSC into the neuronal or glial cell.

In some embodiments, methods for differentiating an NSC include introducing into the NSC a first TALEN with a DNA-binding domain specific for a DNA sequence having the sequence of SEQ ID NO: 1 that binds upstream of a genomic sequence of interest and a second TALEN with a DNA-binding domain specific for a DNA sequence having the sequence of SEQ ID NO: 3 that binds downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

One embodiment of the method of differentiating a NSC includes introducing into the NSC a first TALEN, having the sequence of SEQ ID NO: 7, with a DNA-binding domain specific for a DNA sequence upstream of a genomic sequence of interest and a second TALEN with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN, having the sequence of SEQ ID NO: 7, with a DNA-binding domain specific for a DNA sequence upstream of a genomic sequence of interest and a second TALEN, having the sequence of SEQ ID NO: 10, with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13. The donor polynucleotide encodes one or more agents, wherein expression of the one or more agents is sufficient to differentiate the NSC into the neuronal or glial cell.

One embodiment of the method of the method for differentiating a NSC includes introducing into the NSC a first TALEN, having the sequence of SEQ ID NO: 8, with a DNA-binding domain specific for a DNA sequence upstream of a genomic sequence of interest and a second TALEN with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

One embodiment of the method of the method for differentiating a NSC includes introducing into the NSC a first TALEN with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN, having the sequence of SEQ ID NO: 8, with a DNA-binding domain specific for a DNA sequence upstream of a genomic sequence of interest and a second TALEN, having the sequence of SEQ ID NO: 11, with a DNA-binding domain specific for a DNA sequence downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

In some embodiments, methods are provided for differentiating a NSC that include introducing into the NSC a first TALEN with a DNA-binding domain specific for a DNA sequence within human chromosome 13 that binds to the sense strand of DNA upstream of a genomic sequence of interest and a second TALEN with a DNA-binding domain specific for a DNA sequence within human chromosome 13 that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

In some embodiments, methods are provided for differentiating a NSC that include introducing into the NSC a first TALEN with a DNA-binding domain specific for a DNA sequence within the CLYBL safe-harbor locus that binds to the sense strand of DNA upstream of a genomic sequence of interest and a second TALEN with a DNA-binding domain specific for a DNA sequence within the CLYBL safe-harbor locus that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

One embodiment for differentiating an NSC includes introducing into the NSC a first TALEN with a DNA-binding domain specific for a DNA sequence within intron 2 of the CLYBL safe-harbor locus that binds to the sense strand of DNA upstream of a genomic sequence of interest and a second TALEN with a DNA-binding domain specific for a DNA sequence within intron 2 of the CLYBL safe-harbor locus that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

Another application is a method for differentiating a NSC by introducing into the NSC a first TALEN with a DNA-binding domain specific for a DNA sequence within the sequence of SEQ ID NO: 19 that binds to the sense strand of DNA upstream of a genomic sequence of interest and a second TALEN with a DNA-binding domain specific for a DNA sequence within the sequence of SEQ ID NO: 19 that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

Another application is a method for differentiating a NSC that includes introducing into the NSC a first TALEN with a DNA-binding domain specific for a DNA sequence having the sequence of SEQ ID NO: 1 that binds to the sense strand of DNA upstream of a genomic sequence of interest and a second TALEN with a DNA-binding domain specific for a DNA sequence having the sequence of SEQ ID NO: 3 that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN, having the sequence of SEQ ID NO: 7, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 7 may also include a nuclease derived from fokI. In a specific embodiment, a TALEN incorporating the polypeptide of SEQ ID NO: 7 may also include a nuclease derived from fokI having the sequence of SEQ ID NO: 13. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 10 may also include a nuclease derived from fokI. In a specific embodiment, a TALEN incorporating the polypeptide of SEQ ID NO: 10 may also include a nuclease derived from fokI having the sequence of SEQ ID NO: 13. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN, having the sequence of SEQ ID NO: 7, with a DNA-binding domain specific for a DNA sequence on the sense strand of DNA upstream of a genomic sequence of interest and a second TALEN, having the sequence of SEQ ID NO: 10, with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. In a further embodiment, a TALEN incorporating the polypeptide of SEQ ID NO: 7 may also include a nuclease derived from fokI and a TALEN incorporating the polypeptide of SEQ ID NO: 10 may also include a nuclease derived from fokI. In a specific embodiment, a TALEN incorporating the polypeptide of SEQ ID NO: 7 may also include a nuclease derived from fokI having the sequence of SEQ ID NO: 13 and a TALEN incorporating the polypeptide of SEQ ID NO: 10 may also include a nuclease derived from fokI having the sequence of SEQ ID NO: 13. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN, having the sequence of SEQ ID NO: 8, with a DNA-binding domain specific for a DNA sequence on the sense strand of DNA upstream of a genomic sequence of interest and a second TALEN with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

One embodiment of the method for differentiating a NSC includes introducing into the NSC a first TALEN, having the sequence of SEQ ID NO: 8, with a DNA-binding domain specific for a DNA sequence on the sense strand of DNA upstream of a genomic sequence of interest and a second TALEN, having the sequence of SEQ ID NO: 11, with a DNA-binding domain specific for a DNA sequence on the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide into the genome of the NSC. The donor polynucleotide encodes one or more agents, wherein expression of the one or more agents is sufficient to differentiate the NSC into the neuronal or glial cell.

In accordance with the methods of inserting a polynucleotide into the genome of a NSC described in this section it should be understood that broadly applicable further aspects of these methods may be carried out as needed or desired. In one embodiment the described methods can be carried out to cause polynucleotide excision in both copies of the same chromosome. In one embodiment the described methods can be carried out using nuclofection of a polynucleotide or vectors encoding the polypeptides or TALENs used with these methods. In some embodiments the step of introducing a first polypeptide or TALEN into a NSC involves transfecting the NSC with a polynucleotide encoding the polypeptide or TALEN. In some embodiments the step of introducing a second polypeptide or TALEN into a NSC involves transfecting the NSC with a polynucleotide encoding the polypeptide or TALEN. In some embodiments a single vector may be used to transfect a NSC with polynucleotides that encode an upstream TALEN and the nucleic acid encoding the downstream TALEN.

In accordance with the methods of inserting a polynucleotide into the genome of a NSC described in this section it should be understood that broadly applicable further aspects of these methods may be carried out as needed or desired. In one embodiment the described methods can be carried out to cause polynucleotide excision in both copies of the same chromosome.

Methods of Treatment

The methods disclosed herein modify the genome of a NSC and/or differentiate the NSC. The NSCs, and cells differentiated from these NSCs, can be used for treating a subject.

In some embodiments, the disclosed methods can be employed to produce NSC and/or differentiated neuronal cells produced from these NSC in order to deliver the cells, or molecules expressed by these cells, to the brain for diagnosis, treatment or prevention of disorders or diseases of the CNS, brain, and/or spinal cord. These disorders can be neurologic or psychiatric disorders. These disorders or diseases include brain diseases such as Alzheimer's disease, Parkinson's disease, Lewy body dementia, multiple sclerosis, ALS, epilepsy, cerebellar ataxia, progressive supranuclear palsy, and amyotrophic lateral sclerosis. The methods disclosed herein also can be employed in subjects suffering from or at risk for nerve damage from cerebrovascular disorders such as stroke in the brain or spinal cord, from CNS infections including meningitis and HIV, from tumors of the brain and spinal cord, or from a prior disease. The disclosed methods are also of use to treat stroke, traumatic brain injury, spinal cord injury, and a partial or complete transection of a peripheral nerve.

In some embodiments, the method can also be employed to deliver agents to counter CNS disorders resulting from ordinary aging (e.g., insomnia or loss of the general chemical sense), or an injury, such as a traumatic brain injury, or spinal cord injury. The present methods can be employed to deliver agents and/or cells to the brain and/or the peripheral nervous system of a subject for diagnosis, treatment or prevention.

In further embodiments, the method can be employed to deliver to a subject an effective amount of NSC or cells differentiated therefrom, wherein the cells are engineered to express a nucleic acid of interest and/or to have a portion of the genomic DNA excised. For example, if a neuronal disorder, such as a neurodegenerative disorder, is caused by dominant negative protein, the genomic DNA encoding this protein can be excised. In specific non-limiting examples, the cells are autologous to the subject.

The subject can be any subject of interest. The method is useful in the treatment of animals (including mammals such as humans) having a neurological condition associated with neuronal dysfunction caused by disease or injury to neurons in either the central or peripheral nervous systems. The methods can also be used in association with procedures such as a surgical nerve graft, or other implantation of neurological tissue, to promote healing of the graft or implant, and promote incorporation of cells into the graft or implant into adjacent tissue. In one embodiment, a transection of a peripheral nerve or a spinal cord injury can be treated. In other embodiments, the subject has a neurodegenerative disorder. In additional embodiments, the subject has Parkinson's disease, amyotrophic lateral sclerosis (ALS), multiple sclerosis, Huntington's disease, Alzheimer's disease, Pantothenate kinase associated neurodegeneration (PKAN), multiple system atrophy, diabetic retinopathy, multi-infarct dementia, macular degeneration, stroke, a spinal cord injury, and/or a traumatic brain injury.

The neuronal stem cells can be human, and can be autologous or heterologous. NSCs can be obtained from several sources; allogeneic sources include fetal tissue, cadaveric samples, while autologous sources can come from brain biopsies or differentiated induced pluripotent cells (iPSCs). The neuronal stem cells can be elected to be matched to the subject of interest, for example at the major and/or minor histocompatibility loci.

The cells produced by the methods disclosed herein can also be used to replace or augment peripheral cells and neurons that are injured by neurotoxins and other insults. This method of treatment is beneficial in cases of a neurological disorder, such as, but not limited to a disease where an environmental factor is suspected of being one of the causative agents of the disease. Application of cells can also be used to affect the loss of smell or of the general chemical sense which may be associated with neurodegenerative diseases and ordinary aging.

The cells can also be used in the treatment of a neurodegenerative disorder such as, but not limited to, Parkinson's disease. The principal therapeutic target in the brain for Parkinson's disease is the substantia nigra which extends forward over the dorsal surface of the basis peduncle from the rostral border of the pons toward the subthalamic nucleus. Other therapeutic target areas are the locus ceruleus which is located in the rostral pons region and the ventral tegmental area which is located dorsomedial to the substantia nigra.

After the neuronal stem cells are formed and/or differentiated according to the methods disclosed above, the cells are suspended in a physiologically compatible carrier. The carrier can be any carrier compatible with the other ingredients of the formulation and not deleterious to the recipient thereof. Those of skill in the art are familiar with physiologically compatible carriers. Examples of suitable carriers include cell culture medium (e.g., Eagle's minimal essential media), phosphate buffered saline, and Hank's balanced salt solution+/−glucose (HBSS). In one embodiment, supporting cells, such as glia or astrocytes, can be added. These cells can be from the same species as the neuronal cells, or from a different species. Thus, in one embodiment, neuronal stem cells are differentiated to neuronal cells, and administered to the subject in conjunction with human glia or astrocytes. In another embodiment, the human neuronal cells and/or neuronal stem cells are administered with astrocytes or glial cells to the subject. In some embodiments, the astrocytes or glial cells can be non-human.

The volume of cell suspension administered to a subject will vary depending on the site of implantation, treatment goal and amount of cells in solution. Typically the amount of cells administered to a subject will be a therapeutically effective amount. For example, where the treatment is for Parkinson's disease, transplantation of a therapeutically effective amount of cells will typically produce a reduction in the amount and/or severity of the symptoms associated with that disorder, e.g., rigidity, akinesia and gait disorder.

For the treatment of a neurodegenerative disorder, such as a Parkinson's patient, at least about 100,000 surviving cells, for example, dopaminergic cells, per grafted site provide a substantial beneficial effect from the transplantation. As cell survival is low in brain tissue transplantation in general (5-10%) at least 1 million cells are administered, such as from about 1 million to about 4 million cells are transplanted. Thus, neuronal cells can be differentiated from neuronal stem cells, see for example, PCT Publication No. WO2005/017131 for methods of producing dopaminergic neurons from stem cells. Alternatively, neuronal stem cells can be transplanted and differentiated in vivo.

In one embodiment, the cells are administered to the subject's brain. The cells can be implanted within the parenchyma of the brain, in the space containing cerebrospinal fluids, such as the sub-arachnoid space or ventricles, or extaneurally. Thus, in one example, the cells are transplanted to regions of the subject which are not within the central nervous system or peripheral nervous system, such as the celiac ganglion or sciatic nerve. In another embodiment, the cells are transplanted into the central nervous system, which includes all structures within the dura mater.

Typically, the cells are administered by injection into the brain of the subject. Injections can generally be made with a sterilized syringe having an 18-21 gauge needle. Although the exact size needle will depend on the species being treated, the needle should not be bigger than 1 mm diameter in any species. Those of skill in the art are familiar with techniques for administering cells to the brain of a subject.

In a further embodiment, NSCs are provided to the site of injury, such as a stroke, traumatic injury, peripheral nerve injury or a spinal cord injury. The cells can be provided in a biocompatible, bioresorbable carrier capable of maintaining the cells at the site, where necessary, means for directing axonal growth from the proximal to the distal ends of a severed neuron. Using the methods disclosed herein, the NSCs, or cell differentiated from these NSCs, can be engineered to express a factor or interest, such as a growth factor.

Means for directing axonal growth can be required where nerve regeneration is to be induced over an extended distance, such as greater than 10 mm. Many carriers capable of providing these functions are envisioned. For example, useful carriers include substantially insoluble materials or viscous solutions prepared as disclosed herein comprising laminin, hyaluronic acid or collagen, or other suitable synthetic, biocompatible polymeric materials such as polylactic, polyglycolic, or polybutyric acids and/or copolymers thereof. In one example, the carrier includes an extracellular matrix composition.

A nerve guidance channel can also be used. The channel acts both as a protective covering and a physical means for guiding growth of a neurite. Useful channels include a biocompatible membrane, which may be tubular in structure, having a dimension sufficient to span the gap in the nerve to be repaired, and having openings adapted to receive severed nerve ends. The membrane can be made of any biocompatible, nonirritating material, such as silicone or a biocompatible polymer, such as polyethylene or polyethylene vinyl acetate. The casing also may be composed of biocompatible, bioresorbable polymers, including, for example, collagen, hyaluronic acid, polylactic, polybutyric, and polyglycolic acids. In one embodiment, the outer surface of the channel is substantially impermeable.

Screening Methods

It should be noted that cells produced by the methods disclosed herein can also be used in to screen pharmaceutical agents to select for agents that affect specific human cell types, such as agents that affect neuronal cells.

In some embodiments, methods are provided for assessing the physiological effect of a polypeptide on a NSC. The methods include introducing into a polynucleotide into the NSC using any of the methods disclosed above, and assessing a parameter of the neuronal stem cell, thereby determining the physiological effect of the polypeptide on the NSC.

In some embodiments, methods are provided for assessing the physiological effect of a polypeptide on a NSC. The methods include excising a polynucleotide from the NSC using any of the methods disclosed above, and assessing a parameter of the NSC, thereby determining the physiological effect of the polypeptide on the NSC.

A method is provided herein for selecting an agent that affects the differentiation of human NSC. In one embodiment, the agent affects the differentiation of human NSC cells into a differentiated cell fate. In one embodiment, the agent affects the differentiation of NSC cells into neurons. The neurons can be dopaminergic neurons, but can also be adrenergic, serotinergic, or motor neurons. In another embodiment, the agent affects differentiation into glial cells.

The test compound can be any compound of interest, including chemical compounds, small molecules, polypeptides or other biological agents (for example antibodies or cytokines). In several examples, a panel of potential agents is screened, such as a panel of cytokines or growth factors is screened.

Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13-19, 1991), a peptide library (U.S. Pat. No. 5,264,563); a peptidomimetic library (Blondelle et al., *Trends Anal Chem.* 14:83-92, 1995); a nucleic acid library (O'Connell et al., *Proc. Natl Acad. Sci., USA* 93:5883-5887, 1996; Tuerk and Gold, *Science* 249:505-510, 1990; Gold et al., *Ann. Rev. Biochem.* 64:763-797, 1995); an oligosaccharide library (York et al., *Carb. Res.* 285:99-128, 1996; Liang et al., *Science* 274: 1520-1522, 1996; Ding et al., *Adv. Expt. Med. Biol.* 376: 261-269, 1995); a lipoprotein library (de Kruif et al., *FEBS Lett.* 3 99:23 2-23 6, 1996); a glycoprotein or glycolipid library (Karaoglu et al., *J Cell Biol.* 130.567-577, 1995); or a chemical library containing, for example, drugs or other pharmaceutical agents (Gordon et al., *J Med. Chem.* 37. 1385-1401, 1994; Ecker and Crooke, *BioTechnology* 13:351-360, 1995). Polynucleotides can be particularly useful as agents that can alter a function of ES cells because nucleic acid molecules having binding specificity for cellular targets, including cellular polypeptides, exist naturally, and because synthetic molecules having such specificity can be readily prepared and identified (see, for example, U.S. Pat. No. 5,750,342).

In one embodiment, for a high throughput format, NSCs can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the NSCs, particularly with respect to the function being examined. An advantage of using a high throughput format is that a number of test agents can be examined in parallel, and, if desired, control reactions also can be run under identical conditions as the test conditions. As such, the methods disclosed herein provide a means to screen one, a few, or a large number of test agents in order to identify an agent that can alter a function of NSCs, for example, an agent that induces the NSCs to differentiate into a desired cell type, or that prevents spontaneous differentiation, for example, by maintaining a high level of expression of regulatory molecules.

The cells are contacted with test compounds sufficient for the compound to interact with the cell. When the compound binds a discrete receptor, the cells are contacted for a sufficient time for the agent to bind its receptor. In some embodiments, the cells are incubated with the test compound for an amount of time sufficient to affect phosphorylation of a substrate. In some embodiments, cells are treated in vitro with test compounds at 37° C. in a 5% CO2 humidified atmosphere. Following treatment with test compounds, cells are washed with $Ca^{2+}$ and $Mg^{2+}$ free PBS and total protein is extracted as described (Haldar et al., *Cell Death Diff* 1:109-115, 1994; Haldar et al., *Nature* 342:195-198, 1989; Haldar et al., *Cancer Res.* 54:2095-2097, 1994). In additional embodiments, serial dilutions of test compound are used.

EXEMPLARY EMBODIMENTS

Clause 1: A recombinant DNA-binding polypeptide that specifically binds to the polynucleotide sequence of SEQ ID NO: 1.

Clause 2: The recombinant DNA-binding polypeptide of clause 1, wherein the DNA binding portion of said protein is a zinc-finger domain or a transcription activator-like effector (TALE) domain.

Clause 3: The recombinant DNA-binding polypeptide of clause 1, wherein said zinc-finger domain or a transcription activator-like effector (TALE) domain further comprises a polypeptide having nuclease activity.

Clause 4: The recombinant DNA-binding polypeptide of any one of clauses 1-3 comprising the amino acid sequence of SEQ ID NO: 7.

Clause 5: The recombinant DNA-binding polypeptide of any one of clauses 1-4, wherein said polypeptide is a transcription activator-like effector nuclease (TALEN) comprising the sequence of SEQ ID NO: 7.

Clause 6: The recombinant DNA-binding polypeptide of any one of clauses 1, 4, or 5, wherein said polypeptide is a transcription activator-like effector nuclease (TALEN) comprising the sequence of SEQ ID NO: 8.

Clause 7: The recombinant DNA-binding polypeptide of any one of the previous clauses, wherein said DNA-binding polypeptide interacts with the sequence of SEQ ID NO: 1 only when present on the sense strand of genomic DNA.

Clause 8: A recombinant polynucleotide comprising a coding region encoding the DNA-binding polypeptide of any one of clauses 4-6.

Clause 9: The recombinant polynucleotide of clause 8, wherein said coding region comprises the sequence of SEQ ID NO: 5.

Clause 10: The recombinant polynucleotide of clause 8 or 9, wherein said coding region comprises the sequence of SEQ ID NO: 2.

Clause 11: A vector comprising the recombinant polynucleotide of any one of clauses 8-10.

Clause 12: The vector of clause 11, wherein said vector comprises the polynucleotide sequence of SEQ ID NO: 9.

Clause 13: A cell comprising the vector, or a product of the vector, of clause 11 or 12.

Clause 14: The cell of clause 13, wherein said cell is a somatic cell, a stem cell, or an induced pluripotent stem cell.

Clause 15: A kit comprising the recombinant polynucleotide of any one of clauses 8, 9, or 10 and at least one of the following items: a transfection reagent, a nucleofection reagent, a selection agent, or instructions for use of said kit.

Clause 16: A recombinant DNA-binding polypeptide that specifically binds to the polynucleotide sequence of SEQ ID NO: 3.

Clause 17: The recombinant DNA-binding polypeptide of clause 3, wherein the DNA binding portion of said polypeptide is a zinc-finger domain or a transcription activator-like effector (TALE) domain.

Clause 18: The recombinant DNA-binding polypeptide of clause 3, wherein said zinc-finger domain or a transcription activator-like effector (TALE) domain further comprises a polypeptide having nuclease activity.

Clause 19: The recombinant DNA-binding polypeptide of any one of clauses 16-18 comprising the amino acid sequence of SEQ ID NO: 10.

Clause 20: The recombinant DNA-binding polypeptide of any one of clauses 16-19, wherein said protein is a transcription activator-like effector nuclease (TALEN) comprising the sequence of SEQ ID NO: 10.

Clause 21: The recombinant DNA-binding polypeptide of any one of clauses 16, 19, or 20, wherein said polypeptide is a transcription activator-like effector nuclease (TALEN) comprising the sequence of SEQ ID NO: 11.

Clause 22: The recombinant DNA-binding polypeptide of any one of clauses 16-21, wherein said DNA-binding polypeptide interacts with the sequence of SEQ ID NO: 3 only when present on the antisense strand of genomic DNA.

Clause 23: A recombinant polynucleotide comprising a coding region encoding the DNA-binding polypeptide of any one of clauses 19-21.

Clause 24: The recombinant polynucleotide of clause 23, wherein said coding region comprises the sequence of SEQ ID NO: 6.

Clause 25: The recombinant polynucleotide of clause 23 or 24, wherein said coding region comprises the sequence of SEQ ID NO: 4.

Clause 26: A vector comprising the recombinant polynucleotide of any one of clauses 23-25.

Clause 27: The vector of clause 26, wherein said vector comprises the polynucleotide sequence of SEQ ID NO: 12.

Clause 28: A cell comprising the vector, or a product of the vector, of clause 26 or 27.

Clause 29: The cell of clause 28, wherein said cell is a somatic cell, a stem cell, or an induced pluripotent stem cell.

Clause 30: A kit comprising the recombinant polynucleotide of any one of clauses 23-25 and at least one of the following items: a transfection reagent, a nucleofection reagent, a selection agent, or instructions for use of said kit.

Clause 31: A method of inserting a polynucleotide into the genome of a cell, comprising introducing into the cell (a) an upstream transcription activator-like effector nuclease (TALEN) comprising an upstream DNA-binding domain linked to a DNA cleavage domain, wherein the upstream DNA binding domain specifically binds to a safe-harbor locus at a site upstream of a genomic insertion site, (b) a downstream transcription activator-like effector nuclease (TALEN) comprising a downstream DNA-binding domain linked to a DNA cleavage domain, wherein the downstream DNA binding domain specifically binds to a safe-harbor locus at a site downstream of the genomic insertion site, and (c) a single-stranded or double-stranded donor polynucleotide comprising sense and/or antisense strand polynucleotide overhangs that are complementary to corresponding polynucleotide overhangs of cleaved genomic DNA at the genomic insertion site, wherein said complementary overhangs facilitate homologous recombination of the donor polynucleotide with the cleaved genomic DNA, thereby introducing said polynucleotide into the genome of the cell.

Clause 32: The method of clause 31, wherein said upstream TALEN comprises SEQ ID NO:8.

Clause 33: The method of clause 31 or 32, wherein said downstream TALEN comprises SEQ ID NO:11.

Clause 34: The method of any one of clauses 31-33, wherein said DNA cleavage domain is derived from a FokI nuclease.

Clause 35: The method of clause 34, wherein the DNA cleavage domain derived from a FokI nuclease comprises SEQ ID NO: 13.

Clause 36: The method of anyone of clauses 31-35, wherein the upstream TALEN binds to the sense strand of a genomic DNA locus flanking the insertion site and the downstream TALEN binds to the antisense strand of a genomic DNA locus flanking the insertion site.

Clause 37: The method of any one of clauses 31-36, wherein said genomic insertion site is in any one of: a. the CLYBL safe harbor locus; b. an intron of the CLYBL safe harbor locus, or c. intron 2 of the CLYBL safe harbor locus.

Clause 38: The method of clause 37, wherein the genomic insertion site is within intron 2 of the CLYBL safe harbor locus.

Clause 39: The method of clause 36, wherein the genomic sense strand locus bound by the upstream TALEN comprises SEQ ID NO: 1.

Clause 40: The method of clause 36, wherein, the genomic antisense strand locus bound by the downstream TALEN comprises SEQ ID NO: 3.

Clause 41: The method of any one of clauses 31-40, wherein the polynucleotide is inserted into both copies of the same chromosome.

Clause 42: The method of clause 41, wherein said chromosome is human chromosome 13.

Clause 43: The method of any one of clauses 31-42, wherein the inserted polynucleotide encodes a product that is detectably labeled.

Clause 44: The method of any one of clauses 31-43, wherein the inserted polynucleotide comprises a selectable marker.

Clause 45: The method of any one of clauses 31-44, wherein the inserted polynucleotide is under the control of an inducible promoter.

Clause 46: A method of producing an induced pluripotent stem cell from a somatic cell comprising introducing into the somatic cell (a) an upstream transcription activator-like effector nuclease (TALEN) comprising an upstream DNA-binding domain linked to a DNA cleavage domain, wherein the upstream DNA binding domain specifically binds to a safe-harbor locus at a site upstream of a genomic insertion site, (b) a downstream transcription activator-like effector nuclease (TALEN) comprising a downstream DNA-binding domain linked to a DNA cleavage domain, wherein the downstream DNA binding domain specifically binds to a safe-harbor locus at a site downstream of the genomic insertion site, and (c) a single-stranded or double-stranded donor polynucleotide encoding one or more factors sufficient to convert a somatic cell into a pluripotent stem cell, comprising sense and/or antisense strand polynucleotide overhangs that are complementary to corresponding polynucleotide overhangs of cleaved genomic DNA at the genomic insertion site, wherein said complementary overhangs facilitate homologous recombination of the donor polynucleotide with the cleaved genomic DNA, thereby producing an induced pluripotent stem cell.

Clause 47: The method of clause 46, wherein said upstream TALEN comprises SEQ ID NO:8.

Clause 48: The method of clause 46 or 47, wherein said downstream TALEN comprises SEQ ID NO: 11.

Clause 49: The method of any one of clauses 46-48, wherein said DNA cleavage domain is derived from a FokI nuclease.

Clause 50: The method of clause 49, wherein the DNA cleavage domain derived from a FokI nuclease comprises SEQ ID NO: 13.

Clause 51: The method of anyone of clauses 46-50, wherein the upstream TALEN binds to the sense strand of a genomic DNA locus flanking the insertion site and the downstream TALEN binds to the antisense strand of a genomic DNA locus flanking the insertion site.

Clause 52: The method of any one of clauses 46-51, wherein said genomic insertion site is in any one of: a. the CLYBL safe harbor locus; b. an intron of the CLYBL safe harbor locus, or c. intron 2 of the CLYBL safe harbor locus.

Clause 53: The method of clause 52, wherein the genomic insertion site is within intron 2 of the CLYBL safe harbor locus.

Clause 54: The method of clause 51, wherein the genomic sense strand locus bound by the upstream TALEN comprises SEQ ID NO: 1.

Clause 55: The method of clause 51, wherein the genomic antisense strand locus bound by the downstream TALEN comprises SEQ ID NO: 3.

Clause 56: The method of any one of clauses 46-55, wherein the polynucleotide is inserted into both copies of the same chromosome.

Clause 57: The method of clause 56, wherein said chromosome is human chromosome 13.

Clause 58: The method of any one of clauses 46-57, wherein the inserted polynucleotide encodes a product that is detectably labeled.

Clause 59: The method of any one of clauses 46-58, wherein the inserted polynucleotide comprises a selectable marker.

Clause 60: The method of any one of clauses 46-59, wherein the inserted polynucleotide is under the control of an inducible promoter.

Clause 61: A method of inducing an induced pluripotent stem (iPS) cell to differentiate to a lineage-specific cell comprising introducing into the iPS cell (a) an upstream transcription activator-like effector nuclease (TALEN) comprising an upstream DNA-binding domain linked to a DNA cleavage domain, wherein the upstream DNA binding domain specifically binds to a safe-harbor locus at a site upstream of a genomic insertion site, (b) a downstream transcription activator-like effector nuclease (TALEN) comprising a downstream DNA-binding domain linked to a DNA cleavage domain, wherein the downstream DNA binding domain specifically binds to a safe-harbor locus at a site downstream of the genomic insertion site, and (c) a single-stranded or double-stranded donor polynucleotide encoding one or more factors sufficient to differentiate an iPS cell into a lineage-specific cell, comprising sense and/or antisense strand polynucleotide overhangs that are complementary to corresponding polynucleotide overhangs of cleaved genomic DNA at the genomic insertion site, wherein said complementary overhangs facilitate homologous recombination of the donor polynucleotide with the cleaved genomic DNA, thereby producing an lineage-specific cell.

Clause 62: The method of clause 61, wherein said factors sufficient to differentiate an iPS cell into a lineage-specific cell comprise one or more of: transforming growth factor beta (TGF-β), bone morphogenetic protein (BMP), NODAL, ACTIVIN, NOTCH, WNT, sonic hedgehog (SHH), or JAK/STAT.

Clause 63: The method of clause 61 or 62, wherein said upstream TALEN comprises SEQ ID NO:8.

Clause 64: The method of any one of clauses 61-63, wherein said downstream TALEN comprises SEQ ID NO:11.

Clause 65: The method of any one of clauses 61-64, wherein said DNA cleavage domain is derived from a FokI nuclease.

Clause 66: The method of clause 65, wherein the DNA cleavage domain derived from a FokI nuclease comprises SEQ ID NO: 13.

Clause 67: The method of anyone of clauses 61-66, wherein the upstream TALEN binds to the sense strand of a genomic DNA locus flanking the insertion site and the downstream TALEN binds to the antisense strand of a genomic DNA locus flanking the insertion site.

Clause 68: The method of any one of clauses 61-67, wherein said genomic insertion site is in any one of: a. the CLYBL safe harbor locus; b. an intron of the CLYBL safe harbor locus; or c. intron 2 of the CLYBL safe harbor locus.

Clause 69: The method of clause 68, wherein the genomic insertion site is within intron 2 of the CLYBL safe harbor locus.

Clause 70: The method of clause 67, wherein the genomic sense strand locus bound by the upstream TALEN comprises SEQ ID NO: 1.

Clause 71: The method of clause 67 and the genomic antisense strand locus bound by the downstream TALEN comprises SEQ ID NO: 3.

Clause 72: The method of any one of clauses 61-71, wherein the polynucleotide is inserted into both copies of the same chromosome.

Clause 73: The method of clause 72, wherein said chromosome is human chromosome 13.

Clause 74: The method of any one of clauses 61-73, wherein the inserted polynucleotide encodes a product that is detectably labeled.

Clause 75: The method of any one of clauses 61-74, wherein the inserted polynucleotide comprises a selectable marker.

Clause 76: The method of any one of clauses 61-75, wherein the inserted polynucleotide is under the control of an inducible promoter.

Clause 77: A method of treating a disease condition in a subject comprising expressing in a cell present in the subject a donor polynucleotide encoding one or more products capable of improving the disease condition, comprising introducing into the cell (a) an upstream transcription activator-like effector nuclease (TALEN) comprising an upstream DNA-binding domain linked to a DNA cleavage domain, wherein the upstream DNA binding domain specifically binds to a safe-harbor locus at a site upstream of a genomic insertion site, (b) a downstream transcription activator-like effector nuclease (TALEN) comprising a downstream DNA-binding domain linked to a DNA cleavage domain, wherein the downstream DNA binding domain specifically binds to a safe-harbor locus at a site downstream of the genomic insertion site, and (c) a single-stranded or double-stranded donor polynucleotide encoding one or more products sufficient to improve the disease condition, comprising sense and/or antisense strand polynucleotide overhangs that are complementary to corresponding polynucleotide overhangs of cleaved genomic DNA at the genomic insertion site, wherein said complementary overhangs facilitate homologous recombination of the donor polynucleotide with the cleaved genomic DNA, wherein the donor polynucleotide is inserted into the genomic insertion site and the disease condition improves following expression of the inserted donor polynucleotide.

Clause 78: The method of clause 77, wherein said factors sufficient to improve the disease condition comprise one or more of: CYBB (cytochrome b-245, beta polypeptide), CYBA (cytochrome b-245 alpha polypeptide), NCF1 (neutrophil cytosolic factor 1), NCF2 (neutrophil cytosolic factor 2), HBB (hemoglobin, beta), IL2RG (interleukin 2 receptor, gamma), ADA (adenosine deaminase), WAS (wiskott-aldrich syndrome), ABCD1 (ATP-binding cassette, sub-family D, member 1), PSMB8 (proteasome subunit, beta type, 8), PSMB4 (proteasome subunit, beta type, 4), PSMB9 (proteasome subunit, beta type, 9), and PSMA3 (proteasome subunit, alpha type, 3).

Clause 79: The method of clause 77 or 78, wherein said upstream TALEN comprises SEQ ID NO:8.

Clause 80: The method of any one of clauses 77-79, wherein said downstream TALEN comprises SEQ ID NO:11.

Clause 81: The method of any one of clauses 77-80, wherein said DNA cleavage domain is derived from a FokI nuclease.

Clause 82: The method of clause 81, wherein the DNA cleavage domain derived from a FokI nuclease comprises SEQ ID NO: 13.

Clause 83: The method of anyone of clauses 77-82, wherein the upstream TALEN binds to the sense strand of a genomic DNA locus flanking the insertion site and the downstream TALEN binds to the antisense strand of a genomic DNA locus flanking the insertion site.

Clause 84: The method of any one of clauses 77-83, wherein said genomic insertion site is in any one of: a. the CLYBL safe harbor locus; b. an intron of the CLYBL safe harbor locus, or c. intron 2 of the CLYBL safe harbor locus.

Clause 85: The method of clause 84, wherein the genomic insertion site is within intron 2 of the CLYBL safe harbor locus.

Clause 86: The method of clause 83, wherein the genomic sense strand locus bound by the upstream TALEN comprises SEQ ID NO: 1.

Clause 87: The method of clause 83, wherein the genomic antisense strand locus bound by the downstream TALEN comprises SEQ ID NO: 3.

Clause 88: The method of any one of clauses 77-87, wherein the polynucleotide is inserted into both copies of the same chromosome.

Clause 89: The method of clause 88, wherein said chromosome is human chromosome 13.

Clause 90: The method of any one of clauses 77-89, wherein the inserted polynucleotide encodes a product that is detectably labeled.

Clause 91: The method of any one of clauses 77-90, wherein the inserted polynucleotide comprises a selectable marker.

Clause 92: The method of any one of clauses 77-91, wherein the inserted polynucleotide is under the control of an inducible promoter.

Clause 93: The method of any one of clauses 77-92, wherein the polynucleotide inserted into the genome of said cell encodes a protein that assumes the role of a defective endogenous host protein.

Clause 94: A method of modifying the genomic DNA of a cell, comprising introducing into the cell (a) an upstream transcription activator-like effector nuclease (TALEN) comprising an upstream DNA-binding domain linked to a DNA cleavage domain, wherein the upstream DNA binding domain specifically binds to a site upstream of a genomic sequence of interest, and (b) a downstream transcription activator-like effector nuclease (TALEN) comprising a downstream DNA-binding domain linked to a DNA cleavage domain, wherein the downstream DNA binding domain specifically binds to a site downstream of a genomic sequence of interest, whereby the transcription activator-like effector nucleases cleave the genomic DNA and excise the genomic sequence of interest, thereby modifying the genomic DNA of the cell.

Clause 95: The method of clause 94, wherein the genome is modified by excision of a genome segment.

Clause 96: The method of any one of clauses 94 or 95, wherein said upstream TALEN comprises SEQ ID NO:8.

Clause 97: The method of any one of clauses 94 to 96, wherein said wherein said downstream TALEN comprises SEQ ID NO:11.

Clause 98: The method of any one of clauses 94-97, wherein said DNA cleavage domain is derived from a FokI nuclease.

Clause 99: The method of clause 98, wherein the DNA cleavage domain derived from a FokI nuclease comprises SEQ ID NO: 13.

Clause 100: The method of anyone of clauses 94-99, wherein the upstream TALEN binds to the sense strand of a genomic DNA locus flanking the sequence of interest and the downstream TALEN binds to the antisense strand of a genomic DNA locus flanking the sequence of interest.

Clause 101: The method of any one of clauses 94-100, wherein said genomic insertion site is in any one of: a. the CLYBL safe harbor locus; b. an intron of the CLYBL safe harbor locus, or c. intron 2 of the CLYBL safe harbor locus.

Clause 102: The method of clause 101, wherein the genomic sequence of interest is within intron 2 of the CLYBL safe harbor locus.

Clause 103: The method of clause 100, wherein the genomic sense strand locus bound by the upstream TALEN comprises SEQ ID NO: 1.

Clause 104: The method of clause 100, wherein the genomic antisense strand locus bound by the downstream TALEN comprises SEQ ID NO: 3.

Clause 105: The method of any one of clauses 94-104, wherein the polynucleotide is inserted into both copies of the same chromosome.

Clause 106: The method of clause 105, wherein said chromosome is human chromosome 13.

Clause 107: The method of any one of clauses 31-93, wherein the donor polynucleotide is single-stranded.

Clause 108: The method of any one of clauses 31-93, wherein the donor polynucleotide is double-stranded.

Clause 109: The method of any one of clauses 31-108, wherein the step of introducing comprises nucleofection.

Clause 110: The method of any one of clauses 31-109, wherein introducing the upstream TALEN and the downstream TALEN comprises transfecting the cell with a nucleic acid encoding the upstream TALEN and a nucleic acid encoding the downstream TALEN.

Clause 111: The method of clause 110, wherein a single vector comprises the nucleic acid encoding the upstream TALEN and the nucleic acid encoding the downstream TALEN.

Clause 112: The method of any one of clauses 46-60, wherein the factors sufficient to convert a somatic cell into a pluripotent stem cell is one or more of: Oct-3/4, Sox1, Sox2, Sox3, Sox15, Klf1, Klf2, Klf4, Klf5, c-myc, L-myc, N-myc, Nanog, LIN28, SV40 large T antigen, p53 shRNA, miR302b, miR302c, miR302a, miR302d, or miR367.

Clause 113: A method for introducing a polynucleotide of interest into a safe harbor locus in a genome of a neuronal stem cell, comprising: introducing into the neuronal stem cell (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site, wherein the complementary overhangs facilitate homologous recombination of the donor polynucleotide with the cleaved genomic DNA, thereby introducing the donor polynucleotide into the genomic insertion site into the safe harbor locus in the genome of the neuronal stem cell.

Clause 114: The method of clause 113, wherein the upstream TALEN binds to the sense strand of a genomic DNA locus flanking the insertion site and the downstream TALEN binds to the antisense strand of a genomic DNA locus flanking the insertion site.

Clause 115: The method of clause 113 or clause 114, wherein the neuronal stem cell is a long term neuronal stem cell (LT-NSC).

Clause 116: The method of any one of clauses 113-115, wherein the introducing comprises nucleofection.

Clause 117: The method of clause 116, wherein the introducing comprises the use of nucleofectin D.

Clause 118: The method of any one of clauses 113-117, comprising contacting the neuronal stem cell with the upstream TALEN, the downstream TALEN, and the polynucleotide of interest at a ratio of about 1:1:1.

Clause 119: The method of any one of clauses 113-118, wherein the donor polynucleotide encodes an agent for inducing the proliferation and/or differentiation of neuronal or glial cells.

Clause 120: The method of clause 119, wherein the agent is a trophic agent or a growth factor.

Clause 121: The method of clause 119, wherein the agent is nerve growth factor, insulin, fibroblast growth factor, glial derived neurotropic factor, a Notch ligand, Delta, brain derived neurotrophic factor, glial derived neurotrophic factor, bone morphogenic protein-2 or 4 (BMP-2/4), cilliarly neurotrophic factor (CNTF), heregulin-1 beta, platelet derived growth factor (PDGF)-1 or PDGF-B.

Clause 122: The method of any one of clauses 113-120, wherein the donor polynucleotide encodes a selectable marker and/or a detectable label.

Clause 123: The method of clause 122, wherein the donor polynucleotide comprises a lineage specific promoter operably linked to the selectable marker and/or detectable label.

Clause 124: The method of any one of clauses 113-121, wherein the safe harbor locus is CYBL.

Clause 125: The method of clause 124, wherein the genomic insertion site is within: a. an intron of the CLYBL safe harbor locus, or b. intron 2 of the CLYBL safe harbor locus.

Clause 126: The method of clause 124 or clause 125, wherein the donor polynucleotide encodes a polypeptide.

Clause 127: The method of any one of clauses 124-126, wherein the downstream TALEN comprises SEQ ID NO:11.

Clause 128: The method of any one of clauses 113-127, wherein the DNA cleavage domain comprises a FokI nuclease domain.

Clause 129: The method of clause 128, wherein the FokI nuclease domain comprises SEQ ID NO: 13.

Clause 130: The method of any one of clauses 113-129, wherein the genomic sense strand locus bound by the upstream TALEN comprises SEQ ID NO: 1.

Clause 131: The method of any one of clauses 113-129, wherein, the genomic antisense strand locus bound by the downstream TALEN comprises SEQ ID NO: 3.

Clause 132: The method of any one of clauses 113-131, wherein the donor polynucleotide is inserted into both copies of the same chromosome Clause 133. The method of any one of clauses 113-132, wherein the upstream TALEN comprises the amino acid sequence set forth as SEQ ID NO: 7.

Clause 134: The method of clause 133, wherein the upstream TALEN comprise the amino acid sequence set forth as SEQ ID NO: 8.

Clause 135: The method of any one of clauses 113-134, wherein the upstream TALEN comprises the amino acid sequence set forth as SEQ ID NO: 10.

Clause 136: The method of clause 135, wherein the downstream TALEN comprises the sequence of SEQ ID NO: 11.

Clause 137: The method of any one of clauses 113-136, wherein the cell comprises two copies of each chromosome, and wherein the polynucleotide is inserted into the two copies of the same chromosome.

Clause 138: A method of inducing a neuronal stem cell to differentiate to a neuronal or glial cell, comprising:

introducing into the neuronal stem cell (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site, wherein the complementary overhangs facilitate homologous recombination of the donor polynucleotide with the cleaved genomic DNA, thereby introducing the donor polynucleotide into the genome of the neuronal stem cell, wherein the donor polynucleotide encodes one or more factor sufficient to differentiate the neuronal stem cell into the neuronal or glial cell.

Clause 139: The method of clause 138, wherein the upstream TALEN binds to the sense strand of a genomic DNA locus flanking the insertion site and the downstream TALEN binds to the antisense strand of a genomic DNA locus flanking the insertion site.

Clause 140: The method of clause 138 or clause 139, wherein the neuronal stem cell is a long term neuronal stem cell (LT-NSC).

Clause 141: The method of any one of clauses 138-140, wherein the introducing comprises nucleofection.

Clause 142: The method of clause 141, wherein the nucleofection provides a transfection efficiency of at least 80%.

Clause 143: The method of any one of clauses 138-142, comprising contacting the neuronal stem cell with the upstream TALEN, the downstream TALEN, and the polynucleotide of interest at a ratio of about 1:1:1.

Clause 144: The method of any one of clauses 138-143, wherein the donor polynucleotide encodes a trophic agent and/or a growth factor.

Clause 145: The method of clause 144, wherein the donor polynucleotide encodes one or more of a nerve growth factor, insulin, fibroblast growth factor, glial derived neurotropic factor, a Notch ligand, Delta, brain derived neurotrophic factor, glial derived neurotrophic factor, bone morphogenic protein-2 or 4 (BMP-2/4), cilliarly neurotrophic factor (CNTF), heregulin-1 beta, platelet derived growth factor (PDGF)-1 and PDGF-B.

Clause 146: The method of any one of clauses 138-145, wherein the donor polynucleotide encodes a selectable marker and/or a detectable label.

Clause 147: The method of clause 146, wherein the donor polynucleotide comprises a neuronal specific promoter operably linked to the selectable marker and/or detectable label.

Clause 148: The method of any one of clauses 138-147, wherein the safe harbor locus is CYBL.

Clause 149: The method of clause 148, wherein the genomic insertion site is within: a. an intron of the CLYBL safe harbor locus; or b. intron 2 of the CLYBL safe harbor locus.

Clause 150: The method of any one of clauses 138-149, wherein the upstream TALEN comprises SEQ ID NO:8.

Clause 151: The method of any one of clauses 138-150, wherein the downstream TALEN comprises SEQ ID NO:11.

Clause 152: The method of any one of clauses 138-151, wherein the DNA cleavage domain comprises a FokI nuclease domain.

Clause 153: The method of clause 152, wherein the FokI nuclease domain comprises SEQ ID NO: 13.

Clause 154: The method of any one of clauses 138-153, wherein the genomic sense strand locus bound by the upstream TALEN comprises SEQ ID NO: 1.

Clause 155: The method of any one of clauses 138-154, wherein, the genomic antisense strand locus bound by the downstream TALEN comprises SEQ ID NO: 3.

Clause 156: The method of any one of clauses 138-155, wherein the donor polynucleotide is inserted into both copies of the same chromosome Clause 157: The method of any one of clauses 138-156, wherein the upstream TALEN comprises the amino acid sequence set forth as SEQ DI NO: 7.

Clause 158: The method of clause 157, wherein the upstream TALEN comprise the amino acid sequence set forth as SEQ ID NO: 8.

Clause 159: The method of any one of clauses 138-158, wherein the upstream TALEN comprises the amino acid sequence set forth as SEQ ID NO: 10.

Clause 160: The method of clause 159, wherein the downstream TALEN comprises the sequence of SEQ ID NO: 11.

Clause 161: The method of any one of clauses 138-160, wherein the cell comprises two copies of each chromosome, and wherein the polynucleotide is inserted into the two copies of the same chromosome.

Clause 162: A method for treating a neurodegenerative disorder, stroke or a nerve injury in a subject, comprising selecting a subject with a neurodegenerative disorder or a spinal cord injury; and administering a therapeutically effective amount of a neuronal stem cell or cells differentiated from the neuronal stem to the subject, wherein the neuronal stem cell is produced by the method of:

introducing into the neuronal stem cell (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and optionally (c) a single or double-stranded donor polynucleotide comprising sense and/or antisense strand polynucleotide overhangs that are complementary to corresponding polynucleotide overhangs of cleaved the genomic DNA when cleaved at the genomic insertion site, wherein the complementary overhangs facilitate homologous recombination of the donor polynucleotide with the cleaved genomic DNA, thereby introducing the donor polynucleotide into the genome of the neuronal stem cell;

thereby treating the neurodegenerative disease, stroke or the spinal cord injury in the subject.

Clause 163: The method of clause 162, wherein the neurodegenerative disease is Parkinson's disease.

Clause 164: The method of clause 162, wherein the nerve injury is a spinal cord injury.

Clause 165: The method of clause 164, wherein the spinal cord injury is a partially transected spinal cord.

Clause 166: The method of clause 162, wherein the nerve injury is a peripheral nerve injury.

Clause 167. The method of clause 162, wherein the subject has had a stroke or brain trauma.

Clause 168: The method of any one of clauses 162-167, wherein the neuronal stem cells or cell differentiated therefrom are administered locally.

Clause 169: The method of any one of clauses 162-168, wherein the upstream TALEN binds to the sense strand of a genomic DNA locus flanking the insertion site and the downstream TALEN binds to the antisense strand of a genomic DNA locus flanking the insertion site.

Clause 170. The method of any one of clauses 162-169, wherein the neuronal stem cell is a long term neuronal stem cell (LT-NSC).

Clause 171: The method of any one of clauses 162-170, wherein the introducing comprises nucleofection.

Clause 172: The method of clause 171, wherein the nucleofection provides a transfection efficiency of at least 80%.

Clause 173: The method of any one of clauses 162-172, comprising contacting the neuronal stem cell with the upstream TALEN, the downstream TALEN, and the polynucleotide of interest at a ratio of about 1:1:1.

Clause 174: The method of any one of clauses 162-173, wherein the double-stranded donor polynucleotide is introduced into the neuronal stem cell, and wherein the donor polynucleotide encodes a trophic agent and/or a growth factor.

Clause 175: The method of any one of clauses 162-174, wherein the double-stranded donor polynucleotide is introduced into the neuronal stem cell, and wherein the donor polynucleotide encodes one or more of nerve growth factor, fibroblast growth factor, glial derived neurotropic factor, insulin, a Notch ligand, Delta, brain derived neurotrophic factor, glial derived neurotrophic factor, bone morphogenic protein-2 or 4 (BMP-2/4), cilliarly neurotrophic factor (CNTF), heregulin-1 beta, platelet derived growth factor (PDGF)-1 and PDGF-B.

Clause 176: The method of any one of clauses 162-175, wherein the double-stranded donor polynucleotide is introduced into the neuronal stem cell, and wherein the donor polynucleotide encodes a selectable marker and/or a detectable label.

Clause 177: The method of clause 176, wherein the donor polynucleotide comprises a neuronal specific promoter operably linked to the selectable marker and/or detectable label.

Clause 178: The method of any one of clauses 162-177, wherein the safe harbor locus is CYBL.

Clause 179: The method of clause 178, wherein the genomic insertion site is within: a. an intron of the CLYBL safe harbor locus, or b. intron 2 of the CLYBL safe harbor locus.

Clause 180: The method of any one of clauses 162-179, wherein the upstream TALEN comprises SEQ ID NO:8.

Clause 181: The method of any one of clauses 162-180, wherein the downstream TALEN comprises SEQ ID NO:11.

Clause 182: The method of any one of clauses 162-181, wherein the DNA cleavage domain comprises a FokI nuclease domain.

Clause 183: The method of clause 182, wherein the FokI nuclease domain comprises SEQ ID NO: 13.

Clause 184: The method of any one of clauses 162-183, wherein the genomic sense strand locus bound by the upstream TALEN comprises SEQ ID NO: 1.

Clause 185: The method of any one of clauses 162-184, wherein, the genomic antisense strand locus bound by the downstream TALEN comprises SEQ ID NO: 3.

Clause 186: The method of any one of clauses 162-185, wherein the donor polynucleotide is inserted into both copies of the same chromosome Clause 187: The method of any one of clauses 162-186, wherein the upstream TALEN comprises the amino acid sequence set forth as SEQ DI NO: 7.

Clause 188: The method of clause 187, wherein the upstream TALEN comprise the amino acid sequence set forth as SEQ ID NO: 8.

Clause 189: The method of any one of clauses 162-188, wherein the upstream TALEN comprises the amino acid sequence set forth as SEQ ID NO: 10.

Clause 190: The method of any one of clauses 162-189, wherein the downstream TALEN comprises the sequence of SEQ ID NO: 11.

Clause 191: The method of any one of clauses 162-190, wherein the cell comprises two copies of each chromosome, wherein the double-stranded donor polynucleotide is introduced into the neuronal stem cell, and wherein the polynucleotide is inserted into the two copies of the same chromosome.

Clause 192: A method of modifying the genomic DNA of a neuronal stem cell, comprising introducing into the cell (a) an upstream transcription activator-like effector nuclease (TALEN) comprising an upstream DNA-binding domain linked to a DNA cleavage domain, wherein the upstream DNA binding domain specifically binds to a site upstream of a genomic sequence of interest, and (b) a downstream transcription activator-like effector nuclease (TALEN) comprising a downstream DNA-binding domain linked to a DNA cleavage domain, wherein the downstream DNA binding domain specifically binds to a site downstream of a genomic sequence of interest, whereby the transcription activator-like effector nucleases cleave the genomic DNA and excise the genomic sequence of interest, thereby modifying the genomic DNA of the cell.

Clause 193: The method of clause 192, wherein the genome is modified by excision of a genome segment.

Clause 194: The method of any one of clauses 192 or 193, wherein the upstream TALEN comprises SEQ ID NO:8.

Clause 195: The method of any one of clauses 192 to 194, wherein the wherein the downstream TALEN comprises SEQ ID NO:11.

Clause 196: The method of any one of clauses 192-195, wherein the DNA cleavage domain comprises a FokI nuclease.

Clause 197: The method of clause 196, wherein the DNA cleavage domain derived from a FokI nuclease comprises SEQ ID NO: 13.

Clause 198: The method of anyone of clauses 192-197, wherein the upstream TALEN binds to the sense strand of a genomic DNA locus flanking the sequence of interest and the downstream TALEN binds to the antisense strand of a genomic DNA locus flanking the sequence of interest.

Clause 199: The method of any one of clauses 192-198, wherein the genomic sequence of interest is in the CLYBL safe harbor locus.

Clause 200: The method of clause 199, wherein the genomic sequence of interest is within: a. an intron of the CLYBL safe harbor locus; or b. intron 2 of the CLYBL safe harbor locus.

Clause 201: The method of any one of clause 198, wherein the genomic sense strand locus bound by the upstream TALEN comprises SEQ ID NO: 1.

Clause 202: The method of clause 198, wherein the genomic antisense strand locus bound by the downstream TALEN comprises SEQ ID NO: 3.

Clause 203: The method of any one of clauses 192-202, wherein the polynucleotide is inserted into both copies of the same chromosome.

Clause 204: The method of clause 199 or clause 200, wherein the chromosome is human chromosome 13.

Clause 205: The method of any one of clauses 138-204 wherein introducing comprises the use of nucleofection.

Clause 206: The method of clause 205, wherein the nucleofectin provides a transfection efficiency of at least 80%.

Clause 207: The method of any one of clauses 113-206, wherein introducing the upstream TALEN and the downstream TALEN comprises transfecting the cell with a nucleic acid encoding the upstream TALEN and a nucleic acid encoding the downstream TALEN.

Clause 208: The method of clause 207, wherein a single vector comprises the nucleic acid encoding the upstream TALEN and the nucleic acid encoding the downstream TALEN.

Clause 209: A method of assessing the physiological effect of a polypeptide on a neuronal stem cell comprising
introducing into the neuronal stem cell (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site, wherein the complementary overhangs facilitate homologous recombination of the donor polynucleotide with the cleaved genomic DNA, thereby introducing the polynucleotide into the genome of the cell; and assessing a parameter of the neuronal stem cell, thereby determining the physiological effect of the polypeptide on the neuronal stem cell.

Clause 210: The method of clause 209, wherein the parameter is division of the neuronal stem cell.

Clause 211: The method of clause 209, wherein the parameter is differentiation of the neuronal stem cell.

Clause 212: The method of clause 162, further comprising: selecting a neuronal stem cell; and introducing into the neuronal stem cell (a) an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the neuronal stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and optionally (c) a single or double-stranded donor polynucleotide comprising sense and/or antisense strand polynucleotide overhangs that are complementary to corresponding polynucleotide overhangs of cleaved the genomic DNA when cleaved at the genomic insertion site, wherein the complementary overhangs facilitate homologous recombination of the donor polynucleotide with the cleaved genomic DNA, thereby introducing the donor polynucleotide into the genome of the neuronal stem cell, prior to administering the therapeutically effective amount of the neuronal stem cell or cells differentiated from the neuronal stem to the subject.

Clause 213: The method of any one of clauses 113-191 or 207-209, wherein the donor polynucleotide is single-stranded.

Clause 214: The method of any one of clauses 113-191 or 207-209, wherein the donor polynucleotide is double-stranded.

Clause 215: The method of any one of clauses 113-214, wherein introducing the upstream TALEN and the downstream TALEN comprises transfecting the cell with a nucleic acid encoding the upstream TALEN and a nucleic acid encoding the downstream TALEN.

EXAMPLES

The disclosure is illustrated by the following non-limiting Examples.

Example 1

Figure 3A:
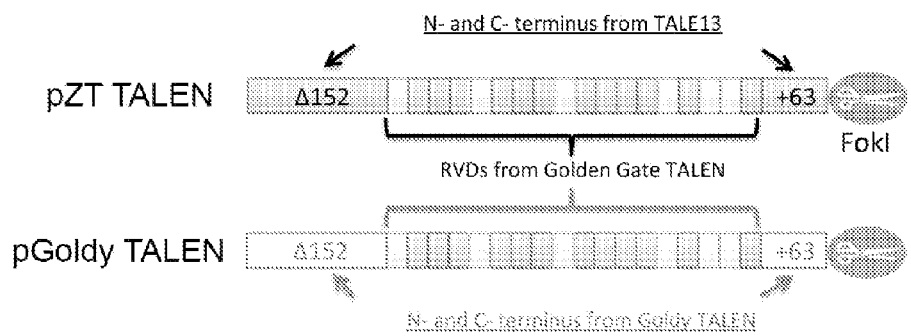
FIGS. 3A-3C. Validation of pZT TALENs in 293T cells. (A) Scheme of pZT-TALEN vector vs Goldy TALEN vector. They use the same RVD units from Golden Gate Assembly Kit (Addgene) and both have shortened Δ152 N-terminus and +63 C-terminus. However, the origins of N-/C-terminus are different between pZT and Goldy TALEN vectors. (B). Time course of GFP % in pZT-AAVS1-TALEN, Goldy AAVS1-TALEN or AAVS1-CRISPR/Cas targeted 293T cells suggested they have similar genome editing efficiency. (C) Ratio of donor:TALENs affects gene targeting efficiency in 293T cells. pZT-AAVS1 TALEN in GFP rescue assay was used to measure genome editing efficiency at day 3 after transfection.
Figure 3B:
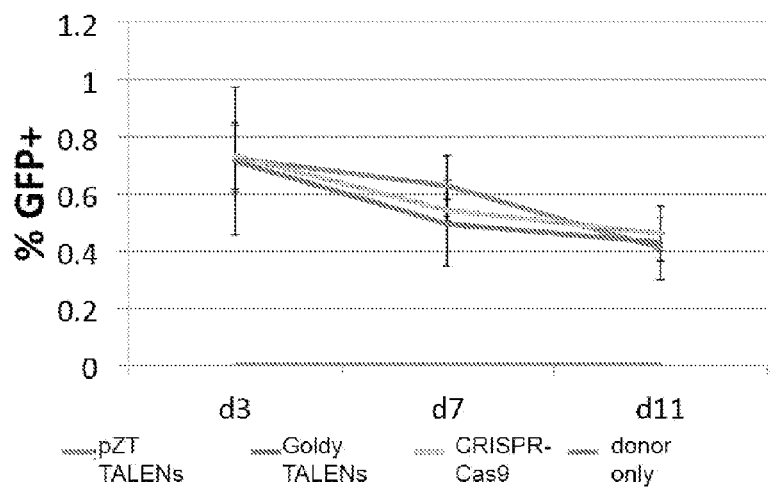
Figure 3C:
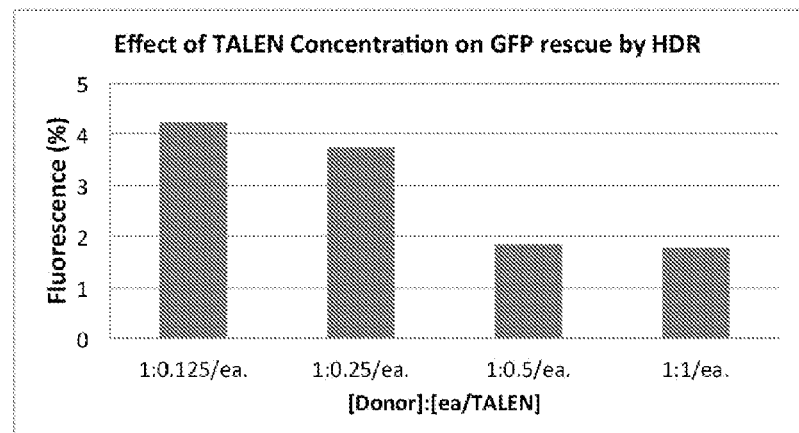
Figure 4A:
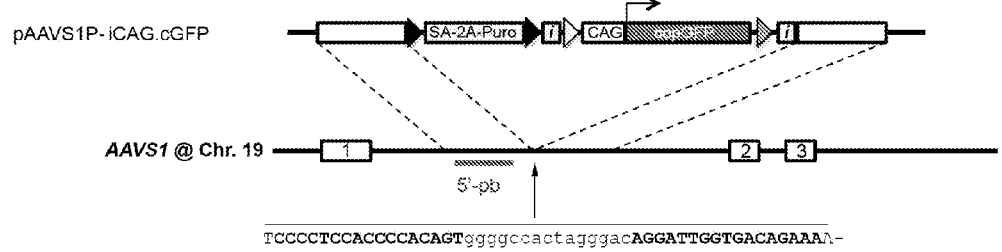
FIGS. 4A-4F. iCAG.copGFP reporter knock-in at AAVS1 locus in iPSCs. (A) Scheme of the targeting donor containing loxP (black triangle), lox2272 (white triangle), lox551 (grey triangle), insulator (i), and CAG-driven copGFP which will be inserted into an intron 1 sequence (arrow) of PPP1R12C gene. (B) Southern blot of pAAVS1P-iCA-G.cGFP targeted NCRM5 iPSC clones. Red=1TI; Green=2TI. (C) Normal karyotype of NCRM5-AS1-iCA-GcGFP clones 9 (D) pluripotent surface marker staining of undifferentiated NCRM5-AS1-iCAGcGFP clone 9 (E-F) teratoma formation of NCRM5-AS1-iCAGcGFP clone 10 showed persistent copGFP expression and three germ layers differentiation capacity.
Figure 4B:
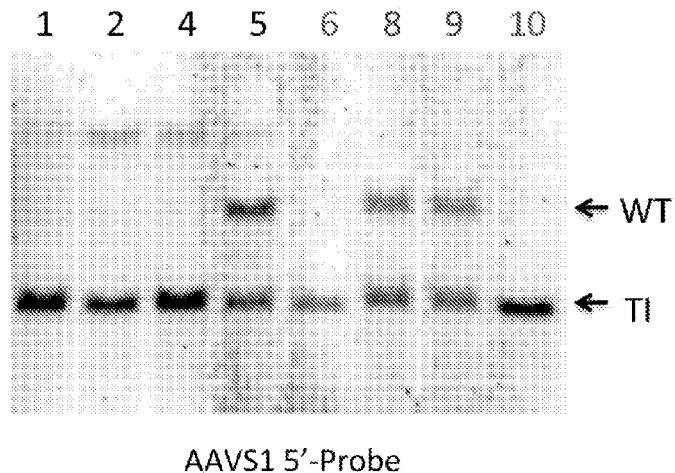
Figure 4C:
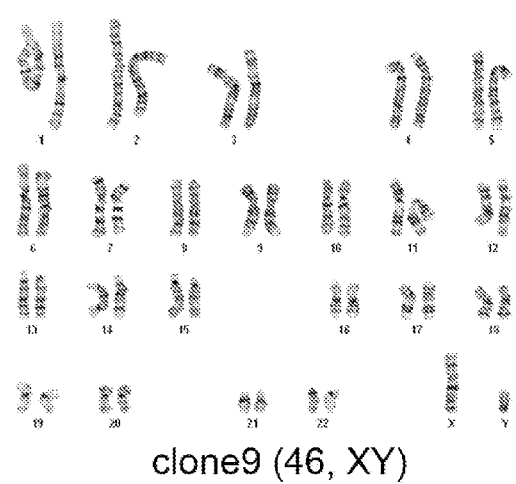
Figure 4D:
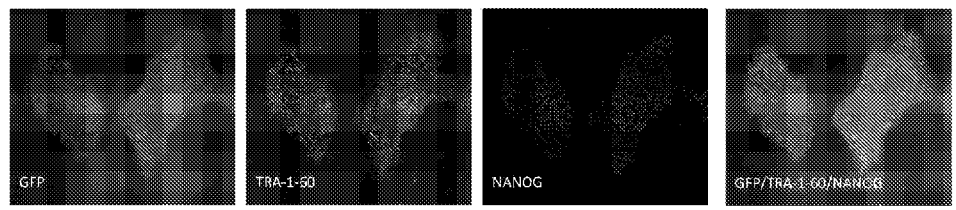
Figure 4E:
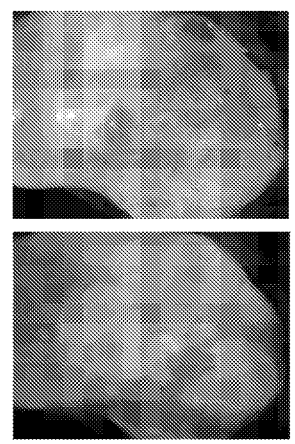
Figure 4F:
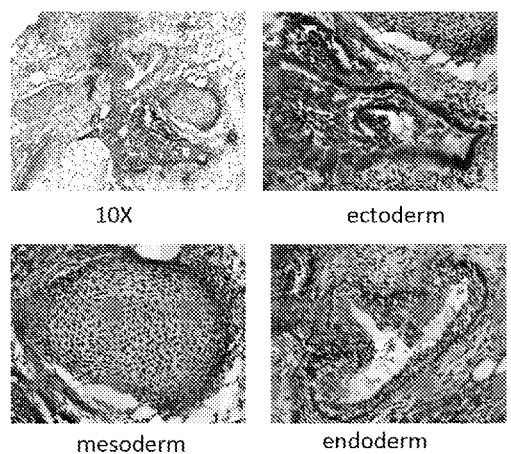
Figure 5A:
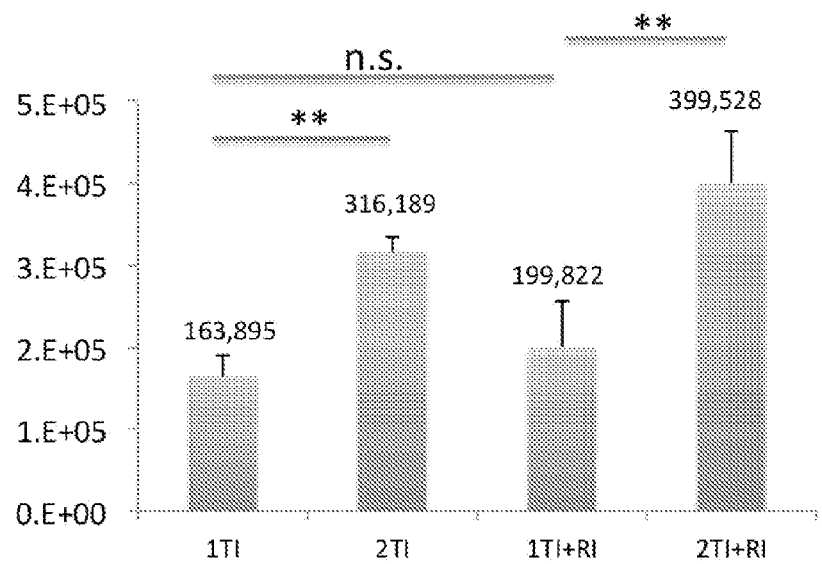
FIGS. 5A-5B. TI copy number-dependent GFP reporter expression at AAVS1 safe harbor. (A) Summary of GFP mean fluorescent intensity (MFI) in clones with single TI (1TI), double TI (2T), and additional RI (1TI+RI or 2TI+RI). Comparisons show 2TI clones have significantly higher expression than 1TI clones (p<0.01, **) with nearly double MFI (Y-axis). Additional RI does not significantly (n.s.) increase expression level (1TI+RI vs. 1TI, p>0.1). copGFP and eGFP clones are grouped together based on integration profile. N>=3. Error bar=S.E.M. (B) Flow cytometry histogram of NCRM5-AS1-iCAGcGFP clones, showing difference of fluorescence intensities among 1TI, 2TI, and 2TI+RI clones.
Figure 5B:
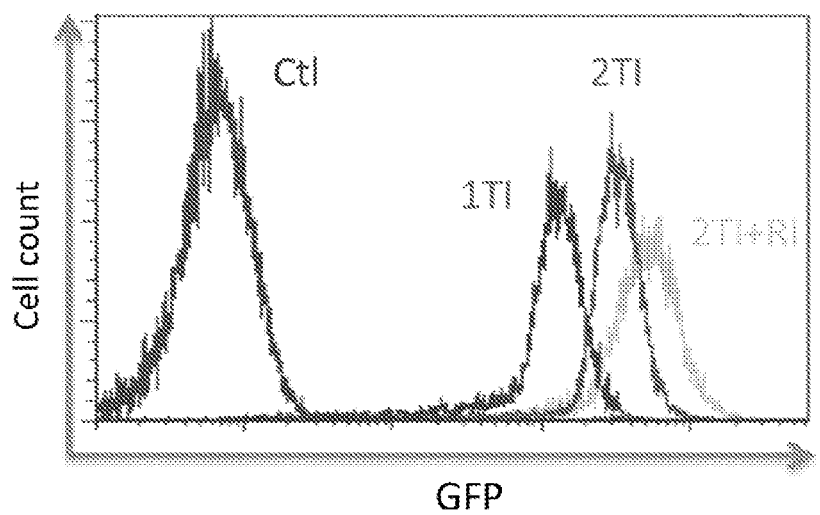
Figure 7A:
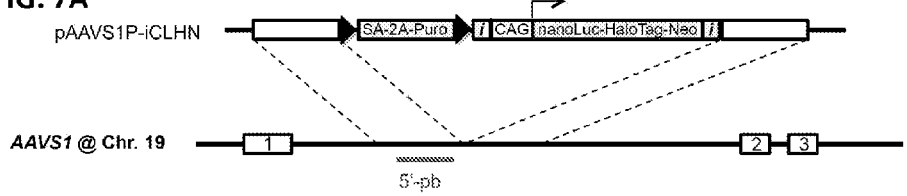
FIGS. 7A-7E. iCLHN reporter knock-in at AAVS1 locus in iPSCs. (A) Scheme of iCLHN donor targeting at AAVS1, similar to FIG. 1A, but with different homology arms. (B) Southern blot of pAAVS1-iCLHN targeted clones. Red=1TI, Green=2TI. (C) Normal karyotype of NCRM5-AS1-iCLHN clone 11. (D-E) Clone 11 shows pluripotent markers in iPSC culture (D), and forms teratoma with three germ layer lineages during in vivo differentiation (E).
Figure 7B:
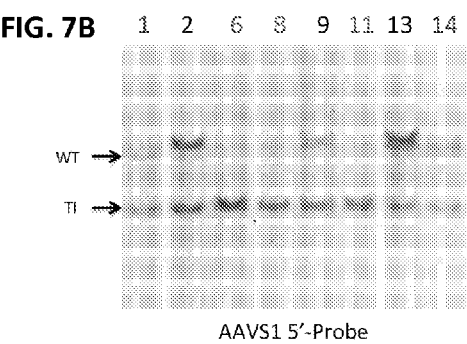
Figure 7C:
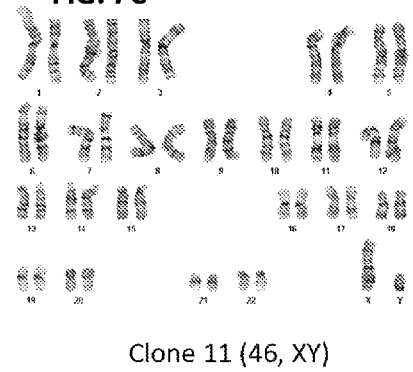
Figure 7D:
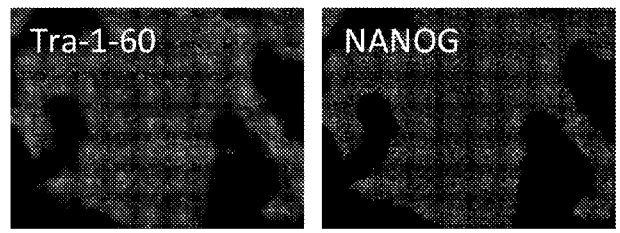
Figure 7E:
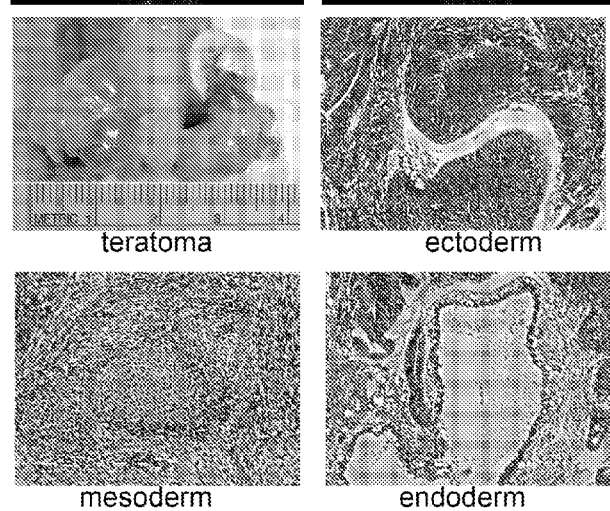

Multiplexed Reporter Knock-in at Safe-Harbor Loci in Human iPSCs and Neural Stem Cells It was reasoned that gene targeting at safe harbors which are usually actively transcribed region should provide a large transgene knock-in and sustained transgene expression. TALENs have been known to have both high activity and specificity. A TALEN mammalian expression vector was designed based on original Golden Gate TALEN (Cermak et al., *Nucleic Acids Res* 39, e82 (2011)). RVDs and truncated N-/C-terminus from TALE13 (Miller et al., *Nat Biotechnol* 29, 143-148 (2011)) because Golden Gate assembly method provided nearly 100% successful rate for quick and easy manual TALEN construction and truncated TALE terminus showed higher activity than wild-type (Bedell, *Nature* 491, 114-118 (2012)). Using an AAVS1 target sequence, a TALEN expression vector—pZT—was tested by comparing pZT-AAVS1 TALENs with pGoldy-AAVS1 TALENs, which have different truncated N-/C-terminus (Bedell et al., supra) and AAVS1-CRISPR (Mali et al., *Science* 339, 823-826 (2013)). It was determined that they all perform similarly (FIG. 3). The pZT TALEN backbone was thus validated.

Using pZT-AAVS1 TALENs, an integration-free human iPSC line NCRM5 was targeted with an improved AAVS1 donor expressing a constitutive CAG promoter-driven copGFP reporter flanked by cHS4 insulators to prevent potential gene silencing. After nucleofection delivery of both TALENs and donor plasmids, targeted iPSC clones were selected by puromycin-resistant gene expressed from endogenous PPP1R12C promoter. All surviving iPSC clones showed targeted integration (TI), maintain pluripotency and normal karyotype (FIG. 4). In the clone where only correctly targeted integration occurred, the copGFP expression is not only robust, but also proportional to the number of targeted alleles, with double-allele TI clones showing twice as much mean fluorescence intensity (MFI) as single TI clones (MFI=316 k vs 164 k). Clones with additional random integration (RI) showed larger variation of MFI, probably because some RIs resulted additional fluorescence signal and some are silenced (FIG. 4).

Figure 1B:
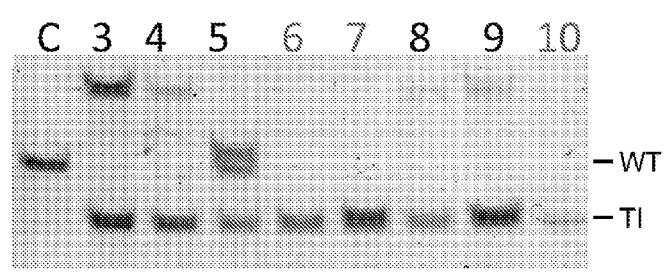

The human CLYBL gene in Chromosome 13 (Thyagarajan et al., *Stem cells* 26, 119-126 (2008)) that is a pseudosite for phiC31 random integration, was targeted. Re-targeting of a pre-integrated R4 integrase site at CLYBL allows robust transgene expression in human embryonic stem cells and their differentiated lineages (Liu et al., *Stem cells and development* 18, 1459-1472 (2009)), likely because CLYBL locus is transcriptionally active in almost all human cell types (see the biogps.org website). These data suggested CLYBL is a potential safe-harbor locus. To directly target CLYBL safe-harbor in any human cells without pre-engineering, a unique TALEN target sequence at CLYBL locus was identified. To avoid the low specificity of NN RVD targeting G, a TALEN target sequence composed of only A, C, or T was chosen, and identified in intron 2 of CLYBL. The CLYBL TALENs (also termed as C13 TALENs) constructed using pZT backbone showed 25% NHEJ gene editing efficiency in human 293T cells measured by both T7E1 mismatch assay and targeted sequencing (FIG. 6). To compare transgene expression at AAVS1 and CLYBL loci, an 8 kb insulator-flanked cassette expressing CAG-driven Nanoluc-HaloTag fusion protein was targeted in either locus (FIGS. 1A and 7). Since CLYBL is actively expressed in human stem cells, a splicing acceptor (SA)-2A-linked drug-selection was used to enrich targeted cells. All drug-selected clones contain targeted integration at either locus and are pluripotent based on in vitro and in vivo differentiation assays (Table 1, FIGS. 1B, 7 and 8).

TABLE 1

Summary of safe harbor targeted iPSCs.

| Locus | donor | 1TI-only (%) | 2TI-only (%) | TI-only (%) | 1TI + RI (%) | 2TI + RI (%) |
|---|---|---|---|---|---|---|
| AAVS1 | iCAGcGFP or CAGeGFP | 8/24 (33%) | 2/24 (8%) | 10/24 (42%) | 8/24 (33%) | 6/24 (25%) |
| AAVS1 | iCLHN | 5/14 (36%) | 3/14 (21%) | 8/14 (57%) | 4/14 (29%) | 2/14 (14%) |
| C13 | iCLHN | 0/8 (0%) | 3/8 (38%) | 3/8 (38%) | 1/8 (12%) | 4/8 (50%) |
| AAVS1 | iCAGtdTom | 8/19 (42%) | 7/19 (37%) | 15/19 (79%) | 3/19 (16%) | 1/9 (5%) |
| C13 | iCAGcGFP | 9/28 (32%) | 6/28 (21%) | 15/28 (54%) | 5/28 (18%) | 6/28 (21%) |

Figure 1C:
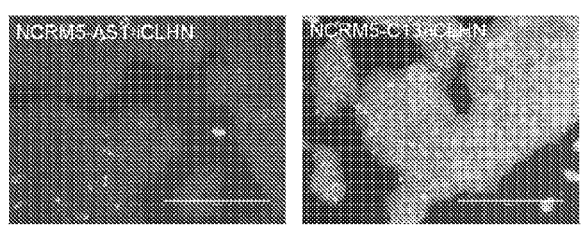
Figure 1D:
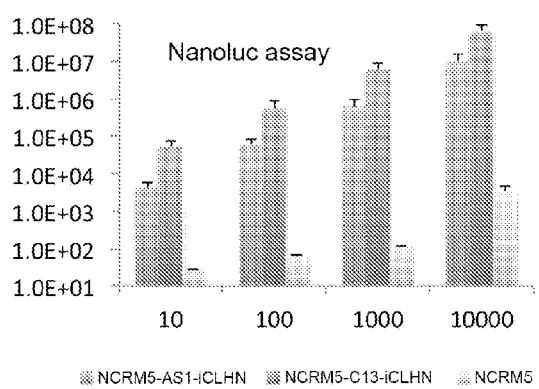

Since random integration may add unpredicted transgene expression, double TI-only clones were focused on, and a ~10-fold higher Nanoluc expression was observed, measured by luminometer (RLU=54177 vs 4314 at 10 cells, 567442 vs 59997 at 100 cells, 6008183 vs 626662 at 1000 cells) and ~5-folder higher HaloTag expression by oregon-green ligand staining and flow cytometry (MFI=592 k vs 114 k) in CLYBL locus than AAVS1 locus (FIG. 1C-D, S6). Furthermore, CLYBL-targeted and AAVS1-targeted clones showing ~1000-fold and ~100-fold higher expression than the negative control cells (RLU=27 at 10 cells), respectively, suggesting Nanoluc is a very sensitive reporter to detect expression from 10 or potentially even less cells due to its extremely bright signal and low background (FIG. 1D). CAG-driven copGFP expression was compared at AAVS1 and CLYBL safe harbors, and it was found that copGFP expression is also ~5-fold higher in CLYBL targeted iPSC clones than AAVS1 targeted clones (FIG. 8).

Figure 1E:
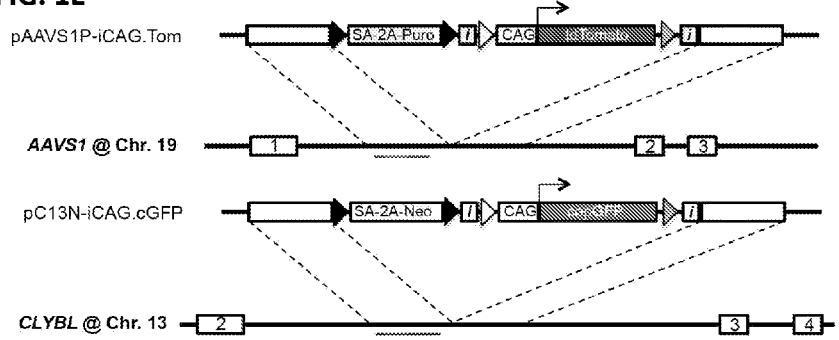
Figure 1F:
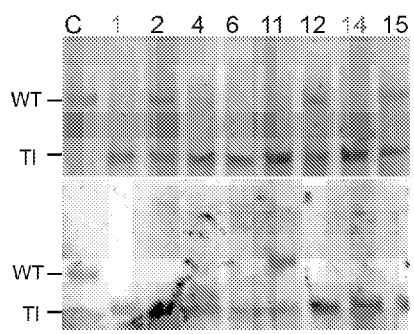
Figure 1G:
Figure 10A:
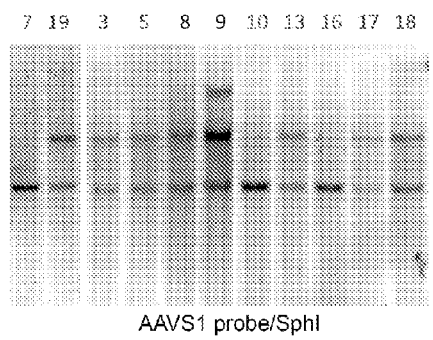
FIGS. 10A-10B. Southern analysis dual safe harbor targeted iPSC clones. (A) Clone gDNA were digested by SphI and analyzed using AAVS1 Probe. WT=6.5 kb, TI=3.8 kb. (B) Clone gDNA were digested by BamHI and analyzed using CLYBL Probe. WT=4.4 kb, TI=11.2 kb. Clone numbers are on the top of the blots, Red=1TI, Green=2TI.
Figure 10B:
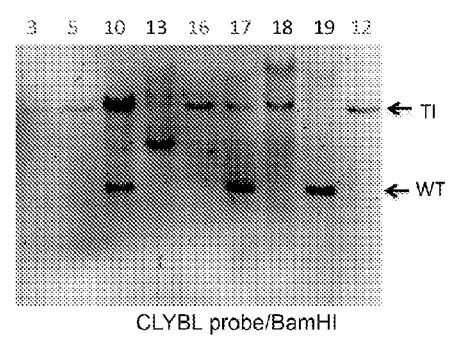
Figure 11A:
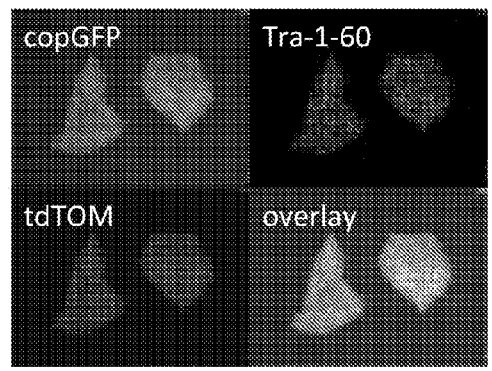
FIGS. 11A-11E. Characterization of dual safe harbor targeted iPSC NCRM5-AS1Tom-C13GFP clone 1. (A) Pluripotent surface marker TRA-1-60 is co-expressed with both tdTomato and copGFP. (B) Normal karyotype. (C) Fluorescent microscopy (only GFP channel is shown) and H&E staining of teratoma, showing three germ layer lineages. (D) After 8-week in vivo differentiation, teratoma cells still show persistent dual transgene expression by flow cytometry. (E). In vitro differentiation into three germ layer lineages.
Figure 11B:
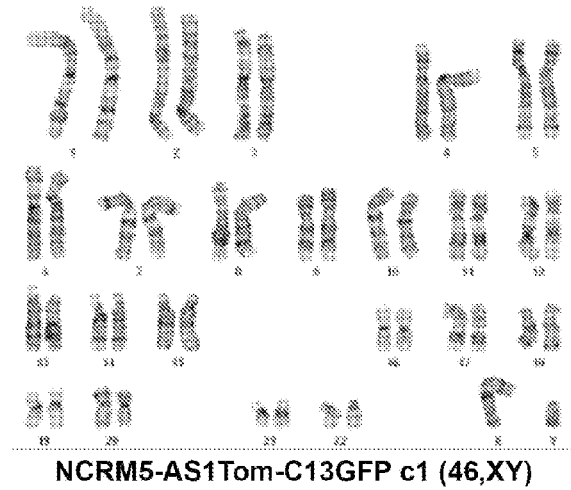
Figure 11C:
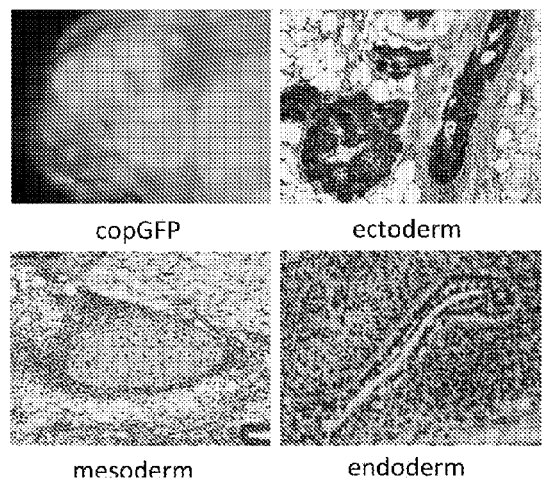
Figure 11D:
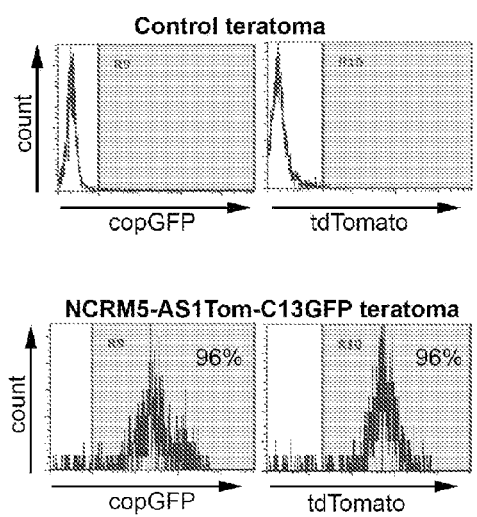
Figure 11E:
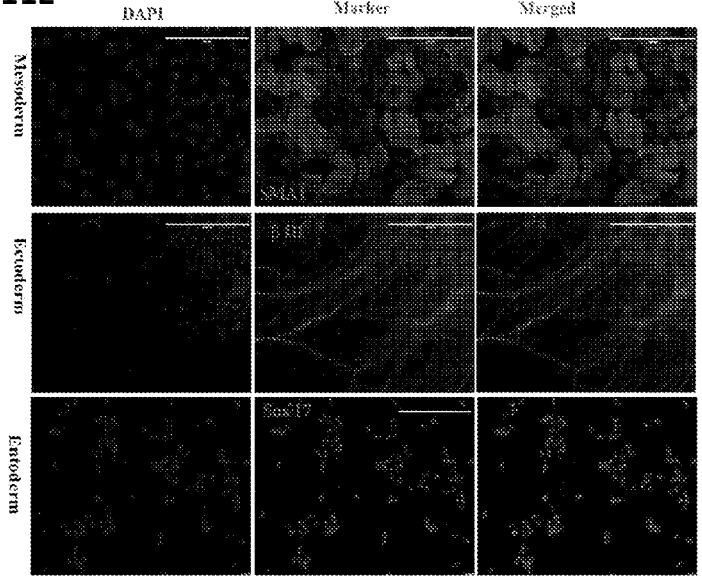

Encouraged by the highly active AAVS1 and CLYBL TALENs, both safe-harbors were simultaneously targeting by knocking-in two different donors expressing either tdTomato or copGFP at AAVS1 or CLYBL locus, respectively (FIG. 1E). Surprisingly, the co-transfection efficiency of multiple donors was only slightly lower than that of single donor (68% co-transfection vs 70-80% single transfection, FIG. 9) using nucleofection. Dual-color clones were readily isolated after double drug-selection. 14/16 clones are confirmed by Southern analysis to have both safe harbors targeted, ranging from 1 allele for each safe harbor to all 4 alleles for both (FIGS. 1F and 10). The double safe harbor-targeted clones maintain normal karyotype, iPSC morphology and surface markers, and robust fluorescent protein expression without observed silencing during extended culture (FIGS. 1G and 11). They also efficiently differentiate into three germ layers by in vivo teratoma formation and in vitro spontaneous embryoid body formation, and directed differentiate into beating cardiomyocytes showing both fluorescent gene expression (FIG. 11).

Figure 2A:
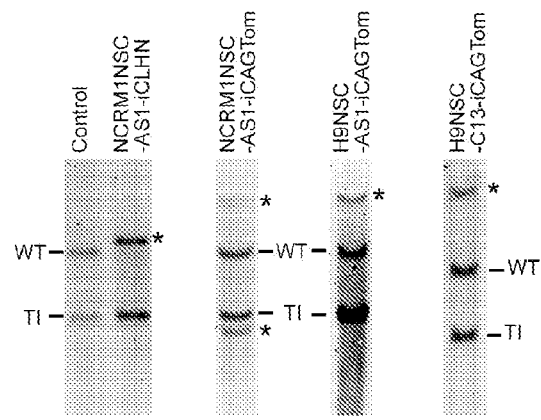
Figure 2B:
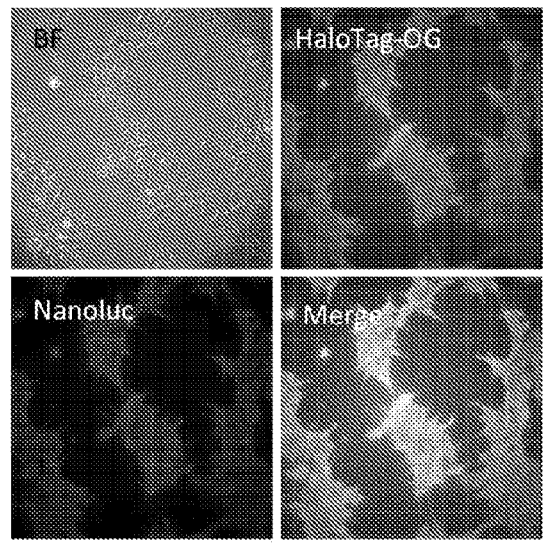
Figure 12A:
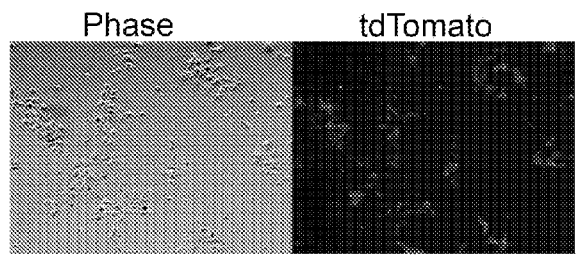
FIG. 12A-12B. Nucleofection efficiency in human NSCs.
Figure 12B:
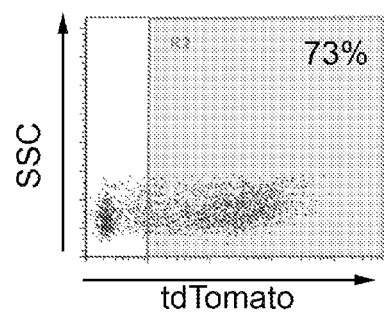
Figure 13A:
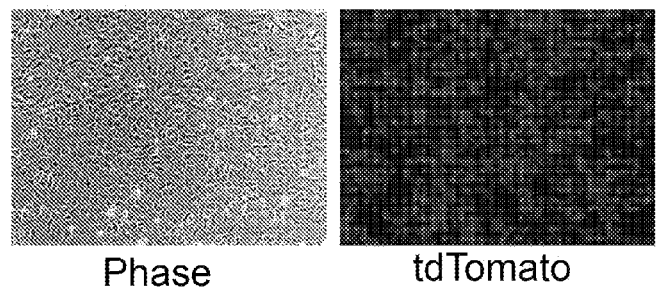
FIGS. 13A-13B. Robust tdTomato reporter expression in CLYBL targeted NSCs. (A) pC13N-iCAG.Tom targeted H9NSCs show strong tdTomato expression. (B) Tuj1+ neurons differentiated from H9NSC-C13-iCAGTom show robust tdTomato expression.
Figure 13B:
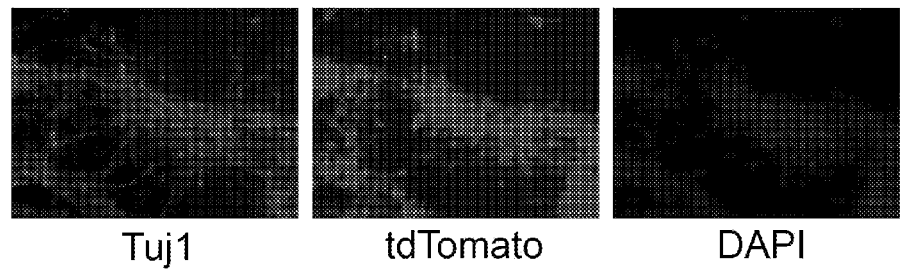

The high-efficiency of TALEN-mediated safe harbor gene addition suggests it is possible to direct targeted self-renewing somatic stem cells. Neural stem cells (NSCs) differentiated from pluripotent stem cells were chosen, as NSCs proliferate and maintain their mulitpotency extensively by in vitro culture (Swistowski et al., *PloS one* 4, e6233 (2009)). The nucleofection protocol was optimized for NSCs; a 60-90% transfection efficiency was achieved (FIG. 12) using nucleofector 4D, program# DN-100, and 2 ug total DNA/million NSCs. Using AAVS1 or CLYBL TALENs together with safe harbor targeting donors described in iPSC targeting, a reporter knock-in was attempted at single safe-harbor, AAVS1 or CLYBL, in NCRM1 iPSC derived NSC (NCRM1NSC) or H9 ESC derived NSC (H9NSC). After drug selection a polyclonal population was obtained, with nearly 100% expressing reporter genes, either Nanoluc-HaloTag or tdTomato. In NCRM1NSC-AS1-iCLHN cells, Southern blot showed that all the cells in the population have targeted insertion of Nanoluc-HaloTag reporter gene on both AAVS1 alleles since the wild-type allele is absent, and there is only one additional random integration (FIG. 2A). The targeted NSCs maintain robust Nanoluc and HaloTag expression during prolonged NSC expansion, maintain normal karyotype, and can be induced to differentiate into Tuj+ neurons and GFAP+ astrocyte (FIG. 2B-D). Similarly, when tdTomato reporter was targeted at AAVS1 or CLYBL locus in H9NSCs or NCRM1NSCs most cells contain at least one targeted allele, with only 1-2 random integrations in small fraction of the population (FIG. 2A). tdTomato integrated at CLYBL locus also maintain robust expression in both undifferentiated NSCs and differentiated neurons (FIG. 13).

Figure 2E:
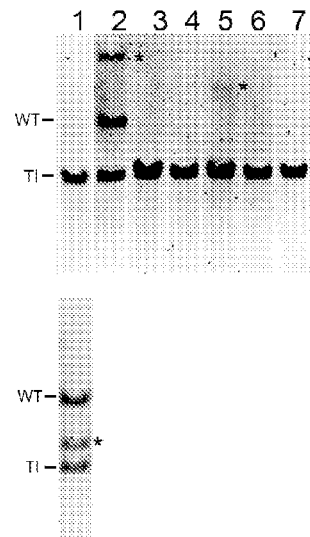
Figure 2F:
Figure 2G:
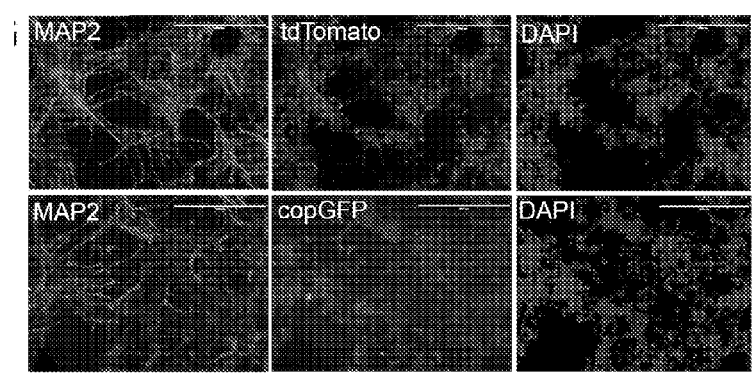
Figure 2H:
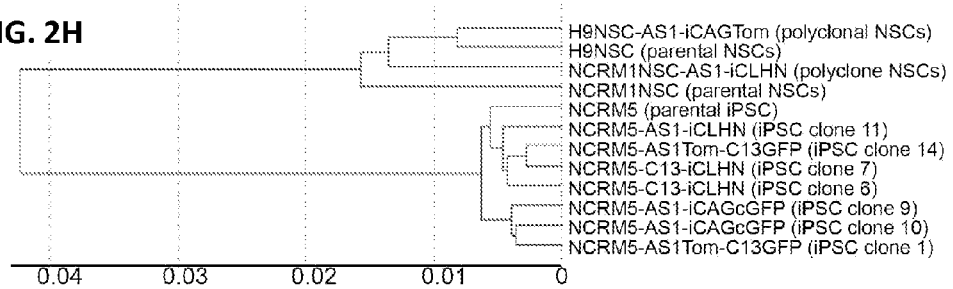
Figure 14A:
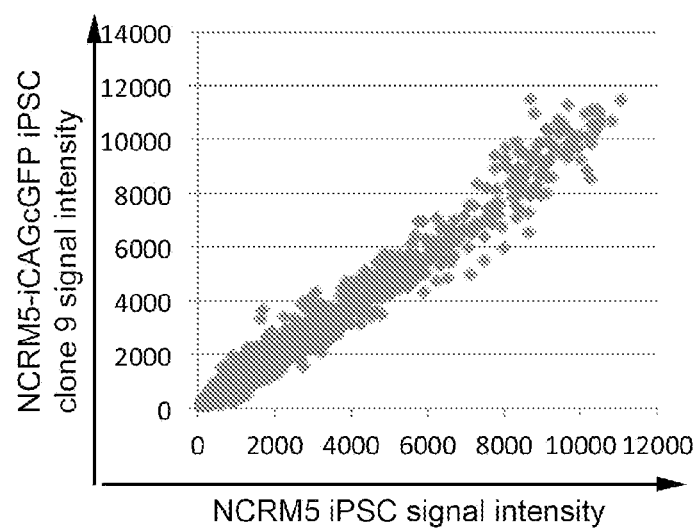
FIGS. 14A-14B. Scatter plots of gene expression comparison between non-targeted and safe-harbor targeted cells. (A) NCRM5 iPSCs compared with an AAVS1 targeted NCRM5-AS1-iCAGcGFP clone 9. $R^2$=0.99. (B) NCRM1NSC compared with AAVS1 targeted NCRM1NSC-AS1-iCLHN. $R^2$=0.98.
Figure 14B:
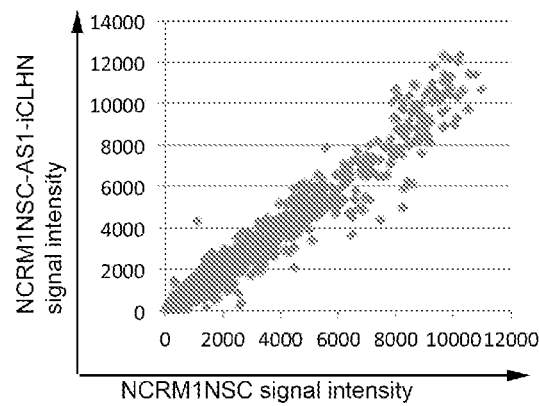

Since it's unlikely to avoid small fraction of RI within a polyclonal NSC population, a limiting dilution or counter-selection approach is needed to obtain clonal TI-only NSCs. Because human ESC/iPSC-derived NSCs can be maintained >20 passages and most drug-selected safe-harbor targeted iPSCs and NSCs only have TI, simultaneous dual safe-harbor targeting was carried out in NSCs, and 1-10 NSCs were plate per 96-well after drug selection. After 2-weeks, NSC clones were apparent in ~10% wells and those showing double fluorescent protein expression were expanded and analyzed. Southern blot results confirmed all the clones have AAVS1 and CLYBL dual safe-harbor TI, and TI-only NSC clones can be readily obtained (FIG. 2E-F). Using directed differentiation protocols, dual safe-harbor targeted NSCs differentiate into committed neurons or astrocytes without silencing of reporter genes at either safe harbor (FIG. 2G). Finally gene expression profiles of non-targeted (parental) and safe-harbor targeted iPSC and NSCs were compared. The results showed high correlation co-efficiency between parental and targeted cells. The correlation co-efficient ($R^2$) between non-targeted iPSCs and single or dual safe harbor targeted iPSC clones are all >0.99. For NSCs, even though polyclonal targeted NSCs were used to compare with non-targeted lines, $R^2$ are still >0.98 (FIGS. 2H and 14). These results suggested targeted integration of various transgenes at AAVS1 and CLYBL safe harbors in human iPSCs or NSCs, even up to all four alleles, have minimal impact on genome-wide expression.

The results demonstrated that safe harbor TALEN-mediated HDR is a high-efficiency method to generate targeted mini-gene transfer or reporter knock-in cell lines in both human iPSCs and NSCs. Similar gene editing efficiency was observed among pZT TALENs, Goldy TALENs and CRISPR targeting the same sequence (FIG. 3). The results suggested 1) truncated N-/C-terminus from different *Xanthomonas* species give the similar TALEN activity; 2) optimization of TALEN delivery parameters such as lower TALEN/donor ratio is important to achieve higher TALEN-mediated gene editing, which is similar to what was observed in ZFNs case (Zou et al., Cell stem cell 5, 97-110 (2009)); 3) for transcriptionally active locus, TALEN activity is not hampered by DNA methylation (Chen et al., Nucleic acids research 41, 2769-2778 (2013)) therefore can provide similar high-efficiency genome editing as CRISPR/Cas.

Taking advantage of drug-selection driven by endogenous PPP1R12C or CLYBL "safe harbor" promoter that is constitutively expressed, nearly 100% targeted knock-in of various reporter cassettes up to 8 kb into was repeatedly achieved in either or both safe harbors ranging from single-allele TI to all four alleles simultaneously (Tables 1 and 2).

cially for weak promoter-driven transgenes. Safe harbor TALENs also mediate efficient generation of engineered NSC lines and clones, which maintain multi-potency and robust transgene expression during expansion and differentiation into neurons and astrocytes. With recombination-mediated cassette exchange (RMCE) elements[20] that were also built in some safe harbor donors, engineered "founder" iPSC and NSC lines can be further modified to create secondary cell lines without using TALENs. The versatile toolbox of safe harbor TALENs and donor vectors as disclosed herein provide a flexible system to engineer multiplex reporter and transgene cassettes in human iPSCs and NSCs.

Example 2

Exemplary Protocol

The AAVS1 safe-harbor locus within the PPP1R12C gene has robust (Lombardo et al., Nat Methods. 2011 Aug. 21; 8(10):861-9. doi: 10.1038/nmeth.1674) and long-term (DeKelver et al., Genome Res. 2010; 20:1133-1142) expression of targeted transgenes without perturbation of neighboring gene transcription (Lombardo et al., op cit.) and apparent dispensability of the PPP1R12C gene in hESCs and iPSCs (DeKelver et al., op cit.)

By utilizing the improved genome-editing ability of TALENs NSCs were directly targeted at the AAVS1 safe harbor

TABLE 2

Summary of safe harbor targeted NSCs

| Parental NSC | Locus | Donor | Poly-/monoclonal | Integration | Validated differentiation | Reporter expression |
|---|---|---|---|---|---|---|
| NCRM1NSC | AAVS1 | iCLHN | polyclonal | Nearly all cells have 2TI@AAVS1 + 2 additional RI | Neuron & Astrocyte | ~100% positive, and persistent |
| NCRM1NSC | AAVS1 | iCAGtdTom | Polyclonal | Most cells have 1TI@AAVS1, small fraction has 2 RI | Not done yet | >90% positive, and persistent |
| H9NSC | AAVS1 | iCAGtdTom | Polyclonal | Most cells have 1TI@AAVS1, small fraction has 1 RI | Not done yet | >90% positive, and persistent |
| H9NSC | CLYBL | iCAGtdTom | Polyclonal | Most cells have 1TI@AAVS1, small fraction has 1 RI | Neuron | >90% positive, and persistent |
| NCRM1NSC | AAVS1 + CLYBL | iCAGtdTom + iCAGcGFP | Monoclonal | Most clones have 2TI@AAVS1, 1TI@CLYBL | Neuron & Astrocyte | ~100% positive, and persistant |

Figure 16:
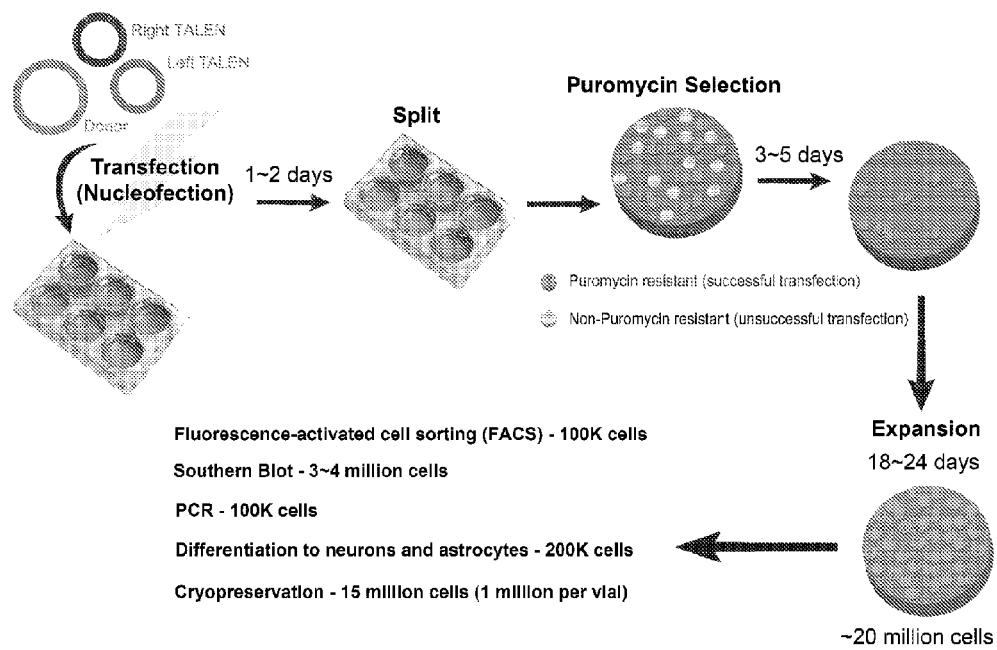
FIG. 16. Workflow for targeting NSCs with AAVS1 donor vector and TALENs. A description of the workflow required to generate a targeted NSC beginning with nucleofection of appropriate vectors and proceeding to selection, characterization and cryopreservation of appropriately targeted clones.

Thus fluorescent gene or Nanoluc luciferase reporter iPSC clones were generated in which the well-controlled gene expression provides sensitive and quantitative measurement. CLYBL safe harbor on Chromosome 13 allows 5~10-fold stronger transgene expression than AAVS1 safe harbor, providing an alternative and potentially better solution for targeted gene transfer/knock-in and drug-screening, especially locus to constitutively express a fluorescent reporter and a puromycin resistance gene. By pooling the surviving targeted clones after puromycin selection, a highly pure engineered NSC population was obtained. Targeted NSCs maintained the capacity to self-renew and differentiate to neurons and astrocytes. Engineering at the CYBL locus could also be used. See FIGS. 15 and 16.

| 2 Materials | |
|---|---|
| 2.1 Cells | 1. Human neural stem cells (NSCs) such as iPSC or hESC-derived. Low passage preferable.<br>2. Examples:<br>  NCRM-1 neural stem cells (Lonza)<br>  H9 neural stem cells (Life Technologies) |
| 2.2 Culture Reagents | 1. KNOCKOUT ™ DMEM/F-12 Basal Medium (500 mL; store in dark 2 to 8° C.), LifeTechnologies 12660-012<br>2. STEMPRO ® Neural Supplement (10 mL; store frozen at −5 to −20° C.), LifeTechnologies A10508-01<br>3. GLUTAMAX ™ Supplement (100 mL; 15° C. to 30° C.), LifeTechnologies 35050-061<br>4. FGF-Basic (AA 10-155) Recombinant Human Protein, (10 μg), LifeTechnologies PHG0024<br>5. EGF Recombinant Human Protein (10 μg), LifeTechnologies PHG0314<br>6. DMEM/F-12 Basal Medium (500 mL; store in dark 2 to 8° C.), LifeTechnologies 11320-033<br>7. GELTREX ™ LDEV-Free Reduced Growth Factor Basement Membrane Matrix (1 mL; Store at −20 to −80° C.), LifeTechnologies A1413201<br>8. STEMPRO ® ACCUTASE ® Cell Dissociation Reagent (100 mL; store at −20° C. upon receipt. After thawing store at 4° C.), LifeTechnologies A11105-01 |
| 2.3 Culture plates | 1. Standard 6-well and larger plates for expansion (Corning Life Sciences) |
| 2.4 Equipment | 1. Tissue culture microscope<br>2. Tissue culture incubator at 37° C., 5% $CO_2$, 85% relative humidity<br>3. Amaxa 4D nucleofector (Lonza, Switzerland) consisting of 4D-NUCLEOFECTOR ™ Core unit AAF-1001B and 4D-NUCLEOFECTOR ™ X unit (AAF-1001X)<br>4. P3 Primary Cell 4D-NUCLEOFECTOR ® X Kit S (two 16-well strips; 32 reactions) (V4XP-3032 Lonza, Switzerland)<br>5. P3 Primary Cell 4D-Nucleofector ® X Kit L (12 cuvettes; 12 reactions) (V4XP-3012 Lonza, Switzerland)<br>6. P4 Primary Cell 4D-NUCLEOFECTOR ® X Kit S (two 16-well strips; 32 reactions) (V4XP-4032 Lonza, Switzerland)<br>7. P4 Primary Cell 4D-NUCLEOFECTOR ® X Kit L (12 cuvettes; 12 reactions) (V4XP-4012 Lonza, Switzerland)<br>8. Centrifuge<br>9. Cell Counter (automated or hematocytometer) |

| 2.5 Reagents Setup<br>2.5.1 NSC SFM Medium (Store at 4° C. for up to 2 weeks) | Final Concentration | Volume per 100 mL of media |
|---|---|---|
| KNOCKOUT ™ DMEM/F-12 | — | 97 mL |
| STEMPRO ® Neural Supplement | — | 2 mL |
| GLUTAMAX ™ Supplement | 2 mM | 1 mL |
| EGF (100 ug/mL stock solution) | 20 ng/mL | 20 μL |
| FGF (100 ug/mL stock solution) | 20 ng/mL | 20 μL |

| 3 Methods | |
|---|---|
| 3.1 TALEN and donor vectors | Construct appropriate vectors for targeting the AAVS1 Safe-Harbor site. There will be two TALEN vectors; one of which will bind on the DNA on the upstream side of the target genomic insertion site, and the other which will bind the downstream side on the opposite strand. The donor vector should include left and right homology arms to the insertion site, antibiotic resistance gene for selection, and a reporter driven by either a constitutive, inducible, or lineage-specific promoter. See FIG. 15 |

| 3 Methods | |
|---|---|
| 3.3 Geltrex-Coating Plates | Allow a bottle (or aliquot) of growth factor-reduced Geltrex (see 7 of Culture Reagents) to thaw in a 4° C. refrigerator. Add 10 µL of cold (4° C.) Geltrex to 6 mL of cold (4° C.) DMEM/F12 (a 1:600 dilution) and mix thoroughly. Plate 1 mL of Geltrex per well in a 6-well culture plate. If using later, seal the edges of the plate with Parafilm and store at 4° C. for up to 2 weeks. Before using plate, incubate the plate at 37° C. for 1 hr. Allow plate to then cool to approximately room temperature for a few minutes before aspirating. Add 2 mL NSC SFM media per each well in 6-well plate. Allow plate to warm in 37° C. incubator while proceeding with cell preparation and nucleofection steps. |
| 3.2 Mixing of transfection DNA | Preparing DNA mixture is recommended before cell collection and subsequent nucleofection especially if nucleofecting multiple samples of donors or TALENs. In some embodiments, the DNA comprises no more than 10% of the total nucleofected solution. Thus DNA of sufficient high concentration (>1 µg/µL) is ideal. In microcentrifuge tubes, combine the left and right TALEN vectors and donor vector DNA in a 1:1:1 ratio. In each tube, add enough nucleofection solution (such as P3 or P4) to bring the total volume to 5 µL if using a 16-well strip, or 20 µL +if using the cuvettes. The cells re-suspended in nucleofection solution are added to these tubes before final transfer to the cuvettes or 16-well strips for nucleofection. (The DNA is mixed ahead of time in order to minimize the time of the nucleofection procedure and exposure time of the NSCs to nucleofection solution. Adding the re-suspended cells from a pooled count avoids having to aspirate supernatant from multiple tubes, which may introduce slight variability.) |
| 3.2 Cell Preparation and Collection | When NSCs are confluent or nearly confluent (~120,000 cells/$cm^2$), aspirate the medium. Dislodge the cells from the culture plate by adding enough room temperature Accutase to coat the well surface. (1 mL of Accutase for a single well of a 6-well plate.) Incubate the plate at 37° C., observing every few minutes until the cells have sufficiently disassociated from the well. Add an equal amount of warmed NSC SFM medium and transfer the collected cells into a 15 mL conical tube. Additional warmed NSC SFM can be added to further dilute the Accutase if desired. Centrifuge at 1000 rpm for 4 minutes to pellet the cells. Re-suspend the cells in 1-3 mL of NSC SFM medium to approximate the cell count using an automated cell counter. For 16-well strips (20 µL) nucleofecting can be performed in between 300K to 1 million NSCs. For the cuvettes (100 µL) nucleofecting can be performed between 1 million to 5 million NSCs. Pipet the desired amount cell solution into appropriate number of microcentrifuge (or conical) tubes and centrifuge once again at 1000 rpm for 4 minutes. (Volumes multiplied by 1.05 for both the amount of cells and amount of nucleofection solution for re-suspension, to account for pipetting volume loss.) |
| 3.4 Nucleofection | 1. Turn on the Nucelofection device and select the appropriate nucleoefection settings (volume, solution, and program). (For human NSCs, P4 solution (Program DN-100) and P3 solution (DC-100) to work well).<br>2. Remove the supernatant from the centrifuged tubes, leaving the cell pellet intact.<br>3. Re-suspend the cell pellet in the appropriate nucleofection solution and amount. (If using cuvettes: 80 µL x number of nucleofection samples. If using well of 16-well strip: 15 µL x number of nucleofection samples. Volumes multiplied by 1.05 can be used for both the amount of cells and amount of nucleofection solution for re-suspension, to account for pipetting volume loss.)<br>4. For cuvettes, add 80 µL of re-suspended cell solution into the appropriate (previously prepared) DNA sample microcentrifuge tubes. For a well of a 16-well strip, add 15 µL of re-suspended cell solution into the appropriate (previously prepared) DNA sample microcentrifuge tubes.<br>5. Gently mix solution and transfer tube contents to cuvettes or 16-well strips. The cuvettes and 16-well strips can be labeled for identification with a marker.<br>6. Place the cuvettes or 16-well strip into the nucleofection |

| 3 Methods | |
|---|---|
| | X-unit and proceed with nucleofection.<br>7. Immediately add 500 µL of warm NSC SFM media to cuvettes or 100 µL of warm NSC SFM media to a well of a 16-well strip.<br>8. Pipet nucleofected contents slowly and gently into prepared culture plates with pre-warmed NSC SFM.<br>9. It may take at least 36 hours for TALEN action and homology-directed donor vector targeting to sufficiently occur. Donor construct expression may transiently express for up to a week.<br>10. Successful nucleofection can be determined by observing reporter fluorescence under the microscope (if reporter should be expressed), and surviving number of cells. |
| 3.5 Expansion of NSCs | Passaging is possible at 80% confluency and 1.5 days/36 hours after nucleofection. After puromycin selection, passaging is not recommended until proliferation resumes (~2 days) and cells are at again 80% confluency. |
| 3.6 Drug selection of targeted NSCs | Antibiotic kill-curve should be generated using cell controls at similar plating density. Minimal concentration of antibiotic which completely kill all untransfected cells in 1-3 days should be used for selection of transfected cells. |
| 3.7 Characterization of targeted NSCs | Observe surviving cells for reporter expression under fluorescence microscope. |
| 3.7.1 Fluorescence-activated cell sorting (FACS) | Selected and subsequently expanded NSCs can be characterized by fluorescence-activated cell sorting (FACS) to determine targeted population purity. 100,000 cells were harvested and standard machine protocols were used. |
| 3.7.2 PCR | Genomic DNA was harvested from approximately 100,000 cells from a single well of a confluent 24-well plate.<br>The primer sequence used was:<br>AAVS1U-F2:<br>5-CTGCCGTCTCTCTCCTGAGT (SEQ ID NO: 20)<br>and<br>PuroU-R:<br>5-GTGGGCTTGTACTCGGTCAT (SEQ ID NO: 21).<br>PCR reaction was run following the PCR Protocol for PHUSION® High-Fidelity DNA Polymerase (M0530, New England BioLabs).<br>The resulting reaction was run on a 1% agarose gel and examined for a 1 kb band. |
| 3.7.3 Southern Blot | Genomic DNA was harvested from 3-4 million cells from approximately 2 confluent wells of 6-well plates. DNA was digested with SphI and run on a 0.7% agarose gel at 120 V for 1.5 hrs.<br>DNA from gel was transferred to positively charged nylon, UV crosslinked, and DIGG-labeled 5' probe was added. Probe was hybridized to DNA and washed with decreasing concentrations of SSC (saline sodium citrate) and 0.1% SDS.<br>Signal was detected with 30 minutes of signal accumulation in a photometer. |
| 3.8 Differentiation Potential of Targeted NSCs | Confirmed NSCs have capacity to differentiate to astrocytes and neurons using published protocols. |

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of making a double stranded break in an endogenous CLYBL gene in an isolated human cell, said method comprising introducing into the cell
   (a) an upstream transcription activator-like effector nuclease (TALEN) comprising an upstream DNA-binding domain linked to a DNA cleavage domain; and
   (b) a downstream transcription activator-like effector nuclease (TALEN) comprising a downstream DNA-binding domain linked to a DNA cleavage domain;

so that a double stranded break in the endogenous CLYBL gene in the isolated human cell occurs.

* * * * *